(12) United States Patent
Morooka et al.

(10) Patent No.: US 11,078,180 B2
(45) Date of Patent: Aug. 3, 2021

(54) CURED PRODUCT, OPTICAL MEMBER, LENS, COMPOUND, AND CURABLE COMPOSITION

(71) Applicant: FUJIFILM Corporation, Tokyo (JP)

(72) Inventors: Naoyuki Morooka, Kanagawa (JP); Naozumi Shiraiwa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/803,896

(22) Filed: Feb. 27, 2020

(65) Prior Publication Data

US 2020/0199095 A1     Jun. 25, 2020

Related U.S. Application Data

(63) Continuation of application No. PCT/JP2018/031850, filed on Aug. 29, 2018.

(30) Foreign Application Priority Data

Aug. 30, 2017   (JP) .............. JP2017-166149
Jun. 6, 2018    (JP) .............. JP2018-108500

(51) Int. Cl.
| | |
|---|---|
| *C07D 339/06* | (2006.01) |
| *C07D 277/82* | (2006.01) |
| *C07D 409/04* | (2006.01) |
| *C07D 417/04* | (2006.01) |
| *C08F 220/28* | (2006.01) |
| *C08F 222/10* | (2006.01) |
| *G02B 1/04* | (2006.01) |

(52) U.S. Cl.
CPC ......... *C07D 339/06* (2013.01); *C07D 277/82* (2013.01); *C07D 409/04* (2013.01); *C07D 417/04* (2013.01); *C08F 220/28* (2013.01); *C08F 222/10* (2013.01); *G02B 1/04* (2013.01)

(58) Field of Classification Search
CPC .................................................. C07D 339/06
USPC ............................................................ 549/37
See application file for complete search history.

(56) References Cited

U.S. PATENT DOCUMENTS

| | | |
|---|---|---|
| 2013/0237630 A1 | 9/2013 | Morooka et al. |
| 2015/0175731 A1 | 6/2015 | Saitoh |
| 2015/0277006 A1 | 10/2015 | Takasago et al. |
| 2016/0068756 A1 | 3/2016 | Moriya et al. |
| 2016/0108315 A1 | 4/2016 | Matsuyama et al. |
| 2018/0066189 A1 | 3/2018 | Ishii et al. |
| 2018/0362847 A1 | 12/2018 | Saito et al. |
| 2019/0271885 A1 | 9/2019 | Takahashi et al. |

FOREIGN PATENT DOCUMENTS

| | | |
|---|---|---|
| CN | 104950371 A | 9/2015 |
| CN | 105524625 A | 4/2016 |
| JP | 2008-107767 A | 5/2008 |
| JP | 2009-126011 A | 6/2009 |
| JP | 2009-242718 A | 10/2009 |
| JP | 2009-263617 A | 11/2009 |
| JP | 2012-021068 A | 2/2012 |
| JP | 2012-077057 A | 4/2012 |
| JP | 2012-107191 A | 6/2012 |
| JP | 2013-071956 A | 4/2013 |
| JP | 2014-043565 A | 3/2014 |
| JP | 2016-051083 A | 4/2016 |
| JP | 2016-051178 A | 4/2016 |

(Continued)

OTHER PUBLICATIONS

International Search Report issued in PCT/JP2018/031850; dated Oct. 30, 2018.

(Continued)

*Primary Examiner* — Taofiq A Solola
(74) *Attorney, Agent, or Firm* — Studebaker & Brackett PC

(57) ABSTRACT

According to the present invention, a cured product obtained by curing a curable composition including a compound represented by General Formula 1, in which a birefringence Δn (587 nm) is 0.00≤Δn (587 nm)≤0.01, is provided, and this cured product is suitable for manufacturing an optical member.

$$Pol_1\text{-}Sp_1\text{-}L_1\text{-}Ar\text{-}L_2\text{-}Sp_2\text{-}Pol_2 \qquad \text{(General Formula 1)}$$

In formula, Ar is an aromatic ring group represented by General Formula 2-2 and the like.

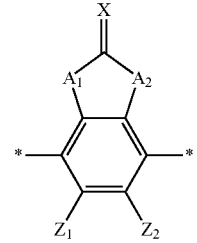

General Formula 2-2

In formula, $Z_1$ and $Z_2$ each represent a hydrogen atom, a methyl group, and the like; $A_1$ and $A_2$ each represent —S— and the like; X represents $C(Rz)_2$ and the like (where Rz is a substituent, and two Rz's may form a ring); $L_1$ and $L_2$ each represent a single bond, —O—, —OC(=O)—, —OC(=O)O—, —OC(=O)NH—, and the like; $Sp_1$ and $Sp_2$ each represent a single bond or a divalent linking group; $Pol_1$ and $Pol_2$ each represent a hydrogen atom or a polymerizable group; and a compound represented by General Formula 1 has at least one polymerizable group.

16 Claims, No Drawings

(56) References Cited

FOREIGN PATENT DOCUMENTS

| JP | 2016-053709 A | 4/2016 |
| JP | 2016-081035 A | 5/2016 |
| WO | 2013/018526 A1 | 2/2013 |
| WO | 2016/114347 A1 | 7/2016 |
| WO | 2017/043438 A1 | 3/2017 |
| WO | 2017/098988 A1 | 6/2017 |
| WO | 2018/012390 A1 | 1/2018 |
| WO | 2018/123551 A1 | 7/2018 |

OTHER PUBLICATIONS

International Preliminary Report on Patentability issued in PCT/JP2018/031850; completed Nov. 7, 2019.

Duoli Sun et al.; "Benzoguinone derived 1,3-dithiole-2-ones and thiones"; Journal of Chemical Crystallography; 1997; pp. 515-526; vol. 27, No. 9.

Frédéric Dumur et al.; "Novel Fused D-A Dyad and A-D-A Triad Incorporating Tetrathiafulvalene and p-Benzoguinone"; Journal of Organic Chemistry; 2004; pp. 2164-2177; vol. 69, No. 6.

An Office Action; "Notice of Reasons for Refusal", mailed by the Japanese Patent Office dated Mar. 23, 2021, which corresponds to Japanese Patent Application No. 2019-539553 and is related to U.S. Appl. No. 16/803,896; with English language translation.

An Office Action mailed by China National Intellectual Property Administration dated May 18, 2021, which corresponds to Chinese Patent Application No. 201880054910.4 and is related to U.S. Appl. No. 16/803,896; with English language translation.

CURED PRODUCT, OPTICAL MEMBER, LENS, COMPOUND, AND CURABLE COMPOSITION

CROSS-REFERENCE TO RELATED APPLICATIONS

This application is a continuation of PCT International Application No. PCT/JP2018/031850 filed on Aug. 29, 2018, which claims priorities under 35 U.S.C § 119 (a) to Japanese Patent Applications Nos. 2017-166149 and 2018-108500 filed on Aug. 30, 2017 and Jun. 6, 2018, respectively, and the entire contents of which are incorporated herein by reference.

BACKGROUND OF THE INVENTION

1. Field of the Invention

The present invention relates to a cured product, an optical member, a lens, a compound, and a curable composition.

2. Description of the Related Art

Conventionally, a glass material has been used for an optical member of an imaging module such as a camera, a video camera, a mobile phone with a camera, a video phone, or a door phone with a camera. Glass materials have been used preferably because they have various optical characteristics and excellent environmental resistance, but they have a disadvantage in that weight reduction and miniaturization are not easy and workability or productivity is poor. In contrast, since a resin cured product can be produced in a massive amount and has excellent workability, the resin cured product has recently been used in various optical members.

In recent years, in accordance with miniaturization of an imaging module, a size of an optical member used in the imaging module is required to be reduced, but in a case of miniaturizing an optical member, a problem of chromatic aberration occurs. In an optical member formed of a cured resin, studies have been conducted regarding adjusting an Abbe number by adding various additives to a curable composition to change characteristics of a product after curing, and then correcting chromatic aberration.

For example, JP2014-043565A discloses that, using a 4,4'-bis(aryl)diphenylsulfone skeleton monomer, it is possible to provide a molded article having a large Abbe number (vd), a high partial dispersion ratio (θg, F), and a low birefringence index, which are characteristics of an excellent chromatic aberration correction performance; an optical element; and an optical composition for obtaining the molded article.

Meanwhile, WO2016/114347A discloses a liquid crystal monomer having an aromatic ring group such as benzodithiol and benzothiazole.

SUMMARY OF THE INVENTION

An object of the present invention is to provide a cured product having a small Abbe number (vd) and a high partial dispersion ratio (θg, F) for manufacturing an optical member. In particular, an object of the present invention is to provide a cured product which has a partial dispersion ratio higher than that of the cured product disclosed in JP2014-043565A, and which does not exhibit a birefringent property as that of the cured product disclosed in WO2016/114347A. Another object of the present invention is to provide a highly functional optical member and lens.

The inventors of the present invention have diligently studied to achieve the above-described objects, and have found that, by using a compound having an aromatic ring group including benzodithiol and benzothiazole, it is possible to obtain a cured product having a small Abbe number and a high partial dispersion ratio.

That is, specific means for achieving the above-described objects are as follows.

[1] A cured product obtained by curing a curable composition including a compound represented by General Formula 1, in which a birefringence Δn at a wavelength of 587 nm is $0.00 \leq \Delta n \leq 0.01$.

$$Pol_1\text{-}Sp_1\text{-}L_1\text{-}Ar\text{-}L_2\text{-}Sp_2\text{-}Pol_2 \qquad \text{(General Formula 1)}$$

In formula, Ar is any aromatic ring group represented by General Formulas 2-1 to 2-4.

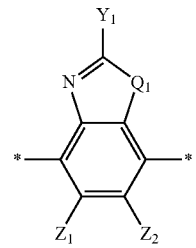

General Formula 2-1

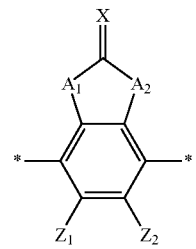

General Formula 2-2

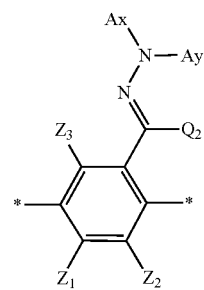

General Formula 2-3

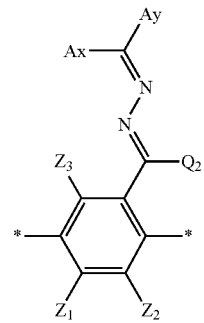

General Formula 2-4

In formulas, $Q_1$ represents —S—, —O—, or $NR_{11}$—, and $R_{11}$ represents a hydrogen atom or an alkyl group having 1 to 6 carbon atoms, $Y_1$ represents an alkyl group which has 1 to 6 carbon atoms and may have a substituent; an aromatic hydrocarbon group which has 6 to 12 carbon atoms and may have a substituent; or an aromatic heterocyclic group which has 3 to 12 carbon atoms and may have a substituent, $Z_1$, $Z_2$, and $Z_3$ each independently represent a hydrogen atom, an aliphatic hydrocarbon group which has 1 to 20 carbon atoms and may have a substituent, an alkoxy group which has 1 to 20 carbon atoms and may have a substituent, an alicyclic hydrocarbon group which has 3 to 20 carbon atoms and may have a substituent, a monovalent aromatic hydrocarbon group which has 6 to 20 carbon atoms and may have a substituent, a halogen atom, a cyano group, a nitro group, —$NR_{12}R_{13}$, or $SR_{12}$, where, $Z_1$ and $Z_2$ may be bonded to each other to form an aromatic hydrocarbon ring which may have a substituent or an aromatic heterocyclic ring which may have a substituent, and $R1_2$ and $R_{13}$ each independently represent a hydrogen atom or an alkyl group having 1 to 6 carbon atoms, $A_1$ and $A_2$ each independently represent a group selected from the group consisting of —O—, —$NR_{21}$—, —S—, and CO—, and $R_{21}$ represents a hydrogen atom or a substituent, X represents O, S, C to which a hydrogen atom or a substituent is bonded, or N to which a hydrogen atom or a substituent is bonded, Ax represents an organic group which has 1 to 30 carbon atoms and has at least one aromatic ring selected from the group consisting of an aromatic hydrocarbon ring and an aromatic heterocyclic ring; and Ay represents a hydrogen atom, an alkyl group which has 1 to 6 carbon atoms and may have a substituent, or an organic group which has 1 to 30 carbon atoms and has at least one aromatic ring selected from the group consisting of an aromatic hydrocarbon ring and an aromatic heterocyclic ring, where, the aromatic ring included in Ax and Ay may have a substituent, and Ax and Ay may be bonded to each other to form a ring which may have a substituent, $Q_2$ represents a hydrogen atom or an alkyl group which has 1 to 6 carbon atoms and may have a substituent, $L_1$ and $L_2$ each independently represent a single bond, or a linking group selected from the group consisting of —O—, —S—, —C(=O)—, —OC(=O)—, —C(=O)O—, —OC(=O)O—, —$NR_{101}$C(=O)—, —C(=O)$NR_{102}$—, —OC(=O)$NR_{103}$—, —$NR_{104}$C(=O)O—, —SC(=O)—, or C(=O)S—, where $R_{101}$, $R_{102}$, $R_{103}$, and $R_{104}$ each independently represent -$Sp_3$-$Pol_3$ or a halogen atom, $Sp_1$, $Sp_2$, and $Sp_3$ each independently represent a single bond or a divalent linking group, $Pol_1$, $Pol_2$, and $Pol_3$ each independently represent a hydrogen atom or a polymerizable group, and the compound represented by General Formula 1 has at least one polymerizable group.

[2] The cured product according to [1], in which Ar is an aromatic ring group represented by General Formula 2-2.

[3] The cured product according to [1] or [2], in which $Sp_1$ and $Sp_2$ each represent a single bond, or a linking group selected from the group consisting of a linear alkylene group which has 1 to 30 carbon atoms and may have a substituent and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S— in a linear alkylene group which has 2 to 30 carbon atoms and may have a substituent, where $R_{201}$, $R_{202}$, $R_{203}$, and $R_{204}$ each independently represent -$Sp_4$-$Pol_4$ or a halogen atom, $Sp_4$ represents a single bond or a divalent linking group, and $Pol_4$ represents a hydrogen atom or a polymerizable group.

[4] The cured product according to any one of [1] to [3], in which $L_1$ and $L_2$ are all —O—, —OC(=O)—, —OC(=O)O—, or O—C(=O)NH—.

[5] The cured product according to [4], in which $L_1$ and $L_2$ are all —O—.

[6] The cured product according to any one of [1] to [5], in which the polymerizable groups are all (meth)acryloyloxy groups.

[7] The cured product according to any one of [1] to [6], in which any of $Pol_1$ or $Pol_2$ is a (meth)acryloyloxy group.

[8] An optical member comprising the cured product according to any one of [1] to [7].

[9] A lens comprising the cured product according to any one of [1] to [7].

[10] A compound represented by General Formula 1.

$$Pol_1\text{-}Sp_1\text{-}L_1\text{-}Ar\text{-}L_2\text{-}Sp_2\text{-}Pol_2 \quad \text{(General Formula 1)}$$

In formula, Ar is any aromatic ring group represented by General Formulas 2-1 to 2-4.

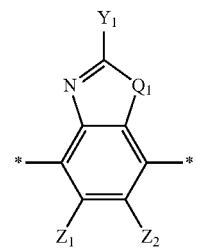

General Formula 2-1

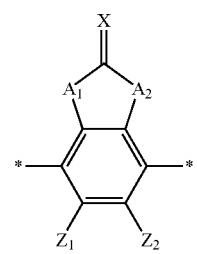

General Formula 2-2

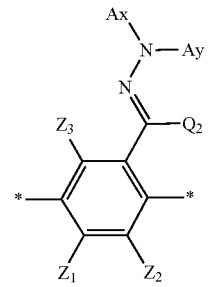

General Formula 2-3

-continued

General Formula 2-4

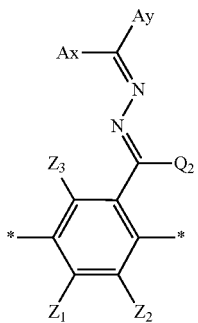

In formulas, $Q_1$ represents —S—, —O—, or $NR_{11}$, and $R_{11}$ represents a hydrogen atom or an alkyl group having 1 to 6 carbon atoms, $Y_1$ represents an alkyl group which has 1 to 6 carbon atoms and may have a substituent; an aromatic hydrocarbon group which has 6 to 12 carbon atoms and may have a substituent; or an aromatic heterocyclic group which has 3 to 12 carbon atoms and may have a substituent, $Z_1$, $Z_2$, and $Z_3$ each independently represent a hydrogen atom, an aliphatic hydrocarbon group which has 1 to 20 carbon atoms and may have a substituent, an alkoxy group which has 1 to 20 carbon atoms and may have a substituent, an alicyclic hydrocarbon group which has 3 to 20 carbon atoms and may have a substituent, a monovalent aromatic hydrocarbon group which has 6 to 20 carbon atoms and may have a substituent, a halogen atom, a cyano group, a nitro group, —$NR_{12}R_{13}$, or $SR_{12}$, where, $Z_1$ and $Z_2$ may be bonded to each other to form an aromatic hydrocarbon ring which may have a substituent or an aromatic heterocyclic ring which may have a substituent, and $R1_2$ and $R_{13}$ each independently represent a hydrogen atom or an alkyl group having 1 to 6 carbon atoms, $A_1$ and $A_2$ each independently represent a group selected from the group consisting of —O—, —$NR_{21}$—, —S—, and CO—, and $R_{21}$ represents a hydrogen atom or a substituent, X represents O, S, C to which a hydrogen atom or a substituent is bonded, or N to which a hydrogen atom or a substituent is bonded, Ax represents an organic group which has 1 to 30 carbon atoms and has at least one aromatic ring selected from the group consisting of an aromatic hydrocarbon ring and an aromatic heterocyclic ring; and Ay represents a hydrogen atom, an alkyl group which has 1 to 6 carbon atoms and may have a substituent, or an organic group which has 1 to 30 carbon atoms and has at least one aromatic ring selected from the group consisting of an aromatic hydrocarbon ring and an aromatic heterocyclic ring, where, the aromatic ring included in Ax and Ay may have a substituent, and Ax and Ay may be bonded to each other to form a ring which may have a substituent, $Q_2$ represents a hydrogen atom or an alkyl group which has 1 to 6 carbon atoms and may have a substituent, $L_1$ and $L_2$ each independently represent a single bond, or a linking group selected from the group consisting of —O—, —S—, —C(=O)—, —OC(=O)—, —C(=O)O—, —OC(=O)O—, —$NR_{101}$C(=O)—, —C(=O)$NR_{102}$—, —OC(=O)$NR_{103}$—, —$NR_{104}$C(=O)O—, —SC(=O)—, or C(=O)S—, where $R_{101}$, $R_{102}$, $R_{103}$, and $R_{104}$ each independently represent -$Sp_3$-$Pol_3$ or a halogen atom, $Sp_1$ and $Sp_2$ each represent a single bond, or a linking group selected from the group consisting of a linear alkylene group which has 1 to 30 carbon atoms and may have a substituent and a group in which one or two or more non-adjacent —$CH_2$—'s are substituted by —O—, —S—, —C(=O)—, —OC(=O)—, —C(=O)O—, —OC(=O)O—, —$NR_{201}$C(=O)—, —C(=O)$NR_{202}$—, —OC(=O)$NR_{203}$—, —$NR_{204}$C(=O)O—, —SC(=O)—, or —C(=O)S— in a linear alkylene group which has 2 to 30 carbon atoms and may have a substituent, where $R_{201}$, $R_{202}$, $R_{203}$, and $R_{204}$ each independently represent -$Sp_4$-$Pol_4$ or a halogen atom, $Sp_3$ and $Sp_4$ each independently represent a single bond or a divalent linking group, $Pol_1$, $Pol_2$, $Pol_3$, and $Pol_4$ each independently represent a hydrogen atom or a polymerizable group, and the compound represented by General Formula 1 has at least one polymerizable group.

[11] The compound according to [10], in which Ar is an aromatic ring group represented by General Formula 2-2.

[12] The compound according to [10] or [11], in which $L_1$ and $L_2$ are all —O—, —OC(=O)—, —OC(=O)O—, or O—C(=O)NH—.

[13] The compound according to [12], in which $L_1$ and $L_2$ are all —O—.

[14] The compound according to any one of [10] to [13], in which the polymerizable groups are all (meth)acryloyloxy groups.

[15] The compound according to any one of [10] to [14], in which any of $Pol_1$ or $Pol_2$ is a (meth)acryloyloxy group.

[16] A curable composition comprising: the compound according to any one of [10] to [15], and a polyfunctional (meth)acrylate monomer having three or more (meth)acryloyl groups in a molecule.

According to the present invention, a cured product having a small Abbe number (vd) and a high partial dispersion ratio (θg, F) is provided. Using the cured product of the present invention, it is possible to provide a highly functional optical member and lens. In addition, according to the present invention, a novel compound that can provide the cured product having a small Abbe number (vd) and a high partial dispersion ratio (θg, F) is provided.

DESCRIPTION OF THE PREFERRED EMBODIMENTS

Hereinafter, the present invention will be described in detail. The description of constituent elements described below can be made based on representative embodiments and specific examples, but the present invention is not limited to such embodiments. Numerical value ranges expressed using "to" in the present specification mean a range including numerical values described before and after "to" as the lower limit and the upper limit In the present specification, "(meth)acrylate" refers to any one or both of acrylate and methacrylate, and "(meth) acryloyl" refers to any one or both of acryloyl and methacryloyl. The monomer in the present invention is a compound distinguished from oligomers and polymers and having a weight-average molecular weight of 1,000 or less.

In the present specification, in a case where an aliphatic hydrocarbon group is referred to, it represents a group obtained by removing one hydrogen atom from a linear or branched alkane, a linear or branched alkene, or a linear or branched alkyne. In the present specification, the aliphatic hydrocarbon group is preferably an alkyl group obtained by removing any one of hydrogen atoms from a linear or branched alkane.

In the present specification, in a case where an alkyl group is referred to, it represents a linear or branched alkyl group. Examples of alkyl groups include a methyl group, an ethyl group, a propyl group, an isopropyl group, a butyl group, an isobutyl group, a sec-butyl group, a tert-butyl group, a pentyl group, a 1-methylbutyl group, a 3-methylbutyl group, a hexyl group, a 1-methylpentyl group, a 4-methylpentyl group, a heptyl group, a 1-methylhexyl group, a 5-methylhexyl group, an octyl group, a 1-methylheptyl group, a nonyl group, a 1-methyloctyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and the like. The same applies to an alkyl group in groups (for example, an alkoxy group, an alkoxycarbonyl group, an acyl group, and the like) containing an alkyl group.

In addition, in the present specification, examples of linear alkylene groups include groups obtained by removing each hydrogen atom bonded to a terminal carbon from a linear alkyl group among the above-mentioned alkyl groups.

In the present specification, examples of alicyclic hydrocarbon rings include cyclopropane, cyclobutane, cyclopentane, cyclohexane, cycloheptane, cyclooctane, cyclononane, and cyclodecane.

In the present specification, examples of unsaturated hydrocarbon rings include indene, indane, and fluorene.

In the present specification, in a case where an alicyclic hydrocarbon group is referred to, it represents a cycloalkyl group obtained by removing any one of hydrogen atoms from cycloalkane. Examples of alicyclic hydrocarbon groups include a cyclopropyl group, a cyclobutyl group, a cyclopentyl group, a cyclohexyl group, a cycloheptyl group, a cyclooctyl group, a cyclononyl group, a cyclodecyl group, and the like, where a cycloalkyl group having 3 to 12 carbon atoms is preferable.

In the present specification, a cycloalkylene group represents a divalent group obtained by removing any two hydrogen atoms from cycloalkane. Examples of cycloalkylene groups include a cyclohexylene group.

In the present specification, in a case where an aromatic ring is referred to, it means any one or both of an aromatic hydrocarbon ring and an aromatic heterocyclic ring.

In the present specification, examples of aromatic hydrocarbon ring include benzene, biphenyl, biphenylene, naphthalene, anthracene, and phenanthrene.

In the present specification, in a case where an aromatic hydrocarbon group is referred to, it represents a monovalent group obtained by removing any one of hydrogen atoms from an aromatic hydrocarbon ring. Examples thereof include a phenyl group, a biphenyl group, a 1-naphthyl group, a 2-naphthyl group, a 1-anthracenyl group, a 2-anthracenyl group, a 3-anthracenyl group, a 4-anthracenyl group, a 9-anthracenyl group, a 1-phenanthryl group, a 2-phenanthryl group, a 3-phenanthryl group, a 4-phenanthryl group, a 9-phenanthryl group, and the like. In the present specification, in a case where a divalent aromatic hydrocarbon group is referred to, it represents a divalent group obtained by removing any two hydrogen atoms from an aromatic hydrocarbon ring. Examples thereof include a divalent group obtained by removing any one of hydrogen atoms from the above-mentioned (monovalent) aromatic hydrocarbon group.

In the present specification, examples of aromatic heterocyclic rings include furan, thiophene, pyrrole, imidazole, isothiazole, isoxazole, pyridine, pyrazine, quinoline, benzofuran, benzothiazole, benzoxazole, and the like.

In the present specification, in a case where an aromatic heterocyclic group is referred to, it represents a monovalent group obtained by removing any one of hydrogen atoms from an aromatic heterocyclic ring. Examples of monovalent aromatic heterocyclic groups include a furyl group, a thienyl group (preferably a 2-thienyl group), a pyrrolyl group, an imidazolyl group, an isothiazolyl group, an isoxazolyl group, a pyridyl group, a pyrazinyl group, a quinolyl group, a benzofuranyl group (preferably a 2-benzofuranyl group), a benzothiazolyl group (preferably a 2-benzothiazolyl group), a benzoxazolyl group (preferably a 2-benzoxazolyl group), and the like. In the present specification, in a case where a divalent aromatic heterocyclic group is referred to, it represents a divalent group obtained by removing any two hydrogen atoms from an aromatic heterocyclic ring. Examples thereof include a divalent group obtained by removing any one of hydrogen atoms from the above-mentioned (monovalent) aromatic heterocyclic group.

<Cured Product>

A cured product of the embodiment of the present invention is formed from a curable composition containing a compound represented by General Formula 1. The cured product of the embodiment of the present invention is obtained by polymerization of the compound represented by General Formula 1, but the cured product of the embodiment of the present invention may include an unreacted compound represented by General Formula 1.

The compound represented by General Formula 1 includes, within its structure, a fused ring of benzene such as benzodithiol or benzothiazole and a heterocyclic ring, or a benzene ring having hydrazone as a substituent. The inventors of the present invention have found that the cured product formed from the curable composition containing the compound represented by General Formula 1 has a small Abbe number (vd) and a high partial dispersion ratio ($\theta g$, F). Because the above-mentioned compound has absorption in a near ultraviolet region, it is considered to exhibit anomalous dispersibility of refractive index, thereby improving a chromatic aberration correction performance in a case of being used as a compound lens. The inventors of the present invention have further found that the cured product formed from the curable composition containing the compound represented by General Formula 1 has a high heat shock resistance. In the present specification, the heat shock resistance represents an ability to relieve stress at the time of heat change in a cured product.

An Abbe number (vd) and a partial dispersion ratio ($\theta g$, F) of the cured product are values measured using a Kalnew precision refractometer KPR-2000 (manufactured by Shimadzu Device Corporation). Specifically, the curable composition is poured into a transparent glass mold having a diameter of 20 mm and a thickness of 2 mm, and heated at 200° C. in an atmosphere having an oxygen concentration of 1% or less to form a cured product (a heating step), and an Abbe number (vd) and a partial dispersion ratio ($\theta g$, F) of this cured product are measured. The Abbe number (vd) and the partial dispersion ratio ($\theta g$, F) of the cured product are calculated by the following formula. In a case of molding a cured product, an ultraviolet irradiation step may be employed instead of the above-described heating step, or both of the heating step and the ultraviolet irradiation step may be employed.

$$vd = (nd-1)/(nF-nC)$$

$$\theta g, F = (ng-nF)/(nF-nC)$$

Where, nd represents a refractive index at a wavelength of 587.56 nm, nF represents a refractive index at a wavelength of 486.13 nm, nC represents a refractive index at a wavelength of 656.27 nm, and ng represents a refractive index at a wavelength of 435.83 nm.

The Abbe number of the cured product of the embodiment of the present invention is not particularly limited, but is preferably 30 or less, more preferably 27 or less, even more preferably 25 or less, and particularly preferably 23 or less. In addition, the Abbe number of the cured product of the embodiment of the present invention is not particularly limited, but it is preferably 1 or more, is more preferably 3 or more, is even more preferably 5 or more, and is particularly preferably 7 or more.

The partial dispersion ratio (θg, F) of the cured product of the embodiment of the present invention is not particularly limited, but it is preferably 0.65 or more, is more preferably 0.70 or more, and is even more preferably 0.75 or more. In addition, the partial dispersion ratio (θg, F) of the cured product of the embodiment of the present invention is not particularly limited, but it is preferably 2 or less, is more preferably 1.8 or less, and is even more preferably 1.7 or less.

A birefringence Δn at a wavelength of 587 nm of the cured product of the embodiment of the present invention (in the present specification, sometimes referred to as a birefringence Δn (587 nm)) is 0.00≤Δn≤0.01. The birefringence Δn (587 nm) is preferably 0.001 or less and is more preferably less than 0.001. By using a cured product having such a low birefringence index for an optical member of an imaging module, it is possible to obtain a clear image in which an imaging position is unlikely to shift. The lower limit value of the birefringence Δn (587 nm) may be 0.00001 or 0.0001.

The birefringence Δn (587 nm) of the cured product can be obtained by the following method. A film-like sample is produced, and using a birefringence evaluation apparatus (for example, WPA-100, manufactured by Photonic Lattice, Inc.), a birefringence within a 10 mm diameter circle including the center of the sample is measured, an average value of birefringence at a wavelength of 587 nm is obtained, and thereby a birefringence Δn (587 nm) can be obtained.

<Compound Represented by General Formula 1>

The cured product of the embodiment of the present invention is obtained by curing a curable composition containing a compound represented by General Formula 1.

$Pol_1\text{-}Sp_1\text{-}L_1\text{-}Ar\text{-}L_2\text{-}Sp_2\text{-}Pol_2$ (General Formula 1)

In formula, Ar is any aromatic ring group represented by General Formulas 2-1 to 2-4.

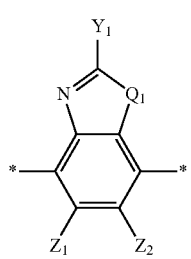

General Formula 2-1

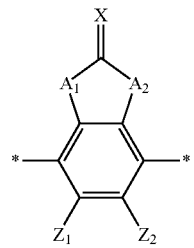

General Formula 2-2

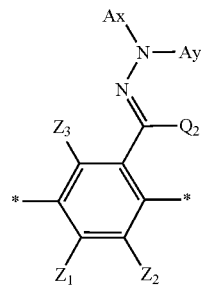

General Formula 2-3

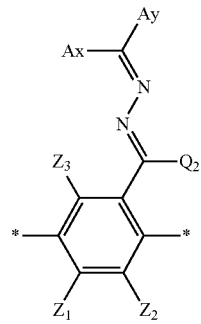

General Formula 2-4

In General Formulas 2-1 to 2-4, $Q_1$ represents —S—, —O—, or $NR_{11}$—, and $R_{11}$ represents a hydrogen atom or an alkyl group having 1 to 6 carbon atoms.

$Y_1$ represents an alkyl group which has 1 to 6 carbon atoms and may have a substituent; an aromatic hydrocarbon group which has 6 to 12 carbon atoms and may have a substituent; or an aromatic heterocyclic group which has 3 to 12 carbon atoms and may have a substituent.

$Z_1$, $Z_2$, and $Z_3$ each independently represent a hydrogen atom, an aliphatic hydrocarbon group which has 1 to 20 carbon atoms and may have a substituent, an alkoxy group which has 1 to 20 carbon atoms and may have a substituent, an alicyclic hydrocarbon group which has 3 to 20 carbon atoms and may have a substituent, a monovalent aromatic hydrocarbon group which has 6 to 20 carbon atoms and may have a substituent, a halogen atom, a cyano group, a nitro group, —$NR_{12}R_{13}$, or $SR_{12}$, where, $Z_1$ and $Z_2$ may be bonded to each other to form an aromatic hydrocarbon ring which may have a substituent or an aromatic heterocyclic ring which may have a substituent, and $R1_2$ and $R_{13}$ each independently represent a hydrogen atom or an alkyl group having 1 to 6 carbon atoms.

$A_1$ and $A_2$ each independently represent a group selected from the group consisting of —O—, —$NR_{21}$— (where $R_{21}$ represents a hydrogen atom or a substituent), —S—, and —C(=O)—; and X represents O, S, C to which a hydrogen atom or a substituent is bonded, or N to which a hydrogen atom or a substituent is bonded.

Ax represents an organic group which has 1 to 30 carbon atoms and has at least one aromatic ring selected from the group consisting of an aromatic hydrocarbon ring and an aromatic heterocyclic ring; and Ay represents a hydrogen atom, an alkyl group which has 1 to 6 carbon atoms and may have a substituent, or an organic group which has 1 to 30 carbon atoms and has at least one aromatic ring selected from the group consisting of an aromatic hydrocarbon ring and an aromatic heterocyclic ring, where, the aromatic ring included in Ax and Ay may have a substituent, and Ax and Ay may be bonded to each other to form a ring that may have a substituent.

$Q_2$ represents a hydrogen atom or an alkyl group which has 1 to 6 carbon atoms and may have a substituent.

The symbol * indicates a binding position with $L_1$ or $L_2$.

Regarding definitions and preferable ranges of respective substituents in General Formulas 2-1 to 2-4, descriptions of $Y^1$, $Q^1$, and $Q^2$ which relate to a compound (A) described in JP2012-021068A can be respectively referred to for $Y_1$, $Z_1$, and $Z_2$; descriptions of $A_1$, $A_2$, and X which relate to a compound represented by General Formula (I) described in JP2008-107767A can be respectively referred to for $A_1$, $A_2$, and X; descriptions of $A^x$, $A^y$, and $Q^1$ which relate to a compound represented by General Formula (I) described in WO2013/018526A can be respectively referred to for Ax, Ay, and $Q_2$ of General Formula 2-3; and descriptions regarding $A^a$, $A^b$, and $Q^{11}$ which relate to a compound represented by General Formula (II) described in WO2013/018526A can be respectively referred to for Ax, Ay, and $Q_2$ of General Formula 2-4. Regarding $Z_3$, a description of $Q^1$ relating to a compound (A) described in JP2012-021068A can be referred to.

X in General Formula 2-2 is preferably C to which two substituents are bonded, and both $A_1$ and $A_2$ are preferably —S—. In General Formula 2-3, as a ring in a case where Ax and Ay are bonded to each other to form a ring which may have a substituent, the ring is preferably an alicyclic hydrocarbon ring, an aromatic hydrocarbon ring, or an aromatic heterocyclic ring, and is more preferably an aromatic heterocyclic ring. In General Formula 2-4, as a ring in a case where Ax and Ay are bonded to each other to form a ring which may have a substituent, the ring is preferably an unsaturated hydrocarbon ring.

Ar in General Formula 1 is preferably an aromatic ring group represented by General Formula 2-2.

The aromatic ring group represented by General Formula 2-2 is particularly preferably an aromatic ring group represented by General Formula 2-2-1.

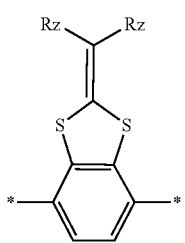

General Formula 2-2-1

In formula, Rz represents a substituent. Examples of substituents shown by Rz include a substituent that is shown as a substituent of $Sp_1$ to be described later, and the like. Two Rz's may be the same as or different from each other. In addition, two Rz's may be bonded to each other to form a ring. A ring formed in this case is preferably a 5-membered ring or a 6-membered ring, is more preferably a 5-membered ring or a 6-membered ring containing nitrogen or oxygen as an element constituting the ring, and is particularly preferably a ring represented by any of the following formulas.

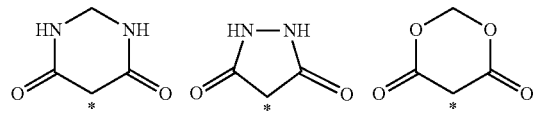

In the above formula, each * represents a position of a carbon atom to which two Rz's are bonded in General Formula 2-2-1. In addition, the ring represented by the above formula may have a substituent in nitrogen or carbon. In this case, the substituent is preferably an alkyl group having 1 to 6 carbon atoms, and is more preferably a linear alkyl group having 1 to 4 carbon atoms.

The aromatic ring group represented by General Formula 2-2-1 is preferably an aromatic ring group in which at least one Rz is a cyano group, or an aromatic ring group in which two Rz's are bonded to form a ring, and is more preferably an aromatic ring group in which two Rz's are both cyano groups.

In General Formula 1, $L_1$ and $L_2$ each independently represent a single bond, or a linking group selected from the group consisting of —O—, —S—, —C(=O)—, —OC(=O)—, —C(=O)O—, —OC(=O)O—, —NR$_{101}$C(=O)—, —C(=O)NR$_{102}$—, —OC(=O)NR$_{103}$—, —NR$_{104}$C(=O)O—, —SC(=O)—, or C(=O)S—. In the description of the above-mentioned linking group, the left side is bonded to Ar, and the right side is bonded to $Sp_1$ or $Sp_2$. $R_{101}$, $R_{102}$, $R_{103}$, and $R_{104}$ each independently represent -$Sp_3$-$Pol_3$ or a halogen atom. $L_1$ and $L_2$ each independently preferably are —O—, —OC(=O)—, —C(=O)O—, —OC(=O)O—, —NR$_{101}$C(=O)—, —C(=O)NR$_{102}$—, —OC(=O)NR$_{103}$—, or —NR$_{104}$C(=O)O—, more preferably are —O—, —OC(=O)—, —OC(=O)O—, or —OC(=O)NR$_{103}$, and even more preferably are —O—. $R_{101}$, $R_{102}$, $R_{103}$, and $R_{104}$ each independently preferably are a hydrogen atom, an alkyl group having 1 to 4 carbon atoms, or a halogen atom.

$L_1$ and $L_2$ may be the same as or different from each other, but they are preferably the same.

$Sp_1$, $Sp_2$, and $Sp_3$ each independently represent a single bond or a divalent linking group. Examples of divalent linking groups include the following linking groups, and linking groups selected from the group consisting of two or more combinations of the following linking groups.

A linear alkylene group that may have a substituent; a cycloalkylene group that may have a substituent (for example, a trans-1,4-cyclohexylene group); a divalent aromatic hydrocarbon group that may have a substituent (for example, a 1,4-phenylene group); a divalent aromatic heterocyclic group that may have a substituent; —O—; —S—; —C(=O)—; —OC(=O)—; —C(=O)O—; —OC(=O)O; —NR$_{201}$C(=O)—; —C(=O)NR$_{202}$—; —OC(=O)NR$_{203}$—; —NR$_{204}$C(=O)O—; —SC(=O)—; and —C(=O)S—.

Examples of $Sp_1$, $Sp_2$, and $Sp_3$ which are divalent linking groups include a linear alkylene group that may have a substituent; a cycloalkylene group that may have a substituent; a divalent aromatic hydrocarbon group that may have a substituent; a divalent aromatic heterocyclic group that may have a substituent; two or more linking groups which are selected from the group consisting of a linear alkylene group that may have a substituent, a cycloalkylene group that may have a substituent, a divalent aromatic hydrocarbon group that may have a substituent, and a divalent aromatic heterocyclic group that may have a substituent, and which are bonded via a linking group selected from the group consisting of a single bond, —O—, —C(=O)—, —OC(=O)—, —C(=O)O—, —OC(=O)O—, —NR$_{201}$C(=O)—, and —C(=O)NR$_{202}$—; and the like.

In the description of the linking group, the left side is bonded to L$_1$, L$_2$, or N (in the case of Sp$_3$), and the right side is bonded to Pol$_1$, Pol$_2$, or Pol$_3$.

R$_{201}$, R$_{202}$, R$_{203}$, R$_{204}$ each independently represent -Sp$_4$-Pol$_4$ or a halogen atom. Sp$_4$ and Pol$_4$ each are synonymous with Sp$_3$ and Pol$_3$, and their preferable ranges are also the same. R$_{201}$, R$_{202}$, R$_{203}$, and R$_{204}$ each independently preferably are a hydrogen atom, an alkyl group having 1 to 4 carbon atoms, or a halogen atom.

A substituent referred to in the case of referring to the phrase "may have a substituent" regarding the substituents in Sp$_1$, Sp$_2$, Sp$_3$, and General Formulas 2-1 to 2-4 is not particularly limited. Examples thereof include an alkyl group, a cycloalkyl group, an alkoxy group, an acyl group, an acyloxy group, an alkoxycarbonyl group, an amide group, an amino group, a halogen atom, a nitro group, and a cyano group, and a substituent selected from the group consisting of groups composed of a combination of two or more substituents among the above-mentioned substituents. The substituent may be a group represented by -Sp$_5$-Pol$_5$. Sp$_5$ and Pol$_5$ each are synonymous with Sp$_1$ and Pol$_1$, and their preferable ranges are also the same. The number of substituents is not particularly limited, and 1 to 4 substituents may be present. In a case where there are two or more substituents, the two or more substituents may be the same as or different from each other.

It is preferable that the divalent linking groups represented by Sp$_1$ and Sp$_2$ each independently represent a linking group selected from the group consisting of a linear alkylene group which has 1 to 30 carbon atoms and may have a substituent and a group in which one or two or more non-adjacent —CH$_2$—'s are substituted by —O—, —S—, —C(=O)—, —OC(=O)—, —C(=O)O—, —OC(=O)O—, —NR$_{201}$C(=O)—, —C(=O)NR$_{202}$—, —OC(=O)NR$_{203}$—, —NR$_{204}$C(=O)O—, —SC(=O)—, or —C(=O)S— in a linear alkylene group which has 2 to 30 carbon atoms and may have a substituent. As described above, by using a compound in which Sp$_1$ and Sp$_2$ are linking groups not having a cyclic group in the main chain, the birefringence Δn (587 nm) of the cured product is easily adjusted to 0.00≤Δn (587 nm)≤0.01.

Sp$_1$ and Sp$_2$ may be the same as or different from each other, but they are preferably the same.

In Sp$_1$ and Sp$_2$ which are groups in which —CH$_2$— is substituted with other divalent groups selected from the group consisting of —O—, —S—, —C(=O)—, —OC(=O)—, —C(=O)O—, —OC(=O)O—, —NR$_{201}$C(=O)—, —C(=O)NR$_{202}$—, —OC(=O)NR$_{203}$—, —NR$_{204}$C(=O)O—, —SC(=O)—, and —C(=O)S— in a linear alkylene group having 2 to 30 carbon atoms, it is preferable that the other substituted divalent group be not directly bonded to L$_1$ or L$_2$. That is, a site substituted by the other divalent group is preferably not an L$_1$ side terminal of Sp$_1$, and an L$_2$ side terminal of Sp$_2$.

It is more preferable that the divalent linking groups represented by Sp$_1$ and Sp$_2$ each independently represent a linking group selected from the group consisting of a linear alkylene group which has 1 to 20 carbon atoms and may have a substituent and a group in which one or two or more non-adjacent —CH$_2$—'s are substituted by —O—, —C(=O)—, —OC(=O)—, —C(=O)O—, —OC(=O)O—, —NR$_{201}$C(=O)—, —C(=O)NR$_{202}$—, —OC(=O)NR$_{203}$—, or —NR$_{204}$C(=O)O— in a linear alkylene group which has 2 to 20 carbon atoms and may have a substituent. It is even more preferable that the divalent linking groups represented by Sp$_1$ and Sp$_2$ each independently represent a linking group selected from the group consisting of a linear alkylene group which has 1 to 10 carbon atoms and may have a substituent and a group in which one or two or more non-adjacent —CH$_2$—'s are substituted by —O—, —C(=O)—, —OC(=O)—, or —C(=O)O— in a linear alkylene group which has 2 to 10 carbon atoms and may have a substituent. It is particularly preferable that the divalent linking groups represented by Sp$_1$ and Sp$_2$ each independently represent a linking group selected from the group consisting of a linear alkylene group which has 1 to 10 carbon atoms and which has no substituent or has a methyl group as a substituent and a group in which one or two or more non-adjacent —CH$_2$—'s are substituted by —O—, —C(=O)—, —OC(=O)—, or —C(=O)O— in a linear alkylene group which has 2 to 10 carbon atoms and which has no substituent or has a methyl group as a substituent.

The divalent linking group represented by Sp$_3$ is preferably a single bond or a linear alkylene group which has 1 to 10 carbon atoms and may have a substituent, is more preferably a linear alkylene group which has 1 to 5 carbon atoms and may have a substituent, is even more preferably a linear alkylene group which has 1 to 3 carbon atoms and may have a substituent, and is particularly preferably an unsubstituted linear alkylene group.

Pol$_1$, Pol$_2$, and Pol$_3$ each independently represent a hydrogen atom or a polymerizable group. Examples of polymerizable groups include polymerizable groups represented by Formulas Pol-1 to Pol-6.

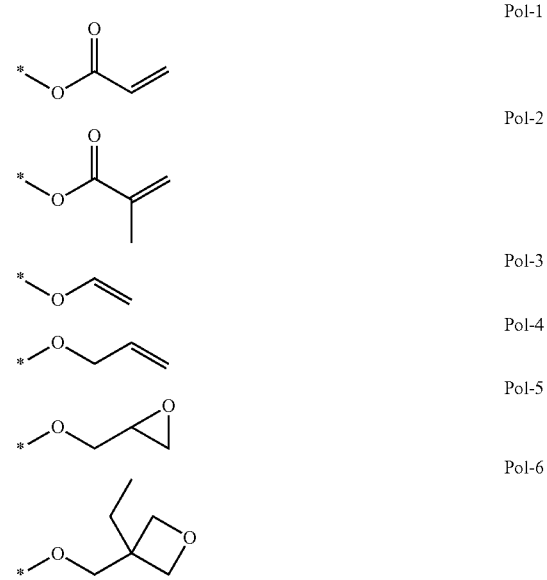

The symbol * indicates a binding position.

Among them, (meth)acryloyloxy groups (Pol-1, Pol-2) are preferable.

It is preferable that any one of the polymerizable groups Pol$_1$ or Pol$_2$ be a (meth)acryloyloxy group, and it is more preferable that both be (meth)acryloyloxy groups.

Pol$_1$ and Pol$_2$ may be the same as or different from each other, but they are preferably the same.

The compound represented by General Formula 1 has at least one polymerizable group. The compound represented by General Formula 1 preferably has at least two polymerizable groups.

-Sp$_3$-Pol$_3$ and -Sp$_4$-Pol$_4$ each independently preferably are a hydrogen atom or an alkyl group which has 1 to 4 carbon atoms or which may have a substituent, and more preferably are a hydrogen atom or an alkyl group having 1 to 4 carbon atoms.

Examples of specific structures of Pol$_1$-Sp$_1$-L$_1$- or Pol$_2$-Sp$_2$-L$_2$- include the following structures.

Pol$_1$-Sp$_1$-L$_1$- or Pol$_2$-Sp$_2$-L$_2$- may be the same as or different from each other, but they are preferably the same.

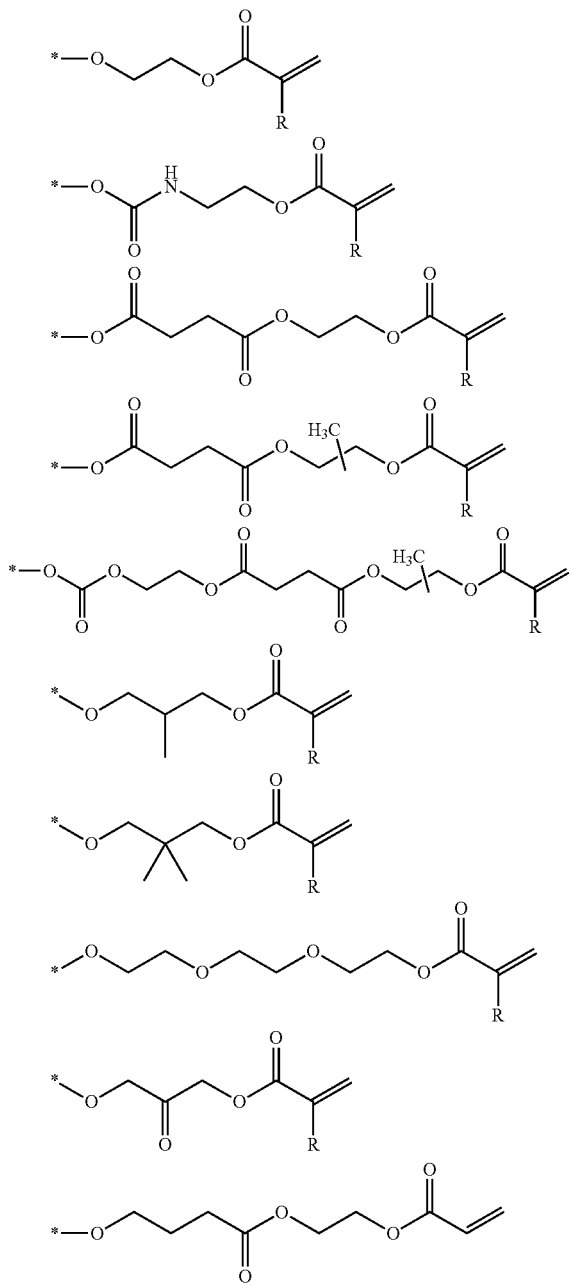

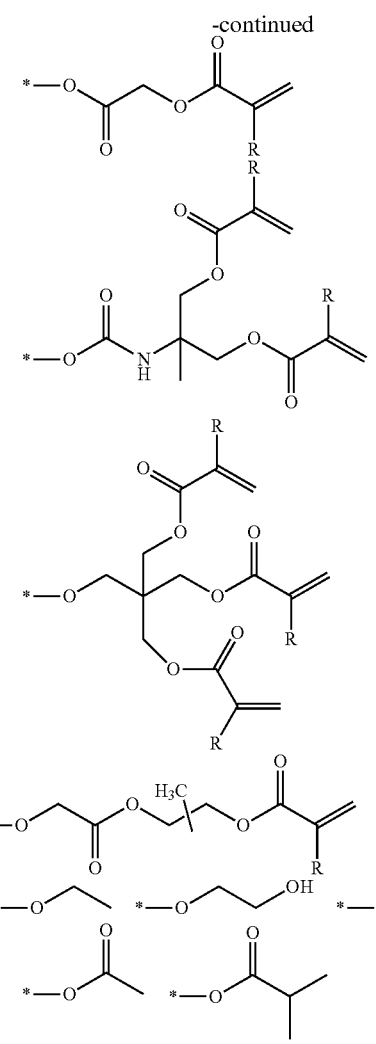

(R represents a hydrogen atom or a methyl group, and * represents a binding position with Ar.)

In the present specification, the following structure shows mixture of two partial structures of which methyl groups are respectively bonded to any one carbon of an ethylene group.

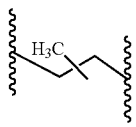

As described above, in a case where the compound represented by General Formula 1 has a structure in which a substituent is substituted on a linear alkylene group, structural isomers having different substitution positions of the substituent may be present. The compound represented by General Formula 1 may be a mixture of such structural isomers.

The compound represented by General Formula 1 is preferably a non-liquid crystalline compound.

Specific examples of the compound represented by General Formula 1 which is preferably used in the curable composition of the embodiment of the present invention are listed below, but the compounds are not limited to the following compounds. In the following structural formulas, Me represents a methyl group, Et represents an ethyl group, nPr represents an n-propyl group, iPr represents an isopropyl group, nBu represents an n-butyl group, and tBu represents a t-butyl group.
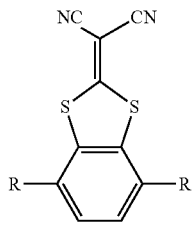
R =
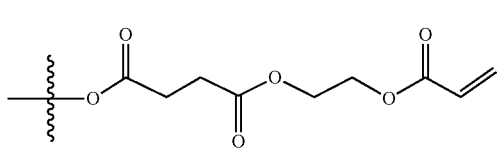 (I-1)
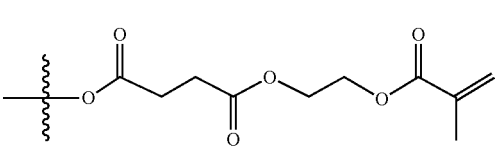 (I-2)
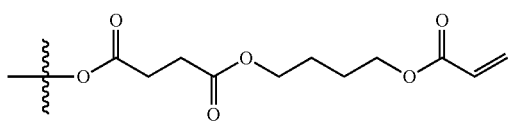 (I-3)
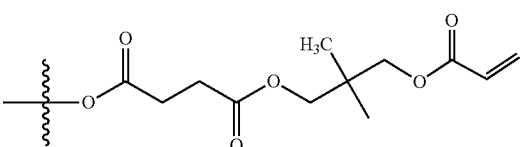 (I-4)
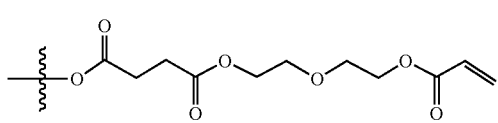 (I-5)
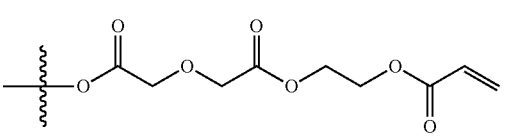 (I-6)
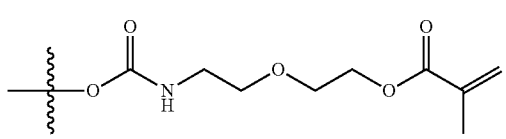 (I-7)
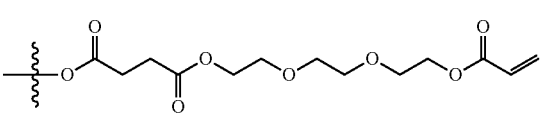 (I-8)
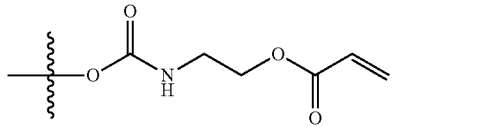 (I-9)
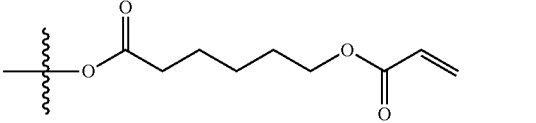 (I-10)
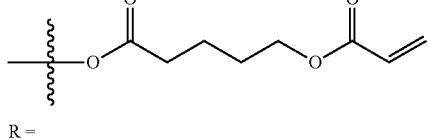 (I-11)
R =
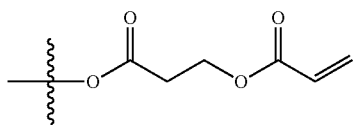 (I-12)
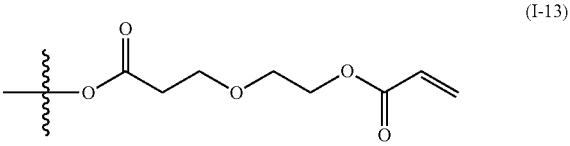 (I-13)
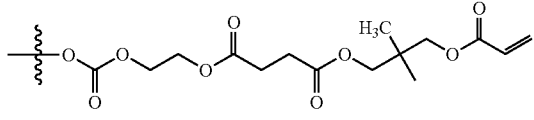 (I-14)
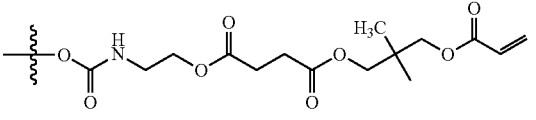 (I-15)

-continued

-continued
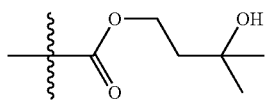
(III-7)
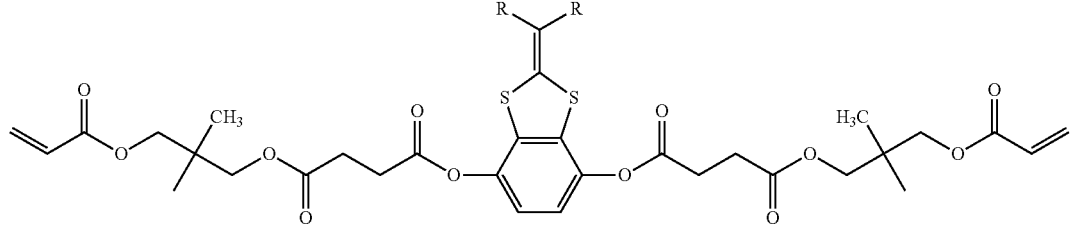
R =
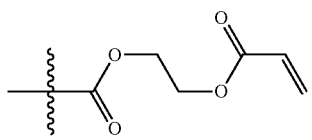 (III-8)  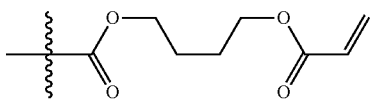 (III-9)
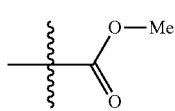 (III-10)  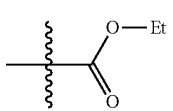 (III-11)
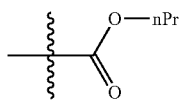 (III-12)  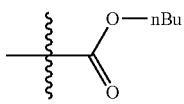 (III-13)
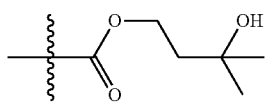 (III-14)
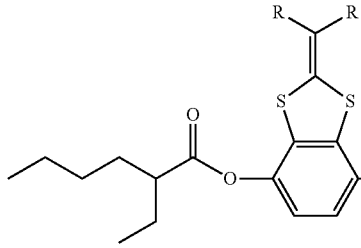
R =
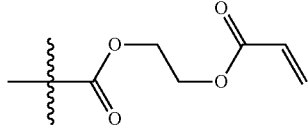 (III-15)  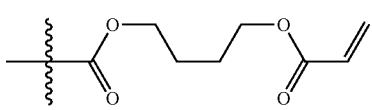 (III-16)
(III-17)
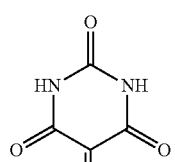
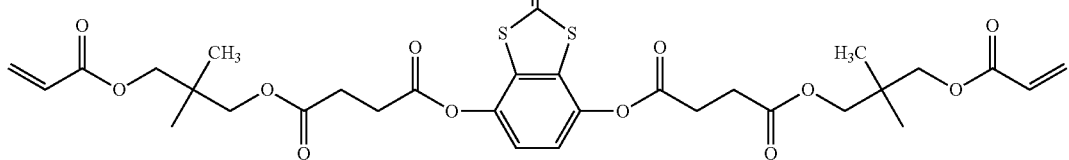

-continued
(III-18)
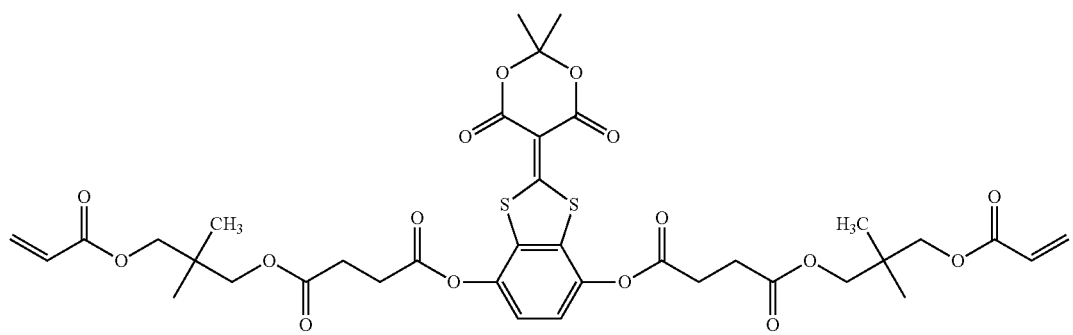
(III-19)
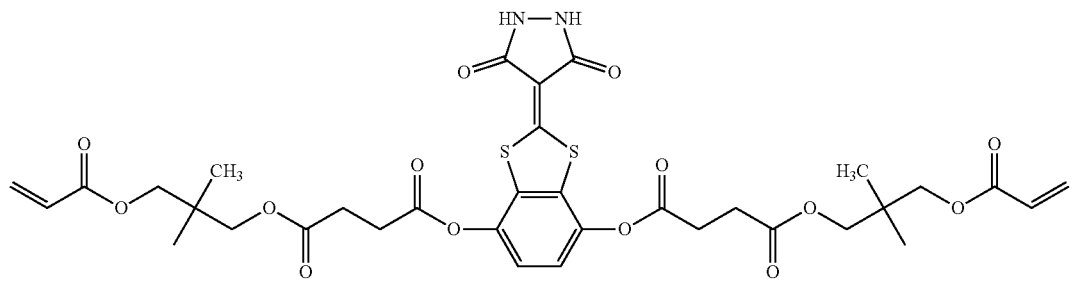
(III-20)
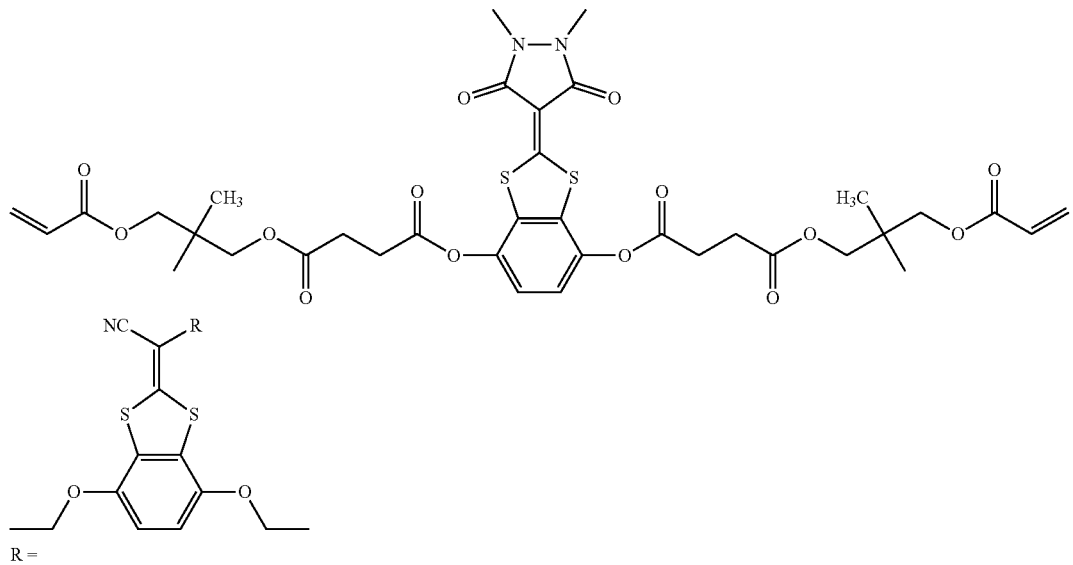
R =
(III-21)
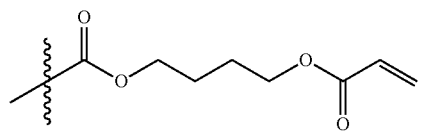
R =
(III-22)
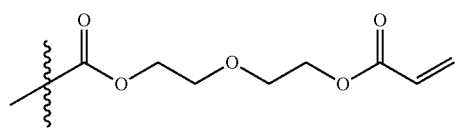
R =

-continued
(III-23)
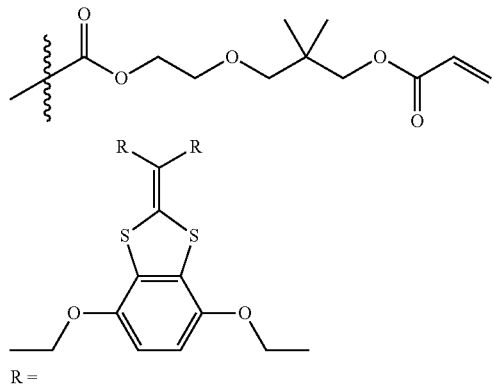
R =
(III-24)
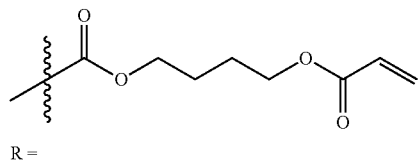
R =
(III-25)
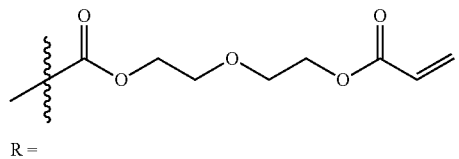
R =
(III-26)
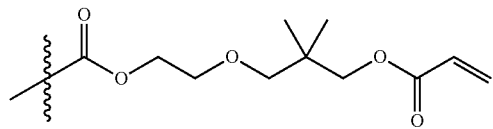
(III-27)
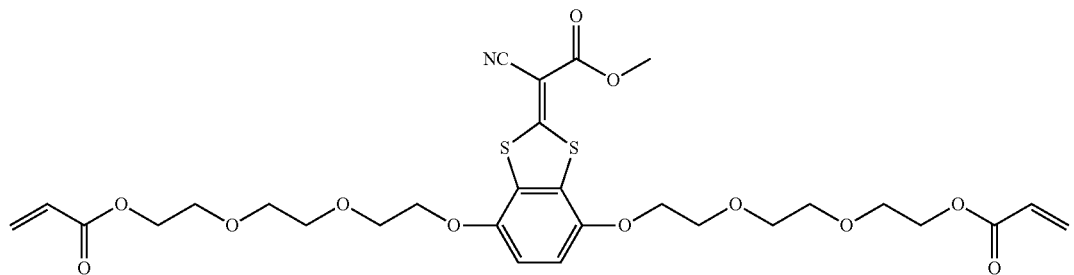
(III-28)
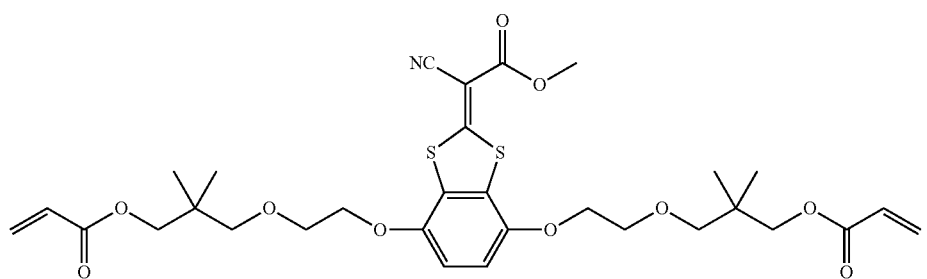

-continued
(III-29)
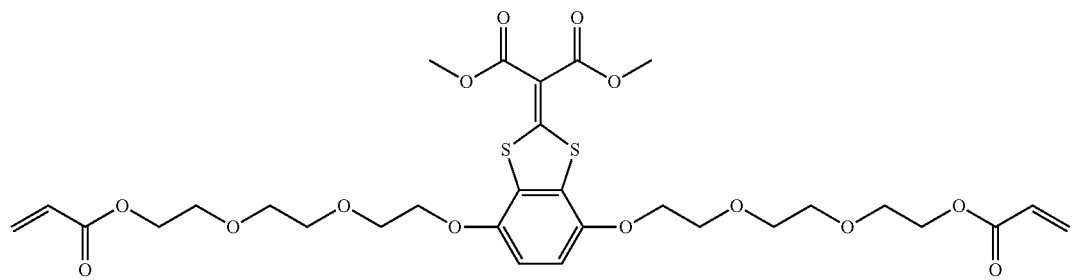
(III-30)
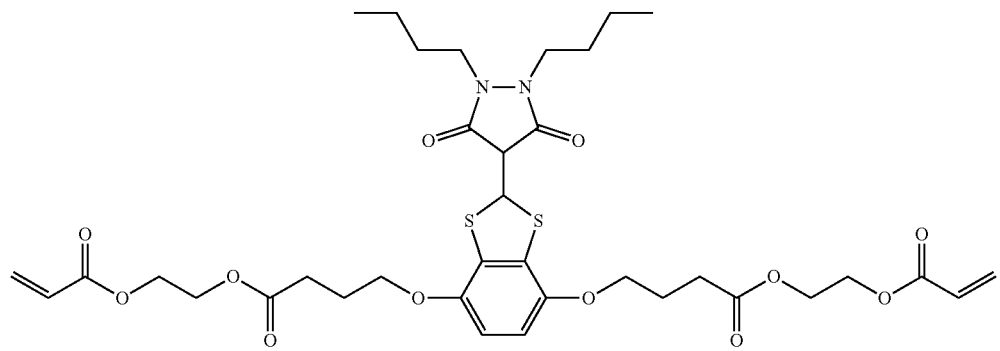
(III-31)
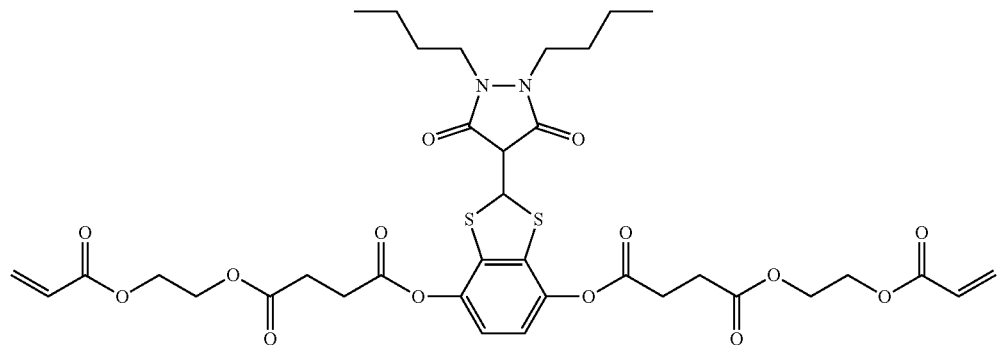
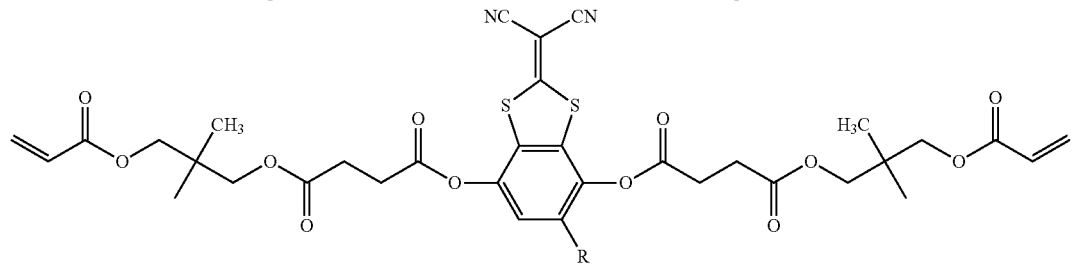
R =
(IV-1) 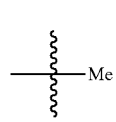  (IV-2)
(IV-3) 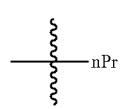  (IV-4)
(IV-5) 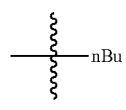  (IV-6)
R =

-continued
(IV-7)
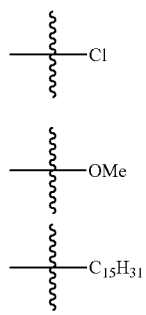
(IV-8)
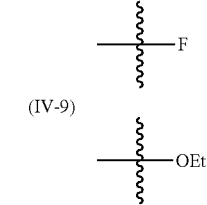
(IV-9)
(IV-10)
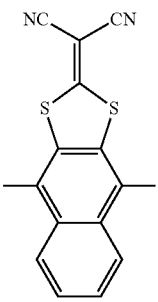
(IV-11)
(IV-12)
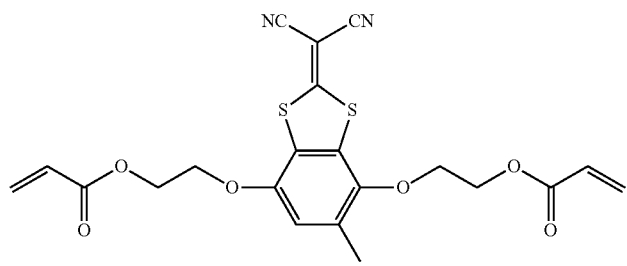
(IV-13)
(IV-14)
(IV-15)
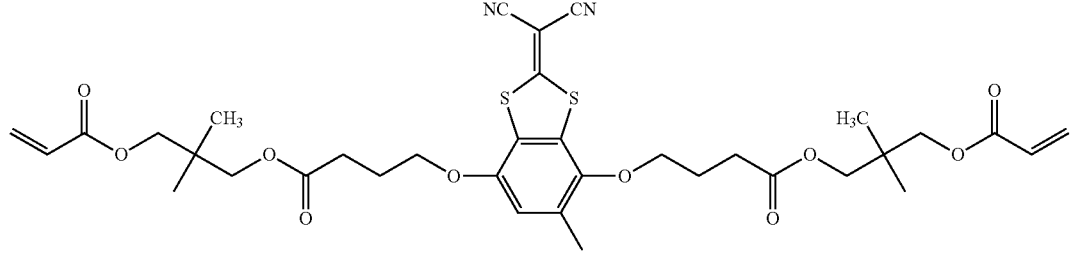
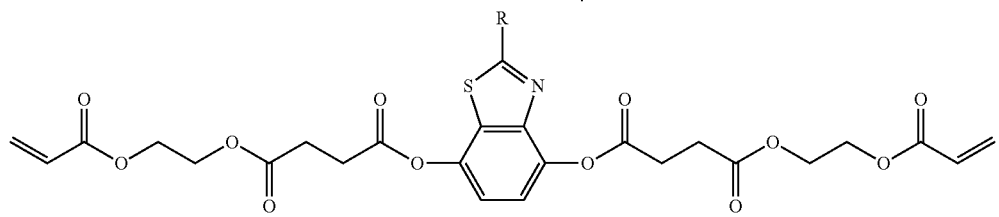
R =

-continued
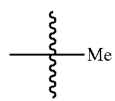
R =
(V-1)
(V-2)
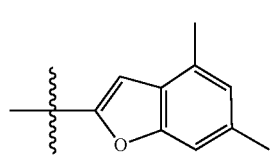
(V-3)
(V-4)
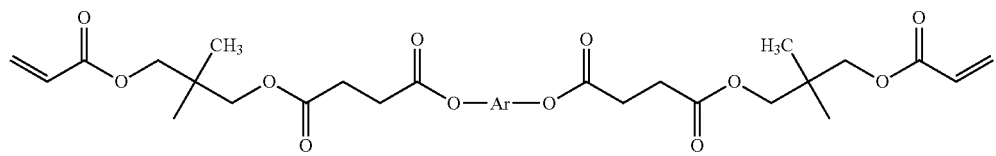
Ar =
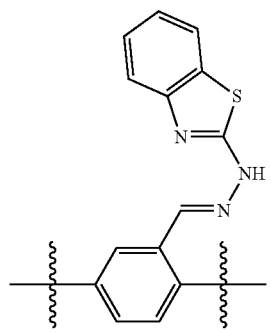
(VI-1)
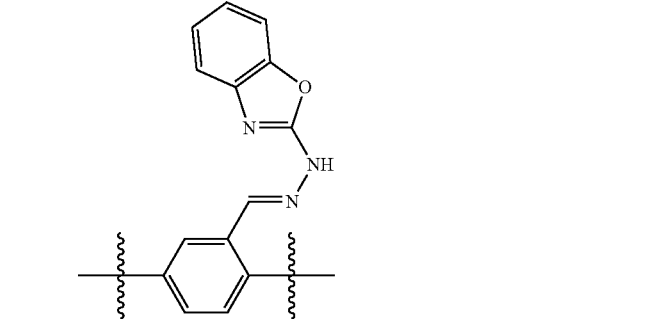
(VI-2)
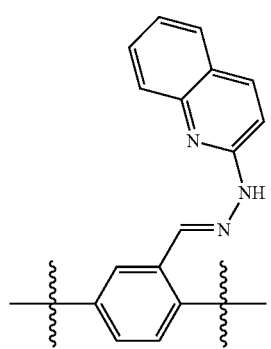
Ar =
(VI-3)
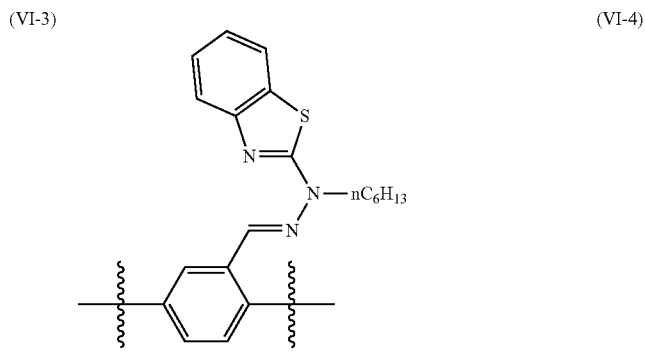
(VI-4)
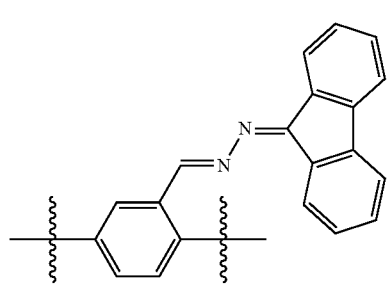
(VI-6)
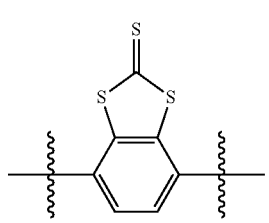
(VI-7)

The compound represented by General Formula 1 has one or two or more asymmetric carbons in some cases, and regarding stereochemistry of such asymmetric carbons, compounds represented by General Formula 1 each independently can be any of an (R) isomer or an (S) isomer. In addition, the compound represented by Formula (A) may be a mixture of stereoisomers such as optical isomers or diastereoisomers. In other words, the compound represented by Formula (A) may be any kind of stereoisomer, may be any mixture of stereoisomers, or may be a racemate.

The content of the compound represented by General Formula 1 in the curable composition is preferably 5% to 99% by mass, is more preferably 20% to 99% by mass, is even more preferably 25% to 98% by mass, and is particularly preferably 30% to 96% by mass with respect to the total mass of the curable composition. In a case where the content of the compound represented by General Formula 1 is within the above-mentioned range, a partial dispersion ratio ($\theta g, F$) higher than a predicted partial dispersion ratio ($\theta g, F$) is easily achieved in a cured product having a predetermined Abbe number.

Two or more compounds represented by General Formula 1 may be contained in the curable composition. In a case where two or more compounds represented by General Formula 1 are contained, the total content thereof is preferably within the above range.

<Other Components>

The curable composition may further contain other components in addition to the compound represented by General Formula 1. Specific examples of other components include at least one selected from (meth)acrylate monomers, photoradical polymerization initiators, or thermal radical polymerization initiators.

[(Meth)Acrylate Monomer]

The curable composition may contain a (meth)acrylate monomer. The (meth)acrylate monomer may be a polyfunctional (meth)acrylate monomer having two or more (meth)acryloyl groups in a molecule, or may be a monofunctional (meth)acrylate monomer having one (meth)acryloyl group in a molecule. Specific examples of (meth)acrylate monomers include a monomer 1 (phenoxyethyl acrylate), a monomer 2 (benzyl acrylate), a monomer 3 (tricyclodecane dimethanol diacrylate), and a monomer 4 (dicyclopentanyl acrylate) which shown below; a (meth)acrylate monomer described in paragraphs 0037 to 0046 of JP2012-107191A; and the like. A molecular weight of the (meth)acrylate monomer is preferably 100 to 500.

Monomer 1

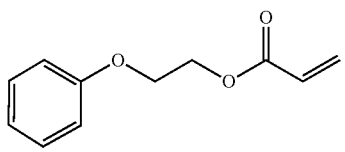

Monomer 2

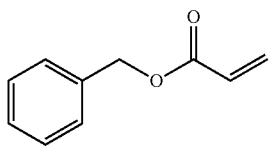

Monomer 3

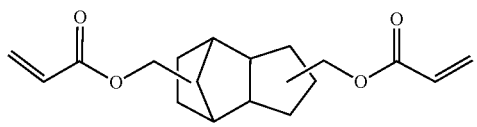

Monomer 4

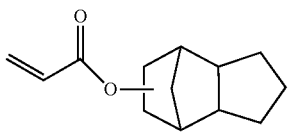

The method of obtaining the (meth)acrylate monomer is not particularly limited, and the compound may be commercially available or may be produced by synthesis. In a case of commercially obtaining the compound, for example, VISCOAT #192 PEA (Monomer 1) (manufactured by Osaka Organic Chemical Industry Ltd.), VISCOAT #160 BZA (Monomer 2) (manufactured by Osaka Organic Chemical Industry Ltd.), A-DCP (Monomer 3) (manufactured by Shin-Nakamura Chemical Co., Ltd.), or FA-513AS (Monomer 4) (manufactured by Hitachi Chemical Co., Ltd.) may be preferably used.

In addition, in a case where it is necessary to improve hardness and rub resistance of a surface of the cured product, the curable composition preferably contains a polyfunctional (meth)acrylate monomer having three or more (meth)acryloyl groups in a molecule. By incorporating a polyfunctional (meth)acrylate monomer having three or more (meth)acryloyl groups in a molecule, crosslink density of a cured product can be effectively improved, and thereby surface hardness and rub resistance can be increased while maintaining a high partial dispersion ratio. The upper limit of the number of (meth)acryloyl groups in a polyfunctional (meth)acrylate monomer having three or more (meth)acryloyl groups in a molecule is not particularly limited, but it is preferably 8 and is more preferably 6. In a case of commercial purchase, for example, A-TMPT (a monomer 5), A-TMMT (a monomer 6), AD-TMP (a monomer 7), and A-DPH (a monomer 8) (manufactured by Shin-Nakamura Chemical Co., Ltd.) can be preferably used.

Monomer 5

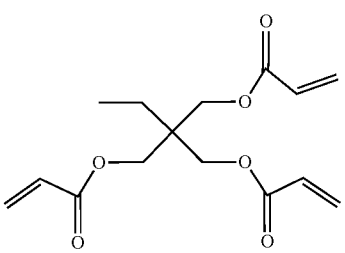

Monomer 6

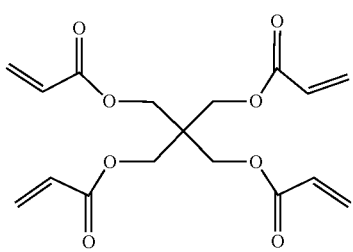

Monomer 7

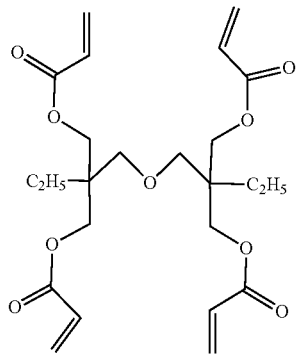

Monomer 8

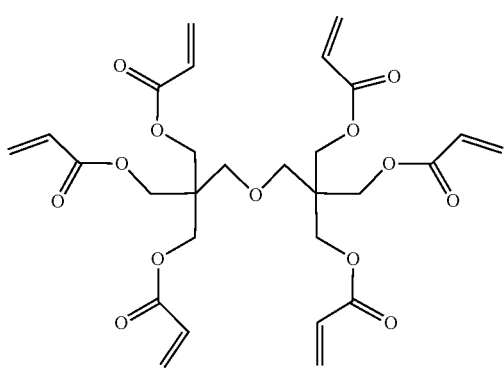

In a case where the curable composition of the embodiment of the present invention contains a (meth)acrylate monomer, the content of the (meth)acrylate monomer is preferably 1% to 80% by mass, more preferably 2% to 50% by mass, and still more preferably 3% to 40% by mass, with respect to the total mass of the curable composition. By adjusting an amount of (meth)acrylate monomer in the curable composition, a function of a cured product to relieve stress at the time of heat change can be adjusted.

In particular, in a case where it is necessary to increase hardness and rub resistance of a surface of a cured product, in the curable composition, a content of a polyfunctional (meth)acrylate monomer having three or more (meth)acryloyl groups in a molecule is preferably 5% to 95% by mass, is more preferably 10% to 80% by mass, and is even more preferably 25% to 70% by mass with respect to a total mass of the curable composition. In this case, a content of the compound represented by General Formula 1 in the curable composition is preferably 5% to 95% by mass, is more preferably 20% to 95% by mass, and is even more preferably 30% to 75% by mass with respect to the total mass of the curable composition. Such a composition can be used as a composition for forming a hard coat.

[Polymer Having Radically Polymerizable Group in Side Chain]

The curable composition containing the compound represented by General Formula 1 may further contain a polymer having a radically polymerizable group in a side chain, in addition to the above-described compound. Because the polymer having a radically polymerizable group in a side chain functions to increase a viscosity of the curable composition, it can also be called a thickener or a thickening polymer. The polymer having a radically polymerizable group in a side chain can be added for adjusting a viscosity of the curable composition.

The polymer having a radically polymerizable group in the side chain may be a homopolymer or a copolymer. Among them, it is preferable that the polymer which has a radically polymerizable group in a side chain be a copolymer. When the polymer having a radically polymerizable group in the side chain is a copolymer, it is sufficient that at least one copolymer component has a radically polymerizable group. In addition, in a case where the polymer having a radically polymerizable group in the side chain is a copolymer, the thickening polymer is more preferably a copolymer containing a monomer unit having a radically polymerizable group in the side chain and a monomer unit having an aryl group in the side chain.

Examples of radically polymerizable groups include a (meth)acrylate group, a vinyl group, a styryl group, and an allyl group. The polymer having a radically polymerizable group in the side chain preferably contains 5% to 100% by mass, more preferably 10% to 90% by mass, and even more preferably 20% to 80% by mass of repeating units having a radically polymerizable group.

In the following, specific examples of the polymer having a radically polymerizable group in the side chain preferably used in the present invention are exemplified, but the polymer having a radically polymerizable group in the side chain is not limited to the following structure. Each of the specific examples shown below is a copolymer, and each copolymer includes two or three structural units illustrated adjacent thereto. For example, the specific example described at the top is an allyl methacrylate-benzyl methacrylate copolymer.

In the structural formulas below, Ra and Rb each independently represent hydrogen or a methyl group. Note that a plurality of Ra's in one polymer may be the same or different. n represents an integer of 0 to 10, preferably 0 to 2, and more preferably 0 or 1.

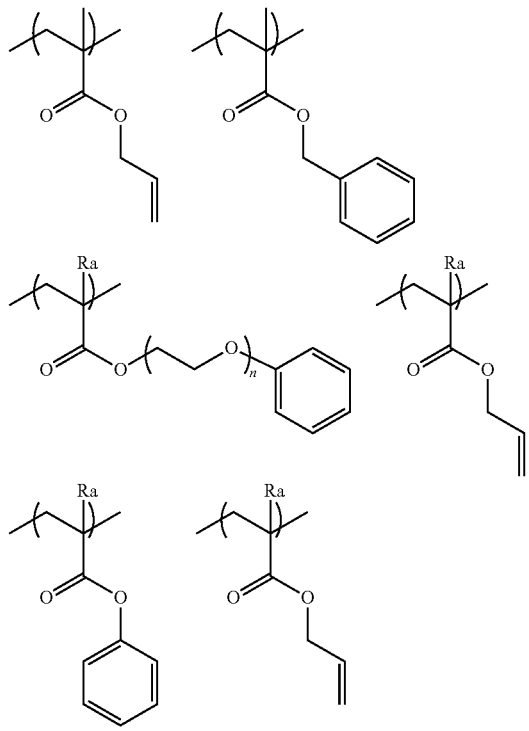

37
-continued
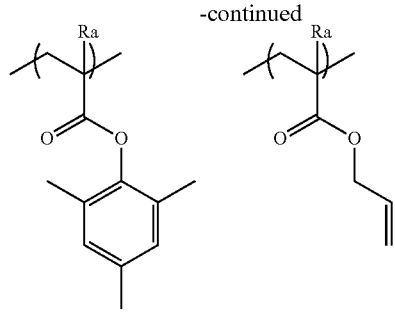
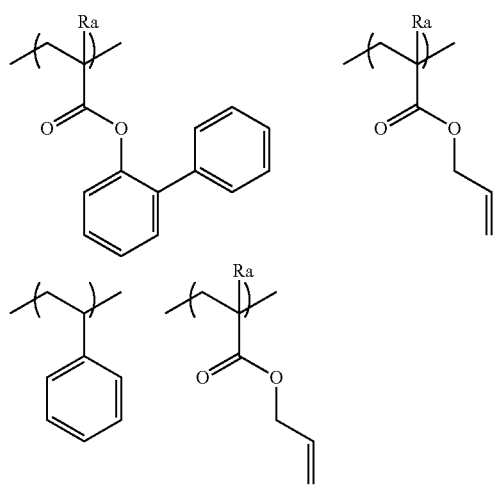
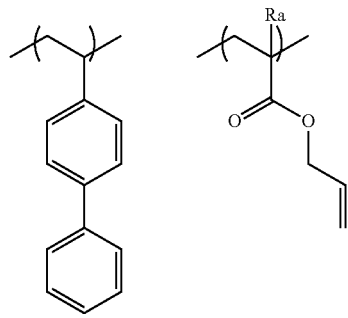
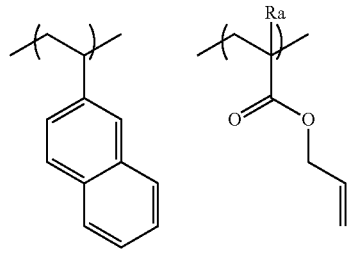
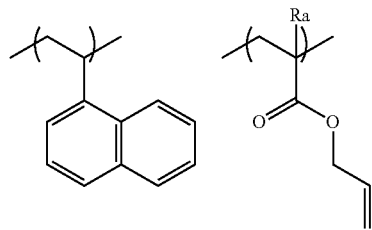
38
-continued
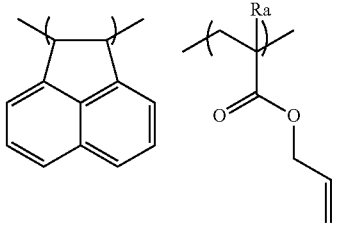
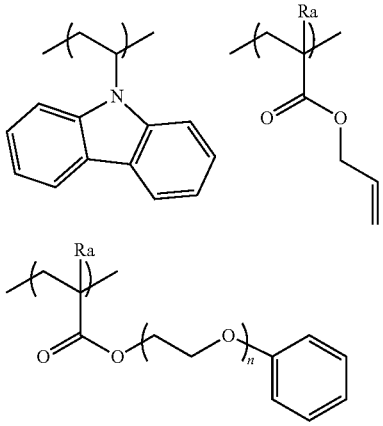
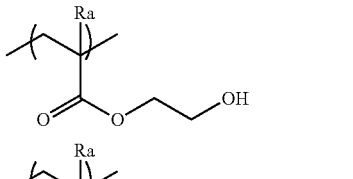
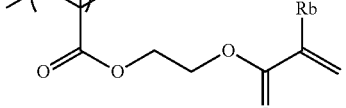
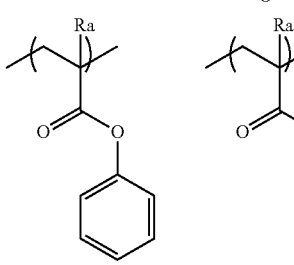
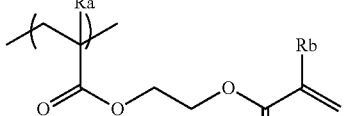
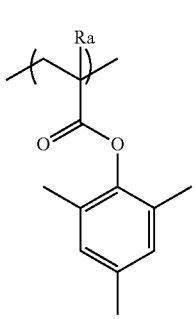

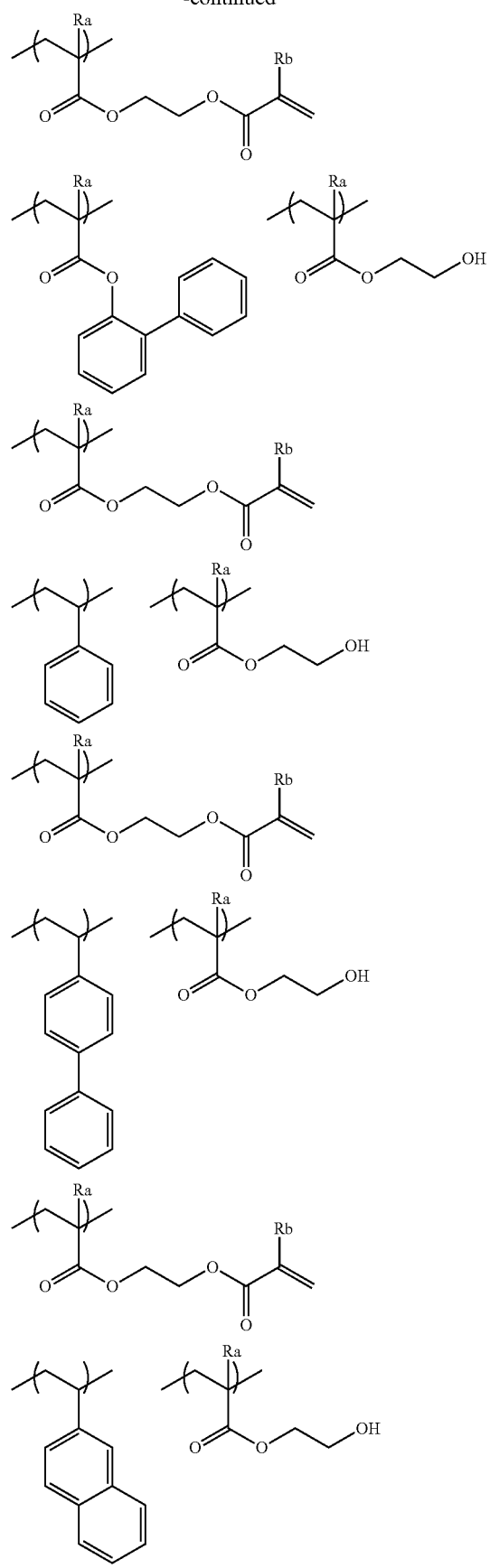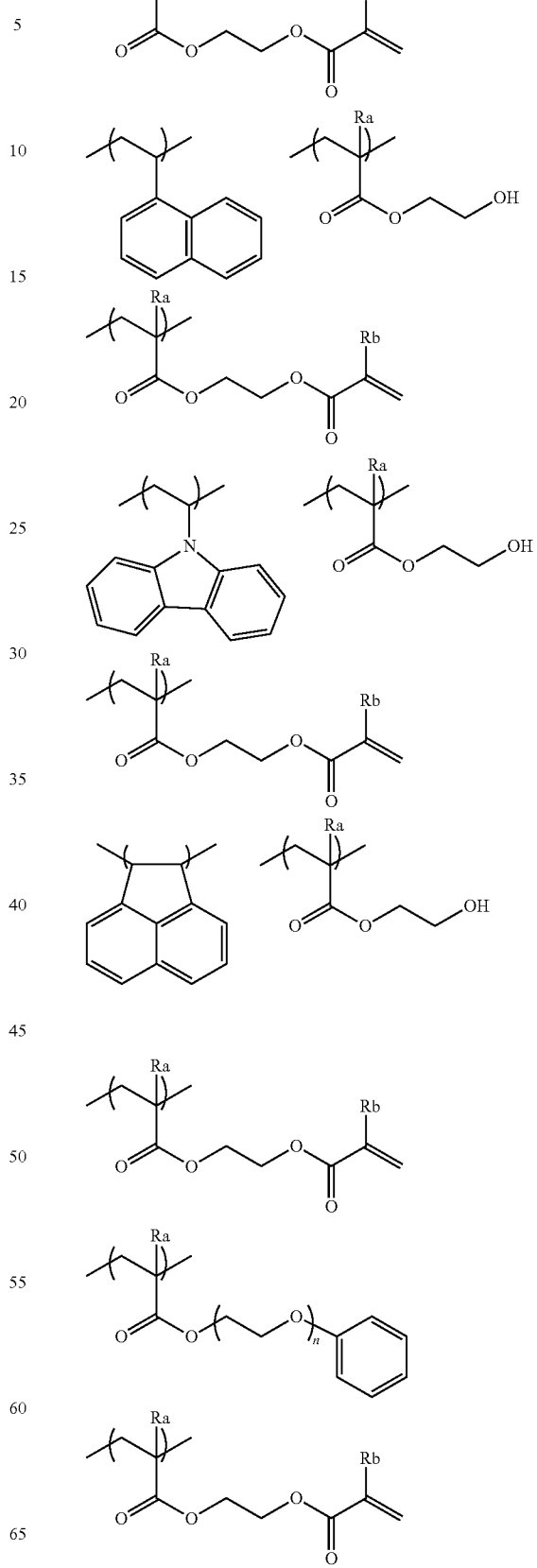

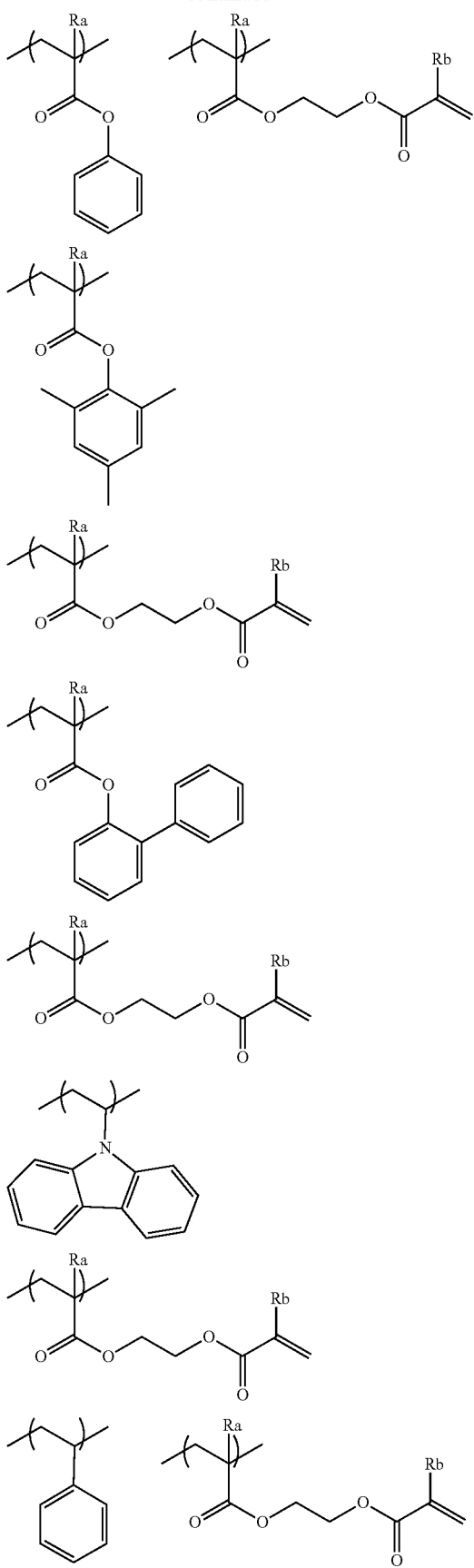
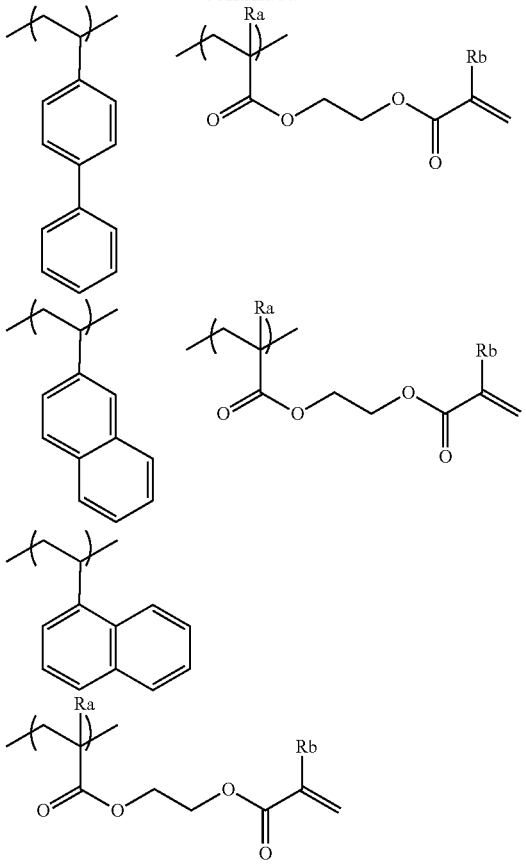

The molecular weight (weight-average molecular weight) of the polymer having a radically polymerizable group in the side chain is preferably 1,000 to 10,000,000, more preferably 5,000 to 300,000, and even more preferably 10,000 to 200,000. The glass transition temperature of the polymer having a radically polymerizable group in the side chain is preferably 50° C. to 400° C., more preferably 70° C. to 350° C., and even more preferably 100° C. to 300° C.

The content of the polymer having a radically polymerizable group in the side chain is preferably 40% by mass or less, more preferably 30% by mass or less, and even more preferably 25% by mass or less with respect to the total mass of the curable composition. The content of the polymer having a radically polymerizable group in the side chain may be 0% by mass, and an aspect in which a polymer having a radically polymerizable group in the side chain is not added is also preferable.

[Polymerization Initiator]

The curable composition containing the compound represented by General Formula 1 preferably contains at least one selected from a photoradical polymerization initiator or a thermal radical polymerization initiator.

(Thermal Radical Polymerization Initiator)

The curable composition preferably contains a thermal radical polymerization initiator. By this action, it is possible to mold a cured product having high heat resistance by thermally polymerizing the curable composition.

Specifically, the following compounds can be used as the thermal radical polymerization initiator. Examples of the thermal radical polymerization initiator include 1,1-di(t-hexylperoxy)cyclohexane, 1,1-di(t-butylperoxy)cyclohexane, 2,2-di(4,4-di-(t-butylperoxy)cyclohexyl)propane, t-hexylperoxyisopropyl monocarbonate, t-butylperoxy-3,5,5-trimethylhexanoate, t-butylperoxy laurate, dicumyl peroxide, di-t-butyl peroxide, t-butylperoxy-2-ethylhexanoate, t-hexylperoxy-2-ethylhexanoate, cumene hydroperoxide, t-butyl hydroperoxide, t-butylperoxy-2-ethylhexyl, 2,3-dimethyl-2,3-diphenylbutane, and the like.

The content of the thermal radical polymerization initiator is preferably 0.01% to 10% by mass, more preferably 0.05% to 5.0% by mass, and still more preferably 0.05% to 2.0% by mass, with respect to the total mass of the curable composition.

(Photoradical Polymerization Initiator)

The curable composition preferably contains a photoradical polymerization initiator. Specifically, the following compounds can be used as the photoradical polymerization initiator. Examples of the photoradical polymerization initiator include bis(2,6-dimethoxybenzoyl)-2,4,4-trimethylpentylphosphine oxide, bis(2,6-dimethylbenzoyl)-2,4,4-trimethylpentylphosphine oxide, bis(2,4,6-trimethylbenzoyl)-2,4,4-trimethylpentylphosphine oxide, bis(2,6-dichlorobenzoyl)-2,4,4-trimethylpentylphosphine oxide, 1-phenyl-2-hydroxy-2-methylpropan-1-one, 1-hydroxycyclohexyl phenyl ketone, 1-(4-isopropylphenyl)-2-hydroxy-2-methylpropan-1-one, 1,2-diphenylethanedione, methylphenyl glyoxylate, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)butanone-1,2,4,6-trimethylbenzoyl-diphenyl-phosphine oxide, and bis(2,4,6-trimethylbenzoyl)-phenylphosphine oxide.

Of the above, in the present invention, BASF's IRGACURE 184 (1-hydroxycyclohexyl phenyl ketone), IRGACURE 819 (bis(2,4,6-trimethylbenzoyl)-phenylphosphine oxide), IRGACURE 651 (2,2-dimethoxy-1,2-diphenylethane-1-one), 1-[4-(2-hydroxyethoxy)-phenyl]-2-hydroxy-2-methyl-1-propan-1-one, or 2-methyl-1-(4-methylthiophenyl)-2-morpholinopropan-1-one may be preferably used as the photoradical polymerization initiator.

The content of the photoradical polymerization initiator is preferably 0.01% to 5.0% by mass, more preferably 0.05% to 1.0% by mass, and still more preferably 0.05% to 0.5% by mass, with respect to the total mass of the curable composition.

The curable composition preferably contains both a photoradical polymerization initiator and a thermal radical polymerization initiator described above, and in this case, the total content of a photoradical polymerization initiator and a thermal radical polymerization initiator is preferably 0.01% to 5% by mass, more preferably 0.05% to 1.0% by mass, and still more preferably 0.05% to 0.5% by mass, with respect to the total mass of the curable composition.

(Other Additives)

Unless contrary to the gist of the present invention, the curable composition containing the compound represented by General Formula 1 may contain additives such as a polymer, a monomer, a dispersant, a plasticizer, a thermal stabilizer, or a mold release agent other than the components described above.

A viscosity of the curable composition containing the compound represented by General Formula 1 is preferably 20,000 mPa·s or less, is more preferably 15,000 mPa·s or less, is even more preferably 13,000 mPa·s or less, and is particularly preferably 10,000 mPa·s or less. By setting the viscosity of the curable composition within the above range, it is possible to improve handleability in a case of molding a cured product, thereby forming a high-quality cured product. A viscosity of the curable composition is preferably 2,000 mPa·s or more, is more preferably 3,000 mPa·s or more, is even more preferably 4,000 mPa·s or more, and is particularly preferably 5,000 mPa·s or more.

<Method for Manufacturing Cured Product>

The method for manufacturing a cured product includes a step of photocuring the above-described curable composition and/or a step of thermosetting. Among them, a method for manufacturing a cured product preferably includes a step of forming a semi-cured product by irradiating the curable composition with light or heating the curable composition; and a step of forming a cured product by irradiating the obtained semi-cured product with light or heating the semi-cured product.

[Step of Forming Semi-Cured Product]

The step of forming a semi-cured product preferably includes a transfer step. A transfer step is a step of pressing a mold against the curable composition mentioned above. In the transfer step, the other mold is pressed against the curable composition injected into one of the pair of molds to spread the curable composition.

It is preferable that the mold used with the manufacturing method of cured products is a mold subjected to a chromium nitride treatment. Thereby, a favorable mold releasability can be obtained in a release step to be performed the subsequent steps, and the manufacture efficiency of the optical member can be increased.

Examples of chromium nitride treatment include a method of forming a chromium nitride film on the mold surface. Examples of methods for forming a chromium nitride film on the mold surface include a Chemical Vapor Deposition (CVD) method and a Physical Vapor Deposition (PVD) method. The CVD method is a method of forming a chromium nitride film on a substrate surface by reacting a source gas containing chromium and a source gas containing nitrogen at a high temperature. The PVD method is a method of forming a chromium nitride film on the surface of the substrate using an arc discharge (arc type vacuum deposition method). Specifically, the arc type vacuum deposition method can be performed by the following procedure. A cathode (evaporation source) made of chromium, for example, is placed in the vacuum vessel, an arc discharge is caused between the cathode and the wall of the vacuum vessel via a trigger, ionization of the metal based on arc plasma is performed at the same time as vaporizing the cathode. On the other hand, a negative voltage is applied to the substrate, and about several tens of mTorr (1.33 Pa) of a reaction gas (for example, a nitrogen gas) is put into the vacuum vessel. Thereby, the ionized metal and the reaction gas are reacted on the surface of the substrate to form a compound film.

In the present invention, the chromium nitride treatment on the mold surface is performed by the CVD method or the PVD method.

In general, the mold can be heated while pressing the contents by combining two molds. In a case where a low viscosity composition is injected into the mold, leakage into the mold clearance is caused. For this reason, it is preferable that the curable composition inject into a mold has a certain viscosity or more. In order to adjust the viscosity of the curable composition, a polymer having the above-described radically polymerizable group in the side chain may be added to the curable composition.

After the step of pressing the mold, a step of forming a semi-cured product is performed. The semi-cured product can be obtained by semi-curing the curable composition injected into the mold. In the step of forming the semi-cured product, light irradiation or heating is performed. In the present specification, such a step can also be called a semi-curing step.

In the semi-curing step, the curable composition according to the embodiment of the present invention is subjected to at least one of light irradiation or heating. In semi-curing, there is generally no difference in Abbe number and partial dispersion ratio (θg, F) of a finally obtained cured product, regardless of whether light irradiation is performed or heating is performed. In the semi-curing step, it is preferable to form a semi-cured product having a complex viscosity of $10^5$ to $10^8$ mPa·s at 25° C. and a frequency of 10 Hz.

As used herein, the term "semi-cured product" in the present specification refers to a product obtained by polymerizing a curable composition, which is not completely solid and has fluidity to some extent. A polymer of a curable composition in such a state that its complex viscosity at 25° C. and at a frequency of 10 Hz is $10^5$ to $10^8$ mPa·s is a semi-cured product. That is, those of which the upper limit value of the complex viscosity at 25° C. and at a frequency of 10 Hz is less than $1.0 \times 10^9$ mPa·s are considered to fall within a range of semi-cured products. On the other hand, the term "cured product" refers to a product produced by curing a curable composition by polymerization and is in a state of being completely solid.

The light used in the photoirradiation is preferably ultraviolet light or visible light and more preferably ultraviolet light. For example, a metal halide lamp, a low pressure mercury lamp, a high pressure mercury lamp, an ultrahigh pressure mercury lamp, a germicidal lamp, a xenon lamp, or a light emitting diode (LED) light source lamp is suitably used. The atmosphere during photoirradiation is preferably air or an inert gas purged atmosphere and is more preferably an atmosphere purged with nitrogen until an oxygen concentration becomes 1% or less.

In a case of providing a heating and semi-curing step in the semi-curing step, the semi-curing by heating is carried out so that the complex viscosity of the semi-cured product at 25° C. and at a frequency of 10 Hz after heating is preferably $10^5$ to $10^8$ mPa·s.

The present invention may relate to a semi-cured product manufactured by the above-described method. Such a semi-cured product may be preferably used for a method for manufacturing a cured product to be described later. The preferred range of the complex viscosity of the semi-cured product is the same as the preferred range of the complex viscosity of the semi-cured product in the above-described step of forming a semi-cured product.

The semi-cured product may not contain the photoradical polymerization initiator at all after the photoirradiation step, since the initiator is completely consumed in the step, or the photoradical polymerization initiator may remain in the semi-cured product.

In addition, the glass transition temperature of the semi-cured product is preferably −150° C. to 0° C., more preferably −50° C. to 0° C., and particularly preferably −20° C. to 0° C.

[Step of Forming Cured Product]

The step of forming a cured product preferably includes a thermal polymerization step of putting the semi-cured product in a molding mold for pressure deformation therein, and heating it therein for thermal polymerization to obtain a cured product or a photopolymerization step of photoirradiating the semi-cured product to obtain a cured product. In the present specification, such a step can also be called a curing step. The photoirradiation conditions and the heating conditions in the forming step of a cured product are the same as those in the semi-curing step described above.

In a case where the curing step is a thermal polymerization step, the molding mold used in the polymerization step is also referred to as a thermoforming mold. In general, the thermoforming mold is composed of two molding mold parts and is preferably designed so that contents can be heated under pressure in the combination of the two molding mold parts. In the method for producing a cured product, a metallic mold is more preferably used as the molding mold in the thermal polymerization step to obtain a cured product. The thermoforming mold of the type for use herein is described, for example, in JP2009-126011A. In addition, it is preferable that the mold is a mold subjected to a chromium nitride treatment.

In the thermal polymerization step, the semi-cured product put in a molding mold is deformed under pressure and heated for thermal polymerization to obtain a cured product. Here, pressure deforming and heating may be carried out simultaneously, or heating may be carried out after pressure deforming, or pressure deforming may be carried out after heating. Above all, preferably, pressure deforming and heating are carried out simultaneously. Also preferably, after simultaneous pressure deforming and heating, the product may be further heated at a higher temperature after the pressure applied thereto has become stable.

In the thermal polymerization step, the semi-cured product is heated and cured at a temperature of 150° C. or higher to obtain a cured product.

The heating temperature is 150° C. or higher, preferably 160° C. to 270° C., more preferably 165° C. to 250° C., and even more preferably 170° C. to 230° C.

In this curing step, it is preferable to perform heating and pressure deformation. Thereby, the inverted shape of the inner surface of the mold can be accurately transferred to the cured product.

The pressure for the pressure deforming is preferably 0.098 MPa to 9.8 MPa, more preferably 0.294 MPa to 4.9 MPa, and particularly preferably 0.294 MPa to 2.94 MPa.

The time of thermal polymerization is preferably 30 to 1,000 seconds, more preferably 30 to 500 seconds, and particularly preferably 60 to 300 seconds. The atmosphere during thermal polymerization is preferably air or an inert gas purged atmosphere and more preferably an atmosphere purged with nitrogen until an oxygen concentration becomes 1% or less.

A release step is provided after the curing step. When thermal polymerization is performed in the curing step, it is preferable that the mold is separated from the cured product in a temperature range of 150° C. to 250° C. in the mold release step. By setting the temperature in the mold release step within the above range, the mold can be easily separated from the cured product, and the manufacture efficiency can be increased.

As mentioned above, although an example of the manufacturing method of the cured product of the embodiment of the present invention was described, the structure of the present invention is not restricted thereto, and it can be suitably changed within the range which does not deviate from the present invention. For example, the mold used in the transfer step and the semi-curing step may be used as it is in the curing step; or after performing the semi-curing step, the mold may be pulled away from the semi-cured product, and the semi-cured product may be moved to another mold (thermoforming mold) to perform the curing step. In this case, it is preferable that the above-described chromium treatment is performed on the mold used in the semi-curing step and the curing step.

Furthermore, in the semi-curing step, the curable composition in the mold may be irradiated with light and heated. Thereby, the semi-cured product which has a desired degree of curing can be obtained reliably.

<Semi-Cured Product>

The semi-cured product can be formed by semi-curing the above-described curable composition. The semi-cured product is preferably a cured product produced by the above-mentioned method for producing a semi-cured product. In addition, the semi-cured product preferably has a complex viscosity of $10^5$ to $10^8$ mPa·s and a frequency of 10 Hz at 25° C.

The cured product of the embodiment of the present invention may be formed by curing the semi-cured product described above.

<Use Applications of Cured Product>

Because the cured product of the embodiment of the present invention has a low birefringence index and a high heat shock resistance, it can be used in various applications. For example, it can be used for a coating layer such as a hard coat layer.

Furthermore, the cured product of the embodiment of the present invention having a small Abbe number (vd) and a high partial dispersion ratio (θg, F) can be preferably used for an optical member.

[Optical Member]

The type of optical member is not particularly limited, but the cured product according to the embodiment of the present invention is suitably used especially for light-transmissive optical members (so-called passive optical members). Examples of optically-functional devices equipped with such optical members include various types of display devices (a liquid crystal display, a plasma display, and the like), various types of projector devices (an overhead projector (OHP), a liquid crystal projector, and the like), optical fiber communication systems (a light waveguide, a light amplifier, and the like), and image-taking devices such as a camera and a video.

Examples of the passive optical members include lenses, prisms, prism sheets, panels (plate-like molded bodies), films, optical waveguides (film-like optical waveguide, a fiber-like optical waveguide, and the like), optical discs, and LED sealants. The passive optical member may be provided with any coating layer or any additional functional layer as necessary. For example, the passive optical members may be provided with a protective layer for preventing mechanical damage of the coating surface caused by friction or abrasion, a light-absorbing layer for absorbing the light having an undesirable wavelength to cause degradation of inorganic particles, substrates and others, a blocking layer for suppressing or preventing permeation of reactive small molecules such as moisture or oxygen gas, an antiglare layer, an antireflection layer, a layer of low refractive index, or the like. Specific examples of coating layers include a transparent conductive film or gas barrier film formed of an inorganic oxide coating layer or inorganic nitride coating layer, and a gas barrier film or hard coating film formed of an organic coating layer. The coating method for forming the coating layer may be any known coating method such as a vacuum deposition method, a CVD method, a sputtering method, a dip coating method, or a spin coating method.

[Lens Substrate]

The optical member may be a lens substrate. That is, the cured product of the embodiment of the present invention may be used as a lens substrate. In the present specification, the "lens substrate" refers to a single member capable of exhibiting a lens function. The lens substrate manufactured using the cured product of the embodiment of the present invention exhibits a small Abbe number and a high partial dispersion ratio. Preferably, by suitably adjusting the type of monomer constituting the curable composition, it is possible to control the refractive index of the lens substrate in any desired manner, and furthermore, the cured product can become a lens substrate material which has high refractive property, light transmittance, and lightweight property.

On and around the surface of the lens substrate, any film and member may be provided depending on the use environment and applications of lenses. For example, a protective film, an antireflection film, a hard coating film, or the like may be formed on the surface of the lens substrate. In addition, a lens substrate manufactured using the cured product of the embodiment of the present invention can be made into a compound lens laminated with one or more other lens substrates selected from a glass lens substrate and a plastic lens substrate.

The periphery of the lens substrate may be fixed by being inserted into a substrate holding frame or the like. However, those films and frames are additional members to the lens substrate and therefore differ from the lens substrate itself referred to in the present specification.

In a case of using the lens substrate for lenses, the lens substrate itself may be used as a lens by itself, or additional films or frames or additional lens substrates may be added thereto for use as a lens, as mentioned above. The type and the shape of the lens using the lens substrate are not particularly limited, but the maximum thickness is preferably 0.1 to 10 mm. The maximum thickness is more preferably 0.1 to 5 mm and particularly preferably 0.15 to 3 mm. In addition, the lens substrate is preferably a circular shape with the maximum diameter of 1 to 1,000 mm. The maximum diameter is more preferably 2 to 200 mm and particularly preferably 2.5 to 100 mm.

The lens substrate is preferably used for, for example, lenses for imaging devices such as mobile phones or digital cameras; lenses for movie devices such as TV or video cameras; and lenses for in-vehicle devices or endoscope lenses.

EXAMPLES

Hereinafter, the features of the present invention will be more specifically described with reference to Examples and Comparative Examples. In the following Examples, the materials to be used, amounts and ratios thereof, the details of the treatment and the treatment procedures, and the like may be suitably modified or changed without departing from the scope of the present invention. Accordingly, the scope of the present invention should not be limitedly interpreted by the following specific Examples.

Synthesis Example 1

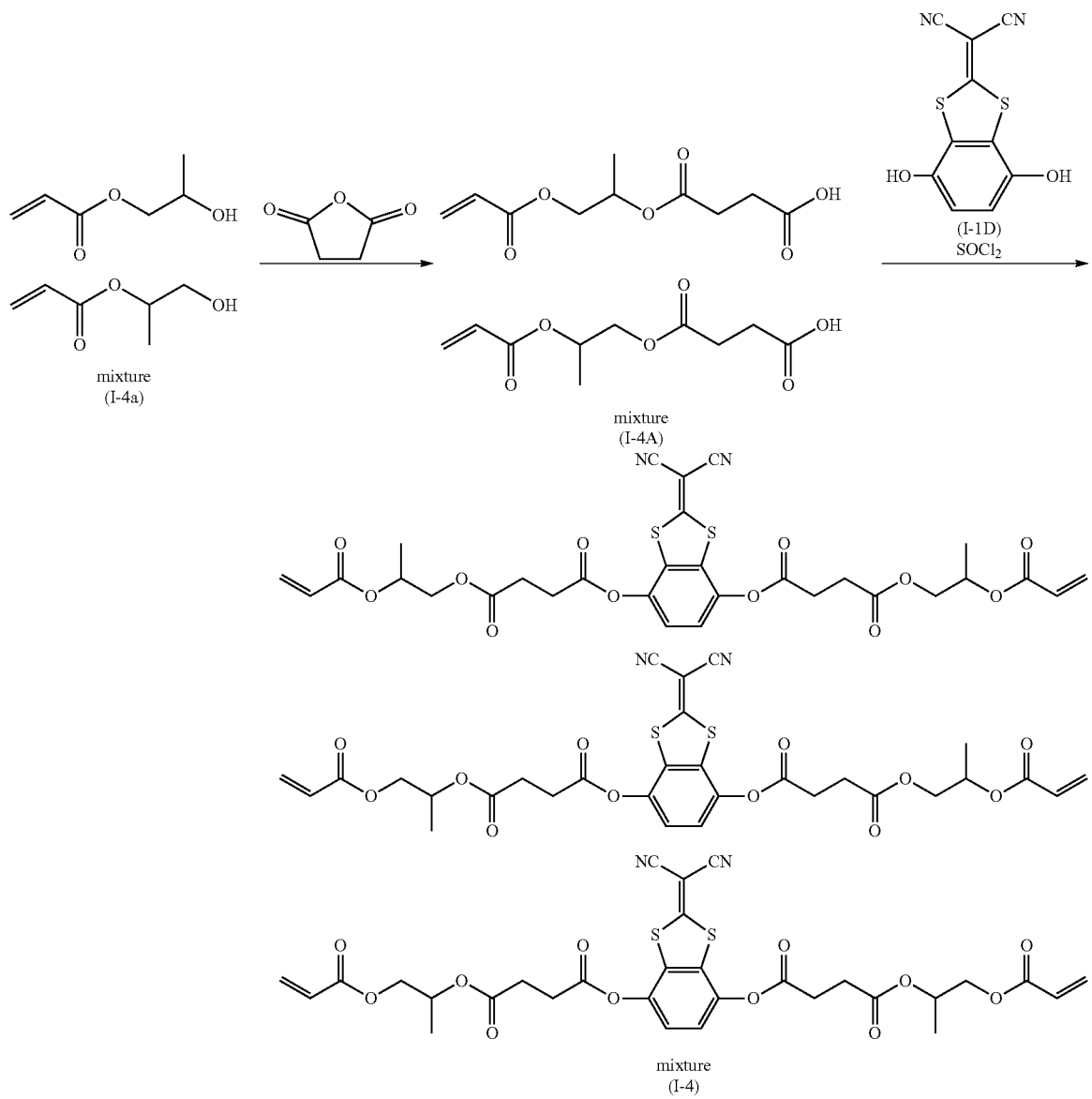

<Synthesis of Compound (I-1D)>

Synthesis of a compound (I-1D) was performed according to a method described in "Journal of Chemical Crystallography" (1997); 27 (9); 515-526.

<Synthesis of Compound (I-4A)>

A compound (I-4A) was synthesized according to a method for synthesizing a compound (I-4A) described in JP2016-081035A.

<Synthesis of Compound (I-4)>

15.5 g (67.4 mmol) of a carboxylic acid compound (I-4A), 185 mL of ethyl acetate, 46 mL of N,N-dimethylacetamide, and 60 mg of 2,6-di-t-butyl-4-methylphenol were mixed, and an internal temperature was cooled to 0° C. To the mixture, 7.75 g (65.1 mmol) of thionyl chloride was added dropwise at an internal temperature of 0° C. to 5° C. After stirring at 5° C. for 60 minutes, a solution of 6.85 g (27.6 mmol) of the compound (I-1D) and 52 mL of tetrahydrofuran (THF) was added dropwise at an internal temperature of 0° C. to 8° C.

Thereafter, 16.8 g of N,N-diisopropylethylamine was added dropwise at an internal temperature of 0° C. to 10° C. After stirring at an internal temperature of 20° C. to 25° C. for 1 hour, 40 mL of ethyl acetate, 165 mL of water, and 14 mL of concentrated hydrochloric acid were added and washed. The organic layer was washed with 140 mL of saturated saline and separated, and then washed with 100 mL of saturated saline and 10 mL of 7.5% by mass aqueous sodium bicarbonate to be separated. Thereafter, concentration was performed to obtain an oily composition, which was then purified by column chromatography, and thereby a compound (I-4) (yield 85%) was obtained.

$^1$H-NMR (400 MHz, CDCl$_3$): δ (ppm) 1.25-1.35 (d,6H), 2.78 (t,4H), 2.95 (t,4H), 4.10-4.35 (m,4H), 5.25 (sext,2H), 5.83 (d,2H), 6.05-6.15 (m,2H), 6.40 (d,2H), 7.33 (s,2H)
Synthesis Example 2
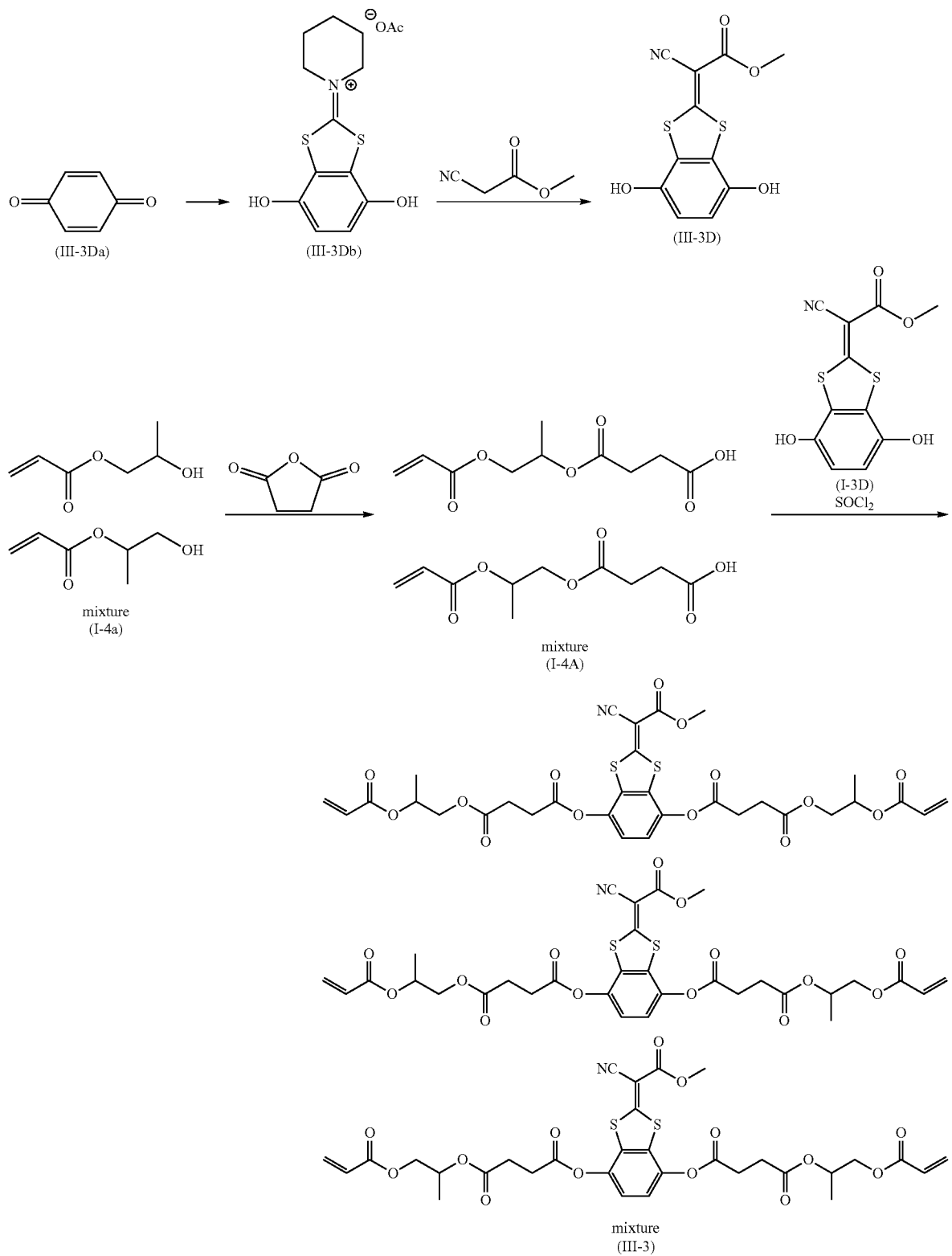

<Synthesis of Compound (III-3Db)>

Synthesis of a compound (III-3Db) was performed according to a method described in "Journal of Organic Chemistry" (2004); 69 (6); p. 2164-2177.

<Synthesis of Compound (III-3D)>

5.0 g (15.3 mmol) of the compound (III-3Db), 1.66 g (16.80 mmol) of methyl cyanoacetate, and 25 mL of isopropyl alcohol were mixed and stirred for 3 hours under heating to reflux. Thereafter, the mixture was cooled to room temperature, 50 mL of water was added to the mixture, and the precipitated crystals were filtered. The obtained crystals were washed with a mixed solution of water-isopropyl alcohol (10 to 1) and a 0.5N hydrochloric acid solution, then dissolved in N,N-dimethylacetamide and filtered. Water was added to the obtained filtrate, the precipitated crystals were filtered, and thereby 2.2 g (7.82 mmol) of a compound (III-3D) (yield 51%) was obtained.

<Synthesis of Compound (III-3)>

A compound (III-3) (yield 86%) was obtained in the same manner as in Example 1, except that the compound (I-1D) in the synthesis method of the compound (I-4) described in Example 1 was changed to the compound (III-3D).

$^1$H-NMR (400 MHz, CDCl$_3$): δ (ppm) 1.25-1.35 (d,6H), 2.78 (t,4H), 2.95 (t,4H), 3.89 (s,3H), 4.10-4.35 (m,4H), 5.25 (sext,2H), 5.83 (d,2H), 6.05-6.15 (m,2H), 6.40 (d,2H), 7.28 (s,2H)

Synthesis Example 3

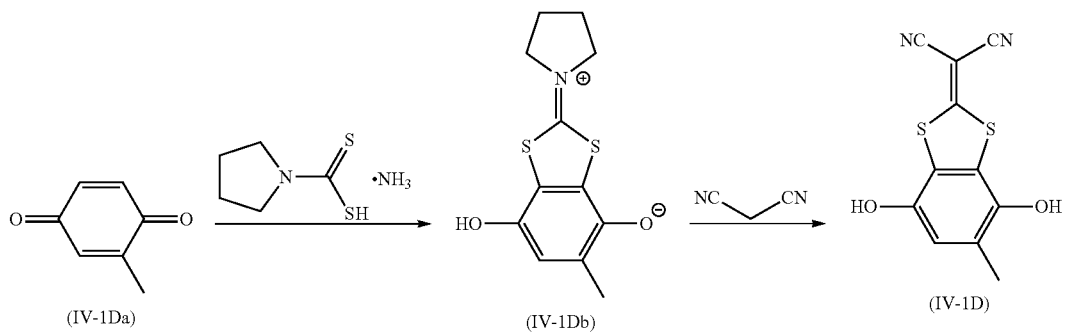

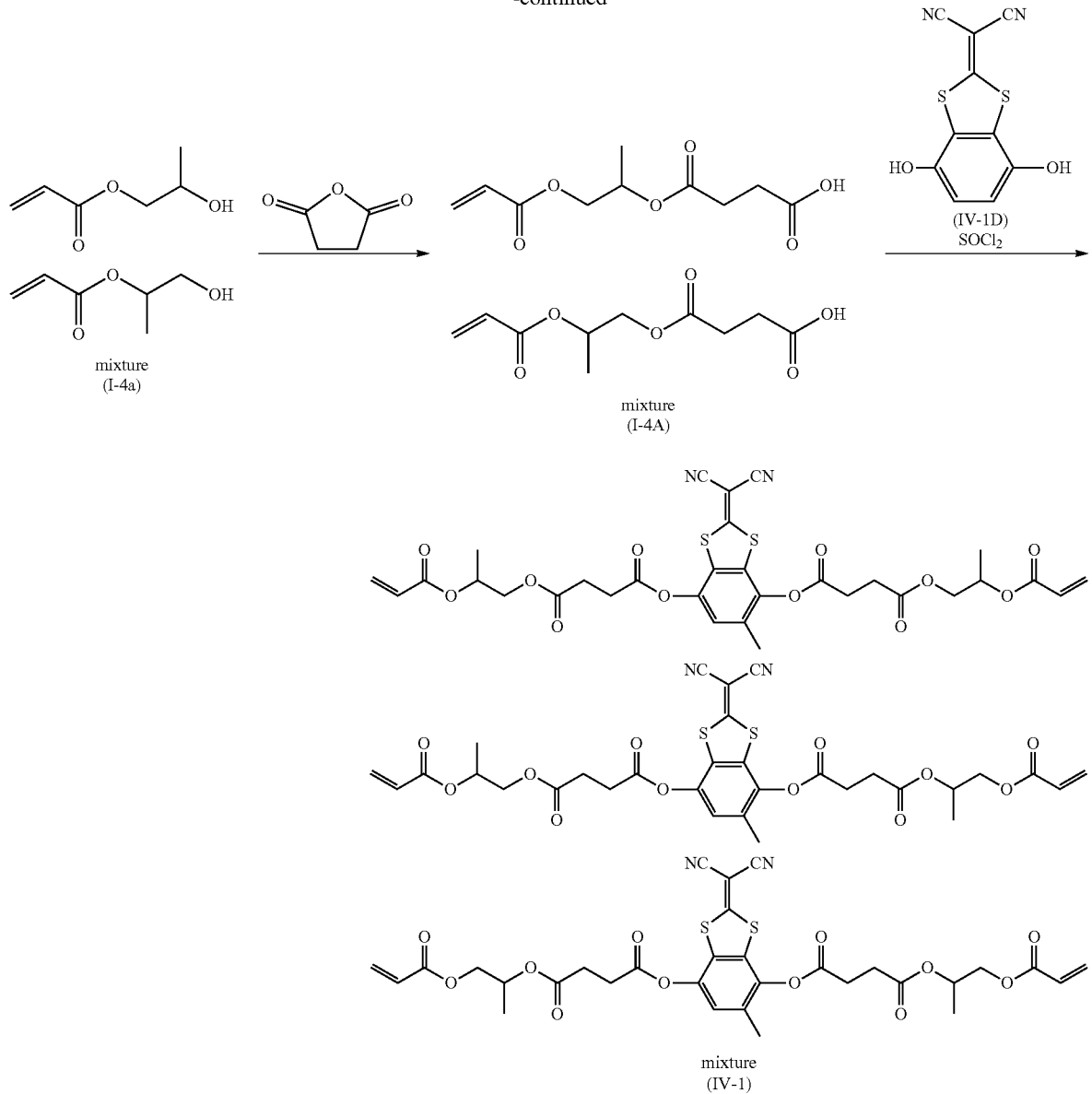

mixture (IV-1)

<Synthesis of Compound IV-1Db>

8.2 g (50.0 mmol) of 1-ammonium pyrrolidinecarbodithioate and 50 mL of N,N-dimethylformamide were mixed and cooled to 5° C. To the mixture, a solution of 6.7 g (55.0 mmol) of toluquinone (IV-1Da) in 40 mL of acetic acid was added dropwise and stirred at room temperature for 2 hours. Thereafter, the internal temperature was cooled to 5° C., and a solution of 5.9 g (55.0 mmol) of 1,4-benzoquinone in 40 mL of dimethyl sulfoxide was slowly added dropwise so that the internal temperature did not exceed 15° C. After stirring at room temperature for 1 hour, 1 L of water was added. To the mixture, 28% by mass aqueous sodium hydroxide solution was added until crystals were precipitated, the precipitated crystals were filtered and washed with water and methanol, and thereby 5.4 g (20.1 mmol) of a compound (IV-1Db) (yield 40%) was obtained.

<Synthesis of Compound IV-1D>

1.5 g (5.6 mmol) of the compound (IV-1Db), 410 mg (6.2 mmol) of malononitrile, 16 mL of isopropyl alcohol, 0.3 mL of acetic acid, and 0.2 mL of acetic anhydride were mixed, and the mixture was stirred with heating under reflux for 3 hours. Thereafter, the mixture was cooled to room temperature, water was added to the mixture, and the precipitated crystals were filtered, and thereby 1.1 g (4.2 mmol) of a compound (IV-1D) (yield 75%) was obtained.

<Synthesis of Compound IV-1>

A compound (IV-1) (yield 80%) was obtained in the same manner as in Example 1, except that the compound (I-1D) in the synthesis method of the compound (I-4) described in Example 1 was changed to the compound (IV-1D).

$^1$H-NMR (400 MHz, CDCl$_3$): δ (ppm) 1.25-1.35 (d,6H), 2.78 (m,4H), 2.95 (m,4H), 4.10-4.35 (m,4H), 5.24 (sext,2H), 5.83 (d,2H), 6.05-6.15 (m,2H), 6.40 (d,2H), 7.20 (s,2H)

Synthesis Example 4
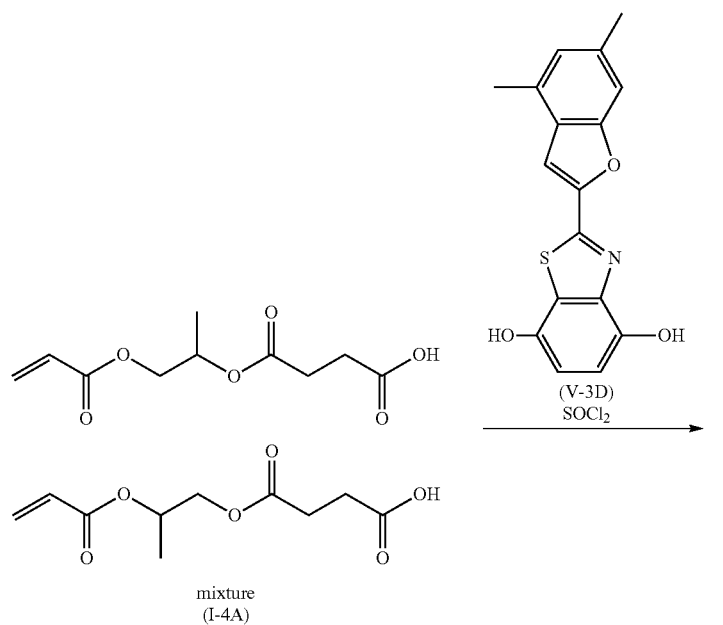
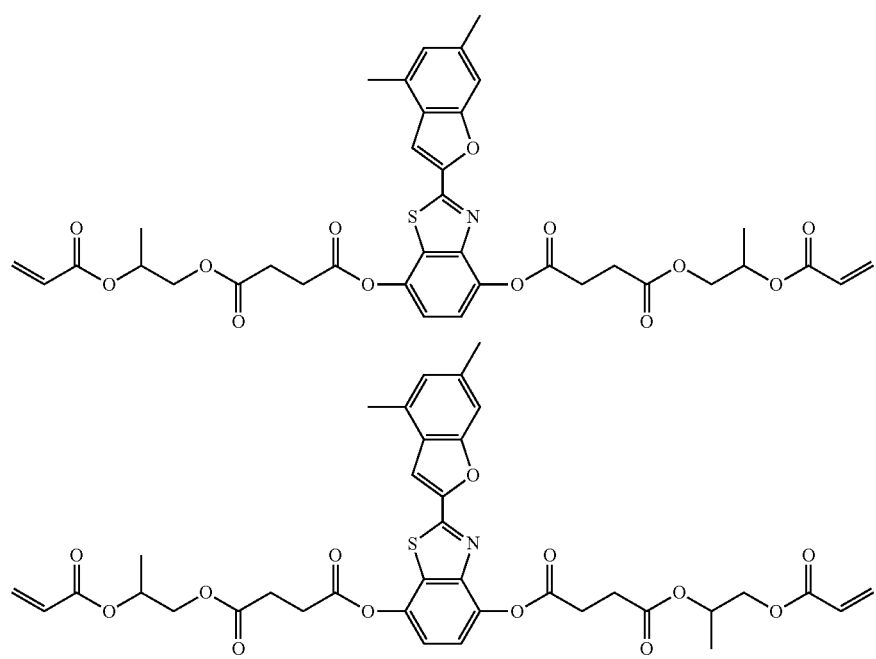

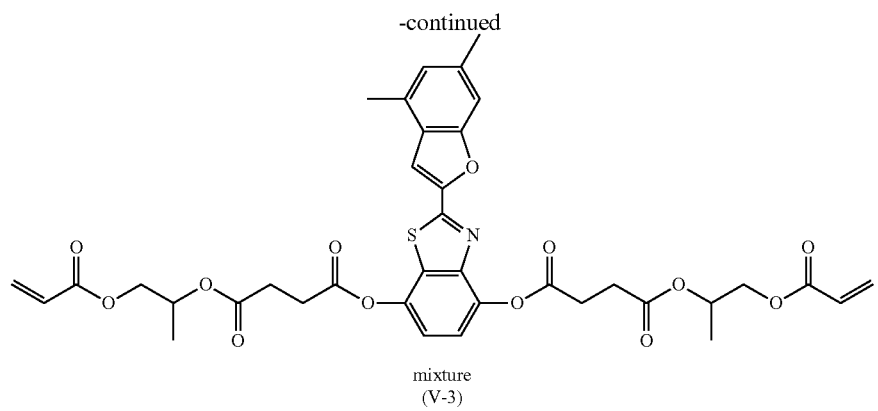

mixture
(V-3)

<Synthesis of V-3D>

A compound (V-3D) was synthesized with reference to a method for synthesizing a compound (11-d) described in paragraph 0282 of JP2013-071956A.

<Synthesis of Compound (V-3)>

A compound (V-3) (yield 82%) was obtained in the same manner as in Example 1, except that the compound (I-1D) in the synthesis method of the compound (I-4) described in Example 1 was changed to the compound (V-3D).

$^1$H-NMR (400 MHz, DMSO-d6): δ (ppm) 1.25-1.35 (d,6H), 2.78 (t,4H), 2.95 (t,4H), 4.10-4.35 (m,4H), 5.25 (sext,2H), 5.83 (d,2H), 6.05-6.15 (m,2H), 6.40 (d,2H), 7.03 (s,1H), 7.35-7.45 (m,3H), 7.80 (s,1H)

Synthesis Example 5

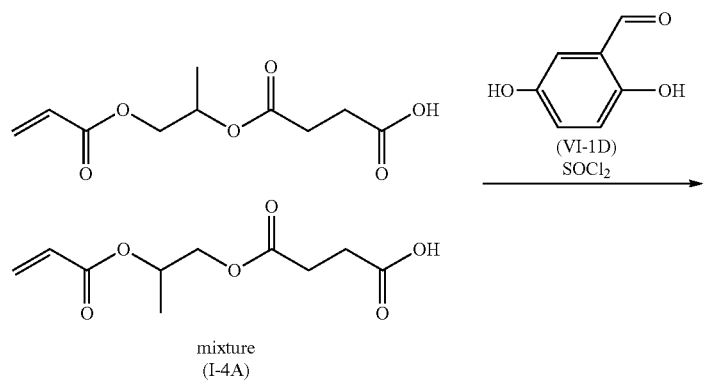

mixture
(I-4A)

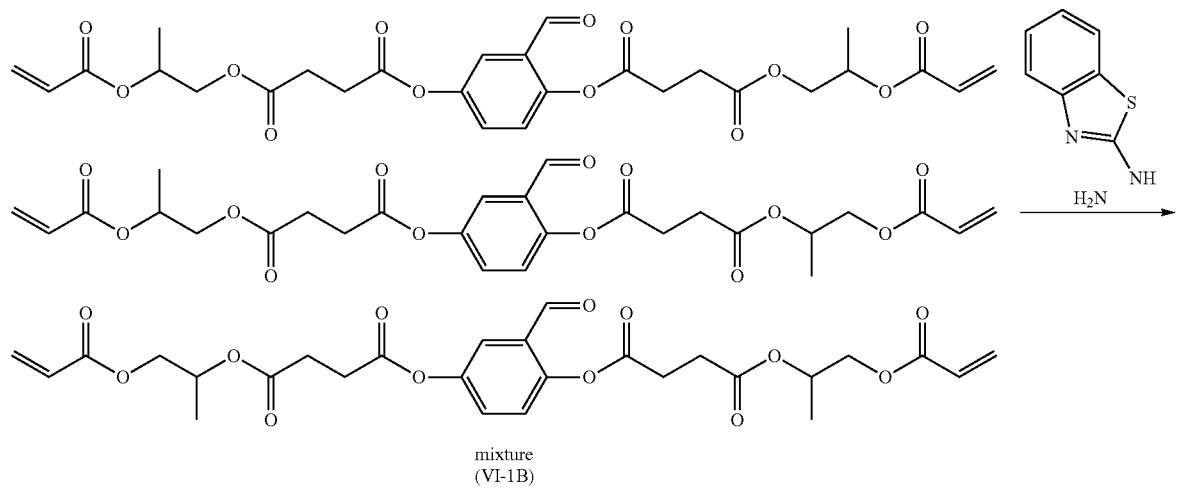

mixture
(VI-1B)

-continued

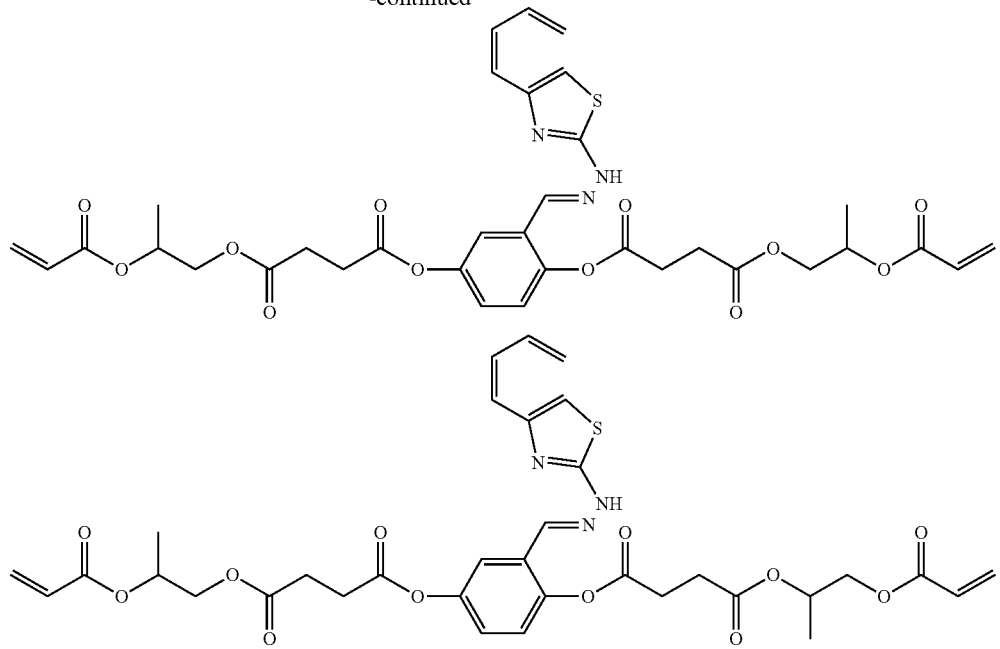

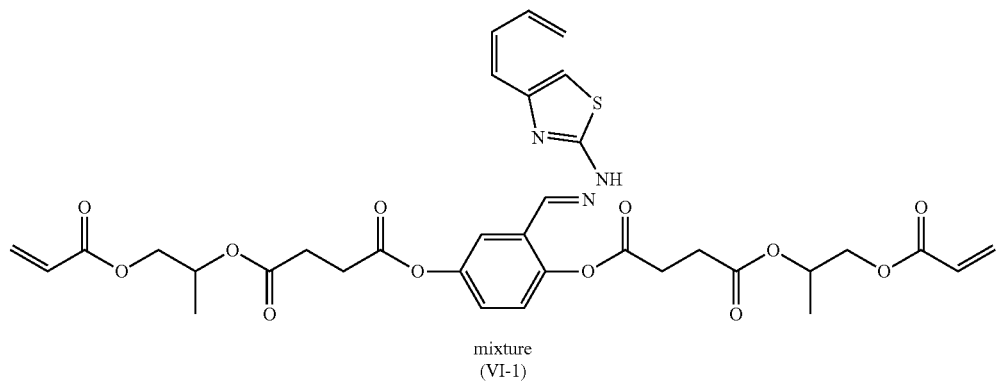

mixture
(VI-1)

<Synthesis of Compound (VI-1B)>

A compound (VI-1B) (yield 74%) was obtained in the same manner as in Synthesis Example 1, except that the compound (I-1D) in the synthesis method of the compound (I-4) described in Synthesis Example 1 was changed to 2,5-dihydroxybenzaldehyde (VI-1D).

<Synthesis of Compound (VI-1)>

0.26 g (0.46 mmol) of the compound (VI-1B), 99 mg (0.60 mmol) of 2-hydrazinobenzothiazole, 5.4 mg (0.01 mmol) of 10-camphorsulfonic acid, and 10 mL of tetrahydrofuran were mixed and stirred at room temperature for 12 hours. Ethyl acetate and water were added to the mixture for liquid separation, and the collected organic layer was washed with 1 N hydrochloric acid and saturated saline, and then dried over anhydrous sodium sulfate. Sodium sulfate was removed by filtration, the solvent was removed with a rotary evaporator, and purification was performed by silica gel chromatography, and thereby 0.22 g (0.31 mmol) of a compound (VI-1) (yield 67%) was obtained.

$^1$H-NMR (400 MHz, CDCl$_3$) δ (ppm): 1.25-1.35 (d,6H), 2.78 (t,4H), 2.85 (t,4H), 4.10-4.35 (m,2H), 5.25 (sext,2H), 7.30 (d,4H), 7.47 (br s,1H), 7.60 (d,1H), 7.80 (br d,1H), 8.09 (s,1H), 12.5 (br s,1H)

Synthesis Example 6

<Synthesis of Compound (II-2)>

A compound (II-2) was synthesized according to a synthesis method of Example 4 described in JP2016-081035A.

Synthesis Example 7

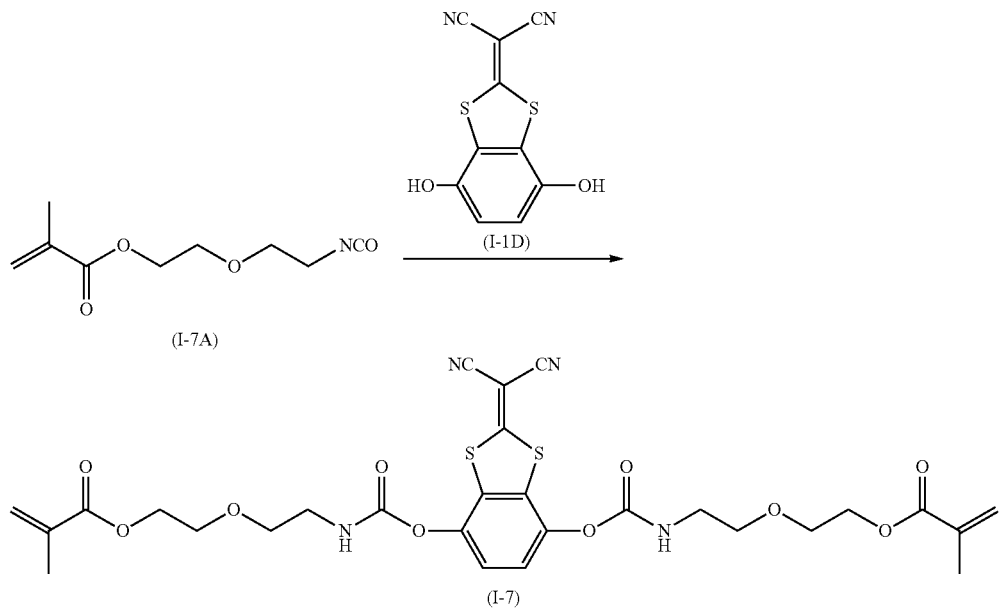

<Synthesis of Compound (I-7)>
3.9 g (19.5 mmol) of Karenz MOI-EG (I-7A, manufactured by Showa Denko K. K.), 2.7 g (10.9 mmol) of the compound (I-1D), 2 mL of N,N-dimethylacetamide, and 20 mL of chloroform were mixed, and the internal temperature was heated to 60° C. After stirring for 12 hours, the mixture was cooled to room temperature and further stirred for 12 hours. Next, after adding a saturated sodium hydrogencarbonate aqueous solution and stirring for 1 hour, liquid separation was performed. The collected organic layer was washed with 1 N hydrochloric acid and saturated brine, and then dried over anhydrous sodium sulfate, the solvent was removed with a rotary evaporator, and purification was performed by silica gel chromatography, and thereby 5.7 g (8.90 mmol) of a compound (I-7) (yield 82%) was obtained.

$^1$H-NMR (400 MHz, CDCl$_3$): δ (ppm) 1.95 (s,6H), 3.37 (m,4H), 3.60-3.70 (m,8H), 4.20 (t,4H), 5.15 (br,s,2H), 5.58 (s,2H), 6.13 (s,2H), 7.32 (s,2H)

Synthesis Example 8

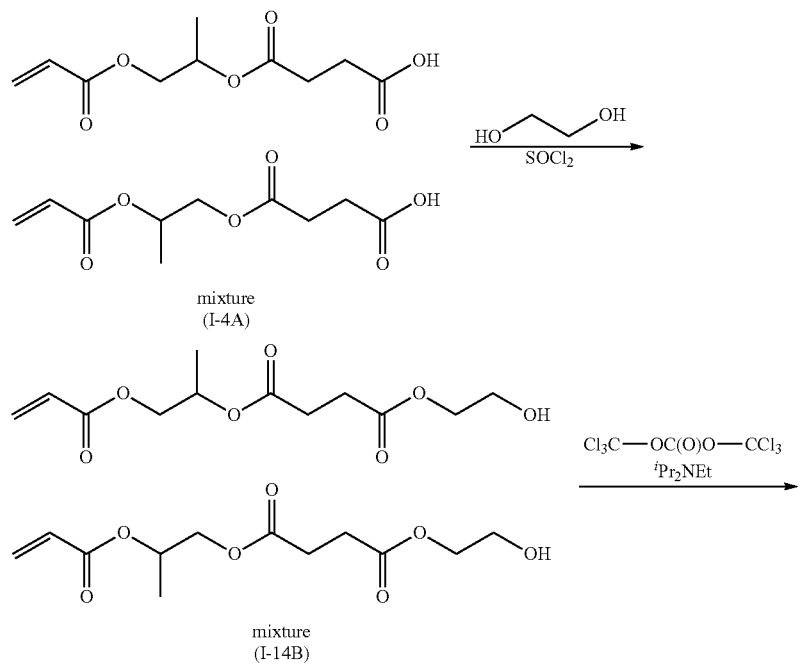

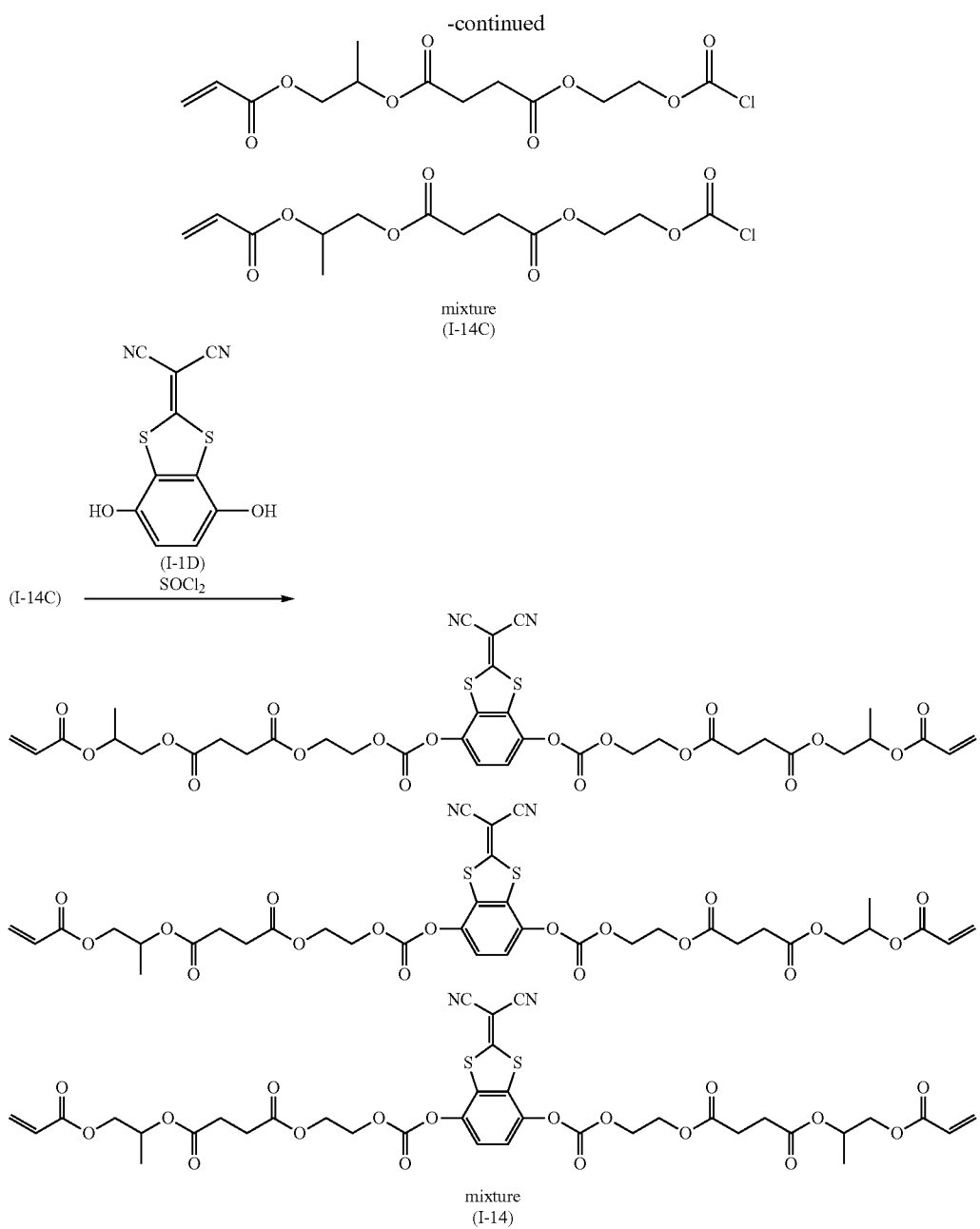

mixture
(I-14)

<Synthesis of Compound (I-14B)>

8.00 g (29.2 mmol) of the carboxylic acid compound (I-4A), 28 mL of THF, 7 mL of N,N-dimethylacetamide, and 60 mg of 2,6-di-t-butyl-4-methylphenol were mixed, and an internal temperature was cooled to 0° C. To the mixture, 4.00 g (33.6 mmol) of thionyl chloride was added dropwise at an internal temperature of 0° C. to 5° C., and the mixture was stirred at 5° C. for 60 minutes. To the obtained mixture, a solution of 10.3 g (166 mmol) of ethylene glycol and 20 mL of THF was added dropwise at an internal temperature of 0° C. to 8° C., and then stirred at an internal temperature of 20° C. to 25° C. for 8 hours.

Thereafter, the reaction solution to which 100 mL of ethyl acetate was added was washed with 100 mL of 1 N hydrochloric acid and 30 mL of 7% by mass aqueous sodium carbonate solution and separated. Thereafter, concentration was performed to obtain an oily composition, which was then purified by column chromatography, and thereby 5.8 g of a compound (I-14B) (yield 72%) was obtained.

<Synthesis of Compound (I-14C)>

A mixed solution of 1.83 g (6.19 mmol) of triphosgene, 22.5 mL of ethyl acetate, 4.90 g of the compound (I-14B), 2.9 g (19.6 mmol) of N,N-diisopropylethylamine, and 11 mL of ethyl acetate was added dropwise at 25° C. to 30° C. After stirring for 2 hours, the mixture was cooled to 0° C., washed with 17 mL of 2 N hydrochloric acid and 17 mL of saturated brine, and separated. After drying with anhydrous sodium sulfate, the solvent was removed with a rotary evaporator, and thereby 5.4 g of a compound (I-14C) which is a transparent oil (yield 90%) was obtained.

<Synthesis of Compound (I-14)>

6.75 g of the chlorocarbonic acid ester compound (I-14C) (purity 88.4%), 50 mL of ethyl acetate, 12.5 mL of N,N- dimethylacetamide, and 55 mg of 2,6-di-t-butyl-4-methylphenol were mixed, and the internal temperature was cooled to 0° C. To the mixture, 1.87 g of the compound (I-1D) and a solution of 25 mL of THF were added dropwise at an internal temperature of 0° C. to 8° C.

Thereafter, 4.60 g of N,N-diisopropylethylamine was added dropwise at an internal temperature of 0° C. to 10° C. After stirring at an internal temperature of 20° C. to 25° C. for 1 hour, 10 mL of ethyl acetate, 45 mL of water, and 4.5 mL of concentrated hydrochloric acid were added and washed. The organic layer was washed with 50 mL of saturated saline and separated, and then washed with 50 mL of saturated saline and 5 mL of 7.5% by mass aqueous sodium bicarbonate to be separated. Thereafter, concentration was performed to obtain an oily composition, which was then purified by column chromatography, and thereby a compound (I-14) (yield 75%) was obtained.

$^1$H-NMR (400 MHz, CDCl$_3$): δ (ppm) 1.25-1.35 (d,6H), 2.65-2.75 (m,8H), 4.10-4.20 (m,2H), 4.23 (t,2H), 4.43 (d,4H), 4.52 (d,4H), 5.15-5.25 (m,2H), 5.83 (m,2H), 6.05-6.15 (m,2H), 6.40 (d,2H), 7.48 (s,2H)

Synthesis Example 9

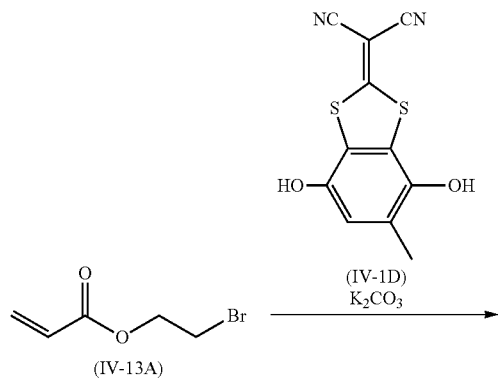

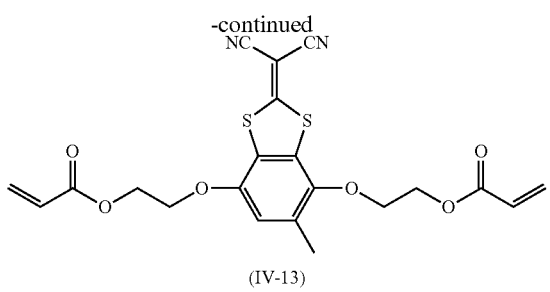

<Synthesis of Compound (IV-13)>

2.06 g (11.5 mmol) of 2-bromoethyl acrylate (IV-13A), 1.26 g (4.8 mmol) of the compound (IV-1D), 2.0 g (14.4 mmol) of potassium carbonate, 10 mg of 2,6-di-t-butyl-4-methylphenol, and 20 mL of THF were mixed, and the internal temperature was heated to 65° C. After stirring for 8 hours, the mixture was cooled to 25° C., 100 mL of ethyl acetate was added, the collected organic layer was washed with 1 N hydrochloric acid and saturated brine, and then dried over anhydrous sodium sulfate, the solvent was removed with a rotary evaporator, and purification was performed by silica gel chromatography, and thereby 1.58 g of a compound (IV-13) (yield 72%) was obtained.

$^1$H-NMR (400 MHz, CDCl$_3$): δ (ppm) 2.35 (s,3H), 4.15 (m,2H), 4.33 (m,2H), 4.45-4.60 (m,4H), 5.92 (dd,2H), 6.18 (m,2H), 6.48 (dd,2H), 6.73 (s,1H)

Synthesis Example 10

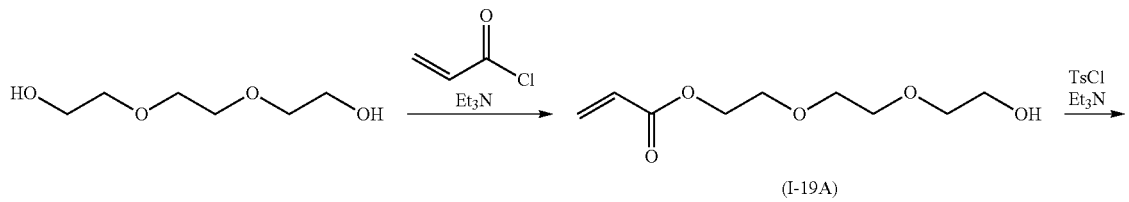

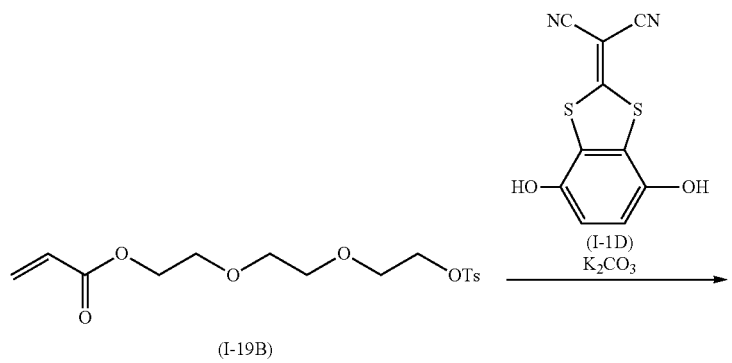

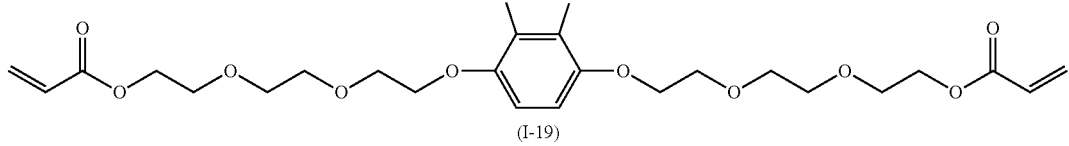

(I-19)

<Synthesis of Compound (I-19A)>

33.2 g (0.22 mol) of triethylene glycol, 490 mg of 2,6-di-t-butyl-4-methylphenol, 43 mL of N,N-dimethylacetamide, and 200 mL of THF were mixed, and the internal temperature was cooled to 0° C. 20 g (0.22 mol) of acryloyl chloride was added dropwise over 30 minutes, and thereafter, the internal temperature was set to 40° C. and the mixture was stirred for 3 hours. After filtering the precipitated salt, the solvent was removed with a rotary evaporator, purification was performed by silica gel chromatography, and thereby 20.3 g of a compound (I-19A) (yield 45%) was obtained.

<Synthesis of Compound (I-19B)>

5.0 g (24.5 mmol) of the compound (I-19A), 4.95 g (26.0 mmol) of p-toluenesulfonic acid chloride, 2.9 g (28.7 mmol) of triethylamine, 110 mg of 2,6-di-t-butyl-4-methylphenol, and 25 mL of ethyl acetate were mixed, and the internal temperature was heated to 50° C. After stirring for 5 hours, the mixture was cooled to 25° C., the collected organic layer was washed with 1 N hydrochloric acid and saturated brine, and then dried over anhydrous sodium sulfate, the solvent was removed with a rotary evaporator, and purification was performed by silica gel chromatography, and thereby 8.0 g of a compound (I-19B) (yield 91%) was obtained.

<Synthesis of Compound (I-19)>

7.0 g (19.5 mmol) of the compound (I-19B), 2.20 g (8.8 mmol) of the compound (I-1D), 9.55 g (29.3 mmol) of cesium carbonate, 50 mg of 2,6-di-t-butyl-4-methylphenol, and 50 mL of THF were mixed, and the internal temperature was heated to 70° C. After stirring for 5 hours, the mixture was cooled to 25° C., 100 mL of ethyl acetate was added, the collected organic layer was washed with 1 N hydrochloric acid and saturated brine, and then dried over anhydrous sodium sulfate, the solvent was removed with a rotary evaporator, and purification was performed by silica gel chromatography, and thereby 4.2 g of a compound (I-19) (yield 77%) was obtained.

$^1$H-NMR (solvent: DMSO-d6) δ (ppm): 3.55-3.65 (m,8H), 3.65 (d,4H), 3.76 (d,4H), 4.20 (d,4H), 4.26 (d,4H), 5.93 (d,2H), 6.10-6.20 (m,2H), 6.32 (d,2H), 7.21 (s,2H)

Synthesis Example 11

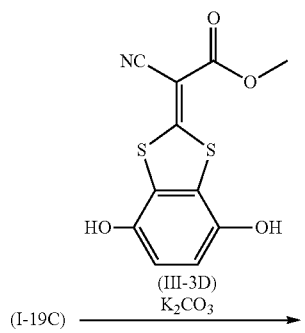

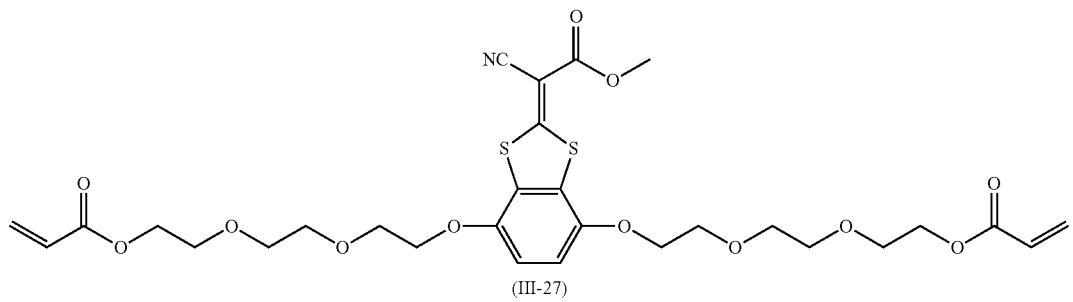

<Synthesis of Compound (III-27)>

A compound (III-27) (yield 64%) was obtained in the same manner except that the compound (I-1D) in the synthesis method of the compound (I-19) was changed to the compound (III-3D).

$^1$H-NMR (solvent: DMSO-d6) δ (ppm): 3.55-3.70 (m,12H), 3.75-3.80 (m,4H), 3.80 (s,3H), 4.20 (d,4H), 4.26 (d,4H), 5.92 (d,2H), 6.10-6.20 (m,2H), 6.32 (d,2H), 7.14 (s,2H)

Synthesis Example 12

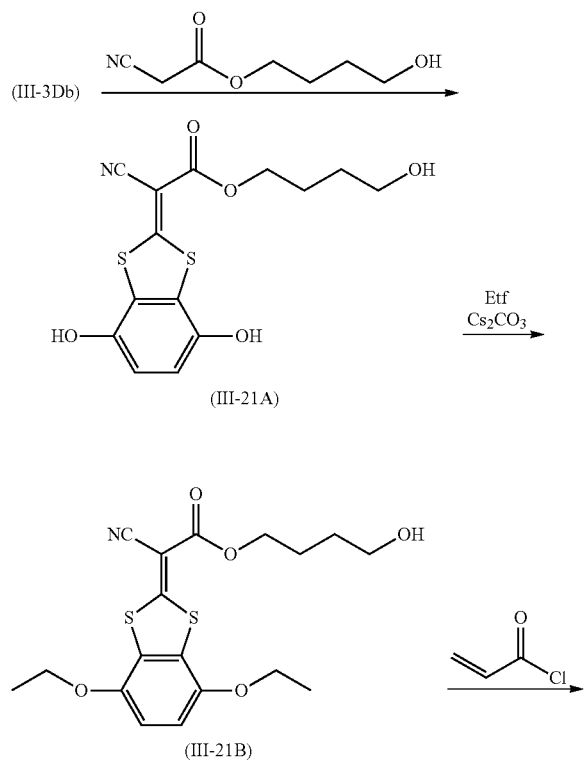

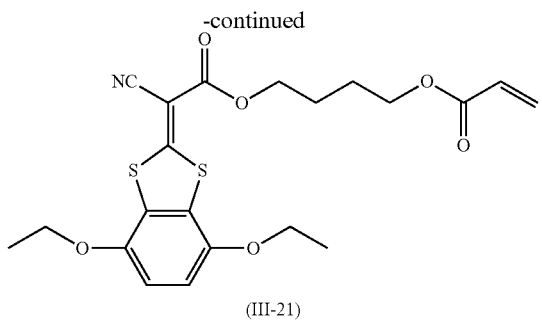

(III-21)

<Synthesis of Compound (III-21A)>

A compound (III-21A) (yield 64%) was obtained in the same manner as in Example 10 except that methyl cyanoacetate in the synthesis method of the compound (III-3D) was changed to hydroxybutyl cyanoacetate.

<Synthesis of Compound (III-21B)>

1.81 g (5.34 mmol) of the compound (III-21A), 1.83 g (11.8 mmol) of ethyl iodide, 5.22 g (16.0 mmol) of cesium carbonate, 30 mg of 2,6-di-t-butyl-4-methylphenol, and 30 mL of THF were mixed, and the internal temperature was heated to 70° C. After stirring for 5 hours, the mixture was cooled to 25° C., 100 mL of ethyl acetate was added, the collected organic layer was washed with 1 N hydrochloric acid and saturated brine, and then dried over anhydrous sodium sulfate, the solvent was removed with a rotary evaporator, and purification was performed by silica gel chromatography, and thereby 1.3 g of a compound (III-21B) (yield 62%) was obtained.

<Synthesis of Compound (III-21)>

1 g (2.5 mmol) of the compound (III-21B), 20 mg of 2,6-di-t-butyl-4-methylphenol, 40 mL of N,N-dimethylacetamide, and 200 mL of THF were mixed, and the internal temperature was cooled to 0° C. 0.25 g (2.75 mmol) of acryloyl chloride was added dropwise over 10 minutes, and thereafter, the internal temperature was set to 40° C. and the mixture was stirred for 3 hours. After filtering the precipitated salt, the solvent was removed with a rotary evaporator, purification was performed by silica gel chromatography, and thereby a compound (III-21) (yield 78%) was obtained.

$^1$H-NMR (400 MHz, CDCl$_3$): δ (ppm) 1.43 (t,6H), 1.65-1.75 (m,4H), 4.11 (q,4H), 4.15-4.25 (m,4H), 5.83 (d,1H), 6.05-6.15 (m,1H), 6.38 (d,1H), 6.75 (s,2H)

Synthesis Example 13

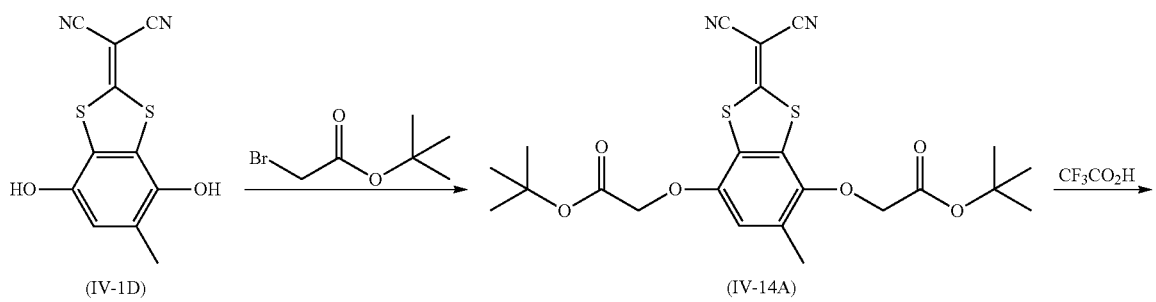

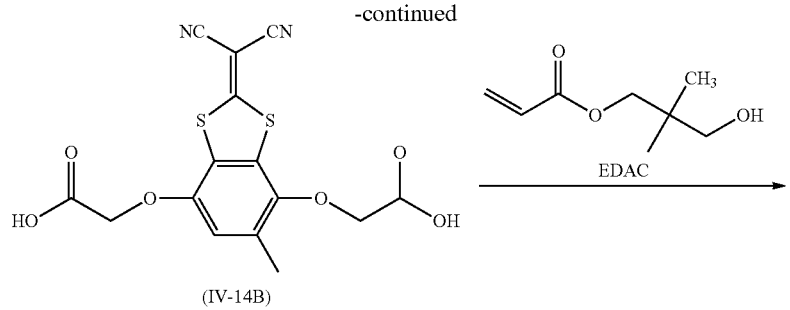

(IV-14B)

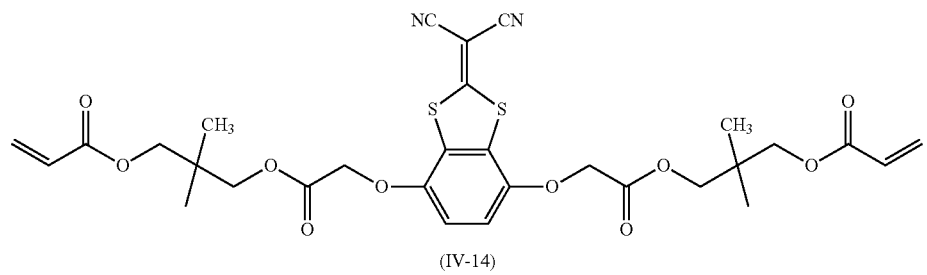

(IV-14)

<Synthesis of Compound (IV-14A)>

55.8 g (285.9 mmol) of t-butyl bromoacetate, 30 g (114.4 mmol) of the compound (IV-1D), 111.8 g (343.1 mmol) of cesium carbonate, 3.7 g (11.4 mmol) of tetrabutylammonium, 300 mL of THF, and 150 mL of N,N-dimethylacetamide were mixed, and the internal temperature was heated to 75° C. After stirring for 5 hours, the mixture was cooled to 25° C., 750 mL of water was added, and the precipitated solid was filtered. By washing with water and methanol, a compound (IV-14A) (yield 92%) was obtained.

<Synthesis of Compound (IV-14B)>

After mixing 50 g (102 mmol) of the t-butyl ester compound (IV-14A) and 500 mL of dichloromethane, 150 mL of trifluoroacetic acid was added and stirred at 25° C. for 2 hours. The internal temperature was cooled to 5° C., the precipitated crystals were filtered and washed with dichloromethane, and thereby a compound (IV-14A) (yield 98%) was obtained.

<Synthesis of Compound (IV-14)>

33.0 g (87.2 mmol) of the carboxylic acid compound (I-14B), 500 mL of dichloromethane, 26.1 g (200.6 mmol) of hydroxypropyl acrylate, 1.1 g (8.7 mmol) of N,N-dimethylaminopyridine, and 38.3 g (200.6 mmol) of 1-ethyl-3-(3-dimethylaminopropyl) carbodiimide hydrochloride (abbreviation: EDAC) were mixed. After stirring at 40° C. for 2 hours, 300 ml of 1 N aqueous hydrochloric acid was added, washed and separated. An oily composition was obtained by dehydration using magnesium sulfate, filtration, and concentration, followed by purification by column chromatography (yield 60%).

$^1$H-NMR (400 MHz, CDCl$_3$): δ (ppm) 1.25-1.35 (d,6H), 2.36 (s,3H), 4.10-4.30 (m,2H), 4.30-4.45 (m,2H), 4.52 (d,2H), 4.72 (d,2H), 5.20-5.40 (m,2H), 5.83 (m,2H), 6.05-6.15 (m,2H), 6.40 (d,2H), 6.65 (d,1H)

Synthesis Example 14

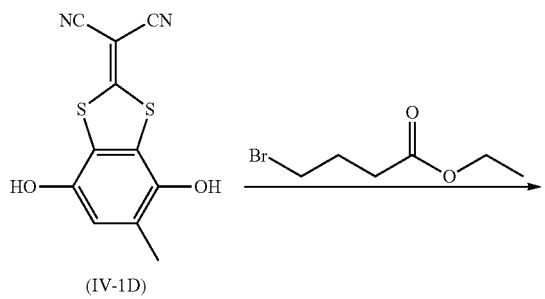

(IV-1D)

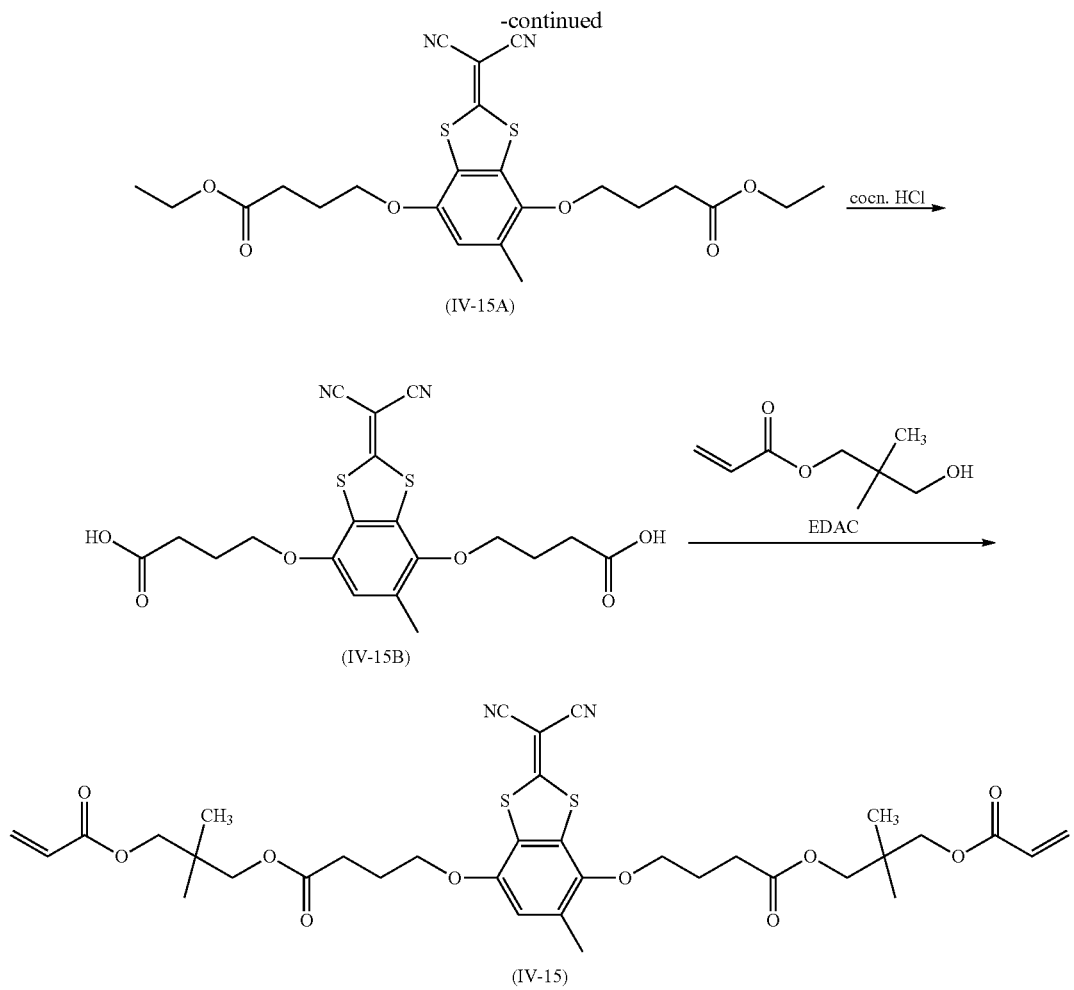

(IV-15A)

(IV-15B)

(IV-15)

<Synthesis of Compound (IV-15A)>

A compound (IV-15A) (yield 75%) was obtained in the same manner except that t-butyl bromoacetate in the synthesis method of the compound (IV-14A) described in Synthesis Example 11 was changed to 4-bromoethyl acetate.

<Synthesis of Compound (IV-15B)>

2.5 g (102 mmol) of the ester compound (IV-15A), 5 mL of concentrated hydrochloric acid, and 25 mL of acetic acid were mixed and then stirred at 60° C. for 1 hour. Thereafter, 80 mL of water was added, and the precipitated solid was filtered. The obtained solid was purified by column chromatography, and thereby a compound (IV-15B) (yield 80%) was obtained.

<Synthesis of Compound (IV-15)>

A compound (IV-15) (yield 55%) was obtained in the same manner except that the compound (IV-14B) in the synthesis method of the compound (IV-14) described in Synthesis Example 11 was changed to the compound (IV-15B).

$^1$H-NMR (400 MHz, CDCl$_3$): δ (ppm) 1.20-1.35 (m,6H), 2.10-2.20 (m,4H), 2.32 (s,3H), 2.60-2.75 (m,4H), 3.91 (t,2H), 4.10-4.30 (m,6H), 5.24 (sext,2H), 5.84 (d,2H), 6.05-6.15 (m,2H), 6.40 (d,2H), 6.70 (s,1H)

Synthesis Example 15

<Synthesis of Compound (III-31)>

A compound (III-31A) was synthesized according to a method described in paragraphs 0222 to 0223 described in JP2009-263617A (yield 24.9 g (yield 100%)).

Next, in a reaction vessel, 5 g (0.0127 mol) of the compound (III-31A), 80 mL of methylene chloride, 6.58 g (0.030 mol) of 2-acryloyloxyethyl-succinic acid (trade name HOA-MS (N), manufactured by Kyoeisha Chemical Co., Ltd.), and 0.155 g (0.0013 mol) of N,N-dimethyl-4-aminopyridine were added. While the mixture was stirred at room temperature, 5.8 g (0.030 mol) of 1-(3-dimethylaminopropyl)-3-ethylcarbodiimide hydrochloride was added, and then reacted at 40° C. for 1 hour. To the obtained reaction solution, 200 mL of ethyl acetate and 100 mL of water were added for liquid separation, and then the collected organic layer was washed with 100 mL of saturated sodium bicarbonate water and dried over magnesium sulfate. The organic solvent contained in the organic layer was removed with a rotary evaporator, purification was performed by silica gel chromatography, and thereby 4.2 g of a compound (III-31) was obtained.

$^1$H-NMR (300 MHz, CDCl$_3$): δ (ppm) 0.92 (t,6H), 1.31 (sext,4H), 1.55 (quin,4H), 2.82 (t,4H), 2.97 (t,4H), 3.66 (t,4H), 4.40 (s,8H), 5.82 (d,2H), 6.05-6.15 (m,2H), 6.41 (d,2H), 7.30 (s,2H)

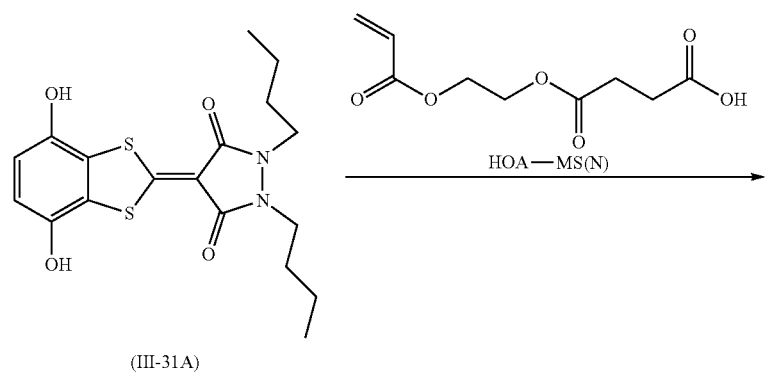
(III-31A)
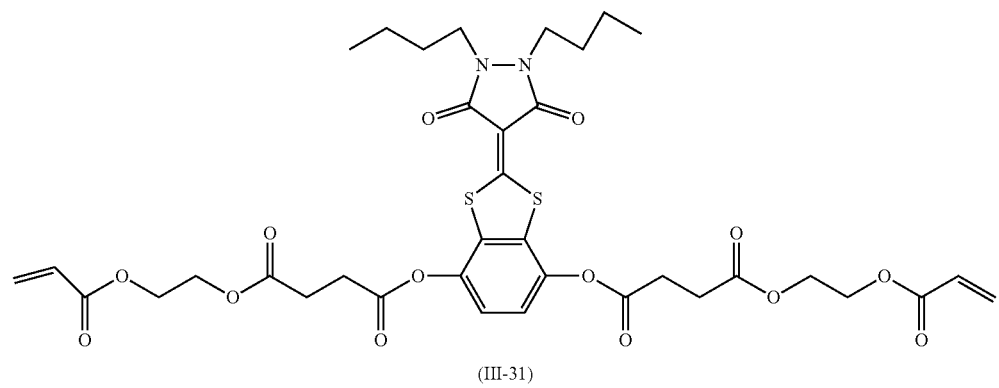
(III-31)
<Synthesis of Comparative Compound (Z-1)>
A compound having the following structure was synthesized by the method described in JP2014-043565A. This was designated as a comparative compound Z-1.
Comparative compound Z-1
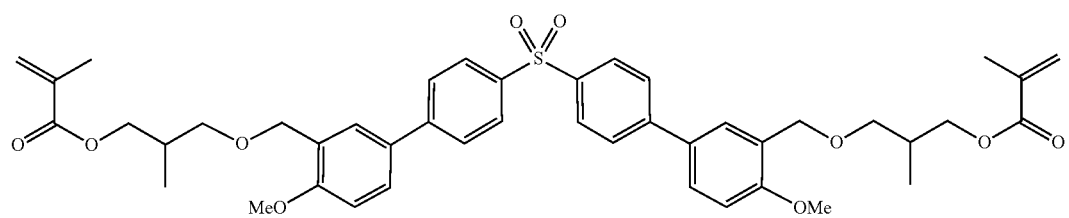

Examples 1 to 15 and Comparative Example 1

<Preparation of Curable Resin Composition>
A monomer 1 (a (meth)acrylate monomer) and a photoinitiator (IRGACURE 819) were mixed as a component (A) and a component (B) so as to make the composition described in the following Table 1, the mixture was stirred to make it uniform, and thereby a curable composition was prepared.

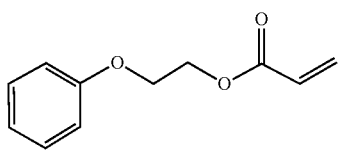

Monomer 1

<Production of Cured Product Sample for Optical Property Measurement>
The prepared curable resin composition was poured into a circular transparent glass mold having a diameter of 20 mm so that a thickness of the cured product became 2 mm, and using a UV irradiation apparatus (EXECURE 3000, manufactured by HOYA), irradiation with an ultraviolet ray of 15 mW/cm$^2$ was performed for 150 seconds in an atmosphere having an oxygen concentration of 1% or less, and thereby a cured product was obtained.

<Optical Characteristics Measurement>
An average value of "birefringence Δn" was measured by measuring a birefringence within a circle of 10 mm in diameter including the center of the produced cured product using a birefringence evaluation apparatus (WPA-100, manufactured by Photonic Lattice, Inc.).

A "refractive index (nd)," an "Abbe number (vd)," and a "partial dispersion ratio (θg, F)" were measured by processing the cured product obtained by the cured sample production method (2) into a V-shaped block, and using a Kalnew precision refractometer KPR-2000 (manufactured by Shimadzu Device Corporation). The measurement was performed three times for each sample at 25° C., and an average value was taken as a measurement result.

A "refractive index (nd)" is a refractive index at a wavelength of 587.56 nm. In addition, an "Abbe number (vd)" and a "partial dispersion ratio (θg, F)" are values calculated from the refractive index measurement values at different wavelengths according to the following equations.

$$vd=(nd-1)/(nF-nC)$$

$$\theta g, F=(ng-nF)/(nF-nC)$$

Where, nd represents a refractive index at a wavelength of 587.56 nm, nF represents a refractive index at a wavelength of 486.13 nm, nC represents a refractive index at a wavelength of 656.27 nm, and ng represents a refractive index at a wavelength of 435.83 nm.

<Production of Cured Product Sample for Heat Shock Resistance Test>
The prepared curable resin composition was poured into a circular transparent glass mold having a diameter of 15 mm so that a thickness of the cured product became 2 mm, and using a UV irradiation apparatus (EXECURE 3000, manufactured by HOYA), irradiation with an ultraviolet ray of 15 mW/cm$^2$ was performed for 100 seconds in an atmosphere having an oxygen concentration of 1% or less, and thereby a cured product was obtained.

<Heat Shock Resistance Test>
Ten produced cured products were heated at 100° C. for 48 hours, and then the temperature was returned to room temperature, and the cured products were further cooled to −40° C., allowed to elapse for 48 hours, and then the temperature was returned to room temperature. The sample was observed with a digital microscope manufactured by Keyence Corporation and a laser microscope. A product in which a change in shape such as distortion or crack was recognized was regarded as a defective product, and a product in which such a change was not generated was regarded as a non-defective product. The ten cured products were evaluated, and the percentage of non-defective products among them was evaluated as a non-defective rate, and evaluation was performed according to the following standards.

A: The non-defective rate was 80% or more.
B: The non-defective rate was 70% or more and less than 80%.
C: The non-defective rate was less than 70%.

TABLE 1

|  |  | Example 1 | Example 2 | Example 3 | Example 4 | Example 5 | Example 6 | Example 7 | Example 8 |
|---|---|---|---|---|---|---|---|---|---|
| Component (A) | V-3 | 64.4 |  |  |  |  |  |  |  |
|  | VI-1 |  | 64.4 |  |  |  |  |  |  |
|  | II-2 |  |  | 64.4 |  |  |  |  |  |
|  | I-4 |  |  |  | 64.4 |  |  |  |  |
|  | III-3 |  |  |  |  | 64.4 |  |  |  |
|  | IV-1 |  |  |  |  |  | 64.4 |  |  |
|  | I-7 |  |  |  |  |  |  | 64.4 |  |
|  | I-14 |  |  |  |  |  |  |  | 64.4 |
|  | IV-13 |  |  |  |  |  |  |  |  |
|  | I-19 |  |  |  |  |  |  |  |  |
|  | III-27 |  |  |  |  |  |  |  |  |
|  | III-21 |  |  |  |  |  |  |  |  |
|  | Comparative compound Z-1 |  |  |  |  |  |  |  |  |

TABLE 1-continued

| Component (B) | Monomer 1 | 34.6 | 34.6 | 34.6 | 34.6 | 34.6 | 34.6 | 34.6 | 34.6 |
|---|---|---|---|---|---|---|---|---|---|
| Photoinitiator | Irgacure 819 | 1 | 1 | 1 | 1 | 1 | 1 | 1 | 1 |
| Total | | 100 | 100 | 100 | 100 | 100 | 100 | 100 | 100 |
| Characteristics | An | 0.0004 | 0.0007 | 0.0005 | 0.0006 | 0.0004 | 0.0005 | 0.0004 | 0.0005 |
| of cured | ad | 1.576 | 1.567 | 1.611 | 1.550 | 1.549 | 1.551 | 1.555 | 1.542 |
| product | vd | 21.8 | 20.9 | 24.5 | 20.8 | 22.9 | 20.7 | 20.5 | 22.7 |
| | θg,F | 0.81 | 0.79 | 0.73 | 0.82 | 0.76 | 0.85 | 0.84 | 0.78 |
| | Heat shock resistance | B | B | A | A | A | A | A | A |

| | | Example 9 | Example 10 | Example 11 | Example 12 | Example 13 | Example 14 | Example 15 | Comparative Example 1 |
|---|---|---|---|---|---|---|---|---|---|
| Component (A) | V-3 | | | | | | | | |
| | VI-1 | | | | | | | | |
| | II-2 | | | | | | | | |
| | I-4 | | | | | | | | |
| | III-3 | | | | | | | | |
| | IV-1 | | | | | | | | |
| | I-7 | | | | | | | | |
| | I-14 | | | | | | | | |
| | IV-13 | 64.4 | | | | | | | |
| | I-19 | | 64.4 | | | | | | |
| | III-27 | | | 64.4 | | 20 | 99 | 96 | |
| | III-21 | | | | 64.4 | | | | |
| | Comparative compound Z-1 | | | | | | | | 64.4 |
| Component (B) | Monomer 1 | 34.6 | 34.6 | 34.6 | 34.6 | 79 | 0 | 3 | 34.6 |
| Photoinitiator | Irgacure 819 | 1 | 1 | 1 | 1 | 1 | 1 | 1 | 1 |
| Total | | 100 | 100 | 100 | 100 | 100 | 100 | 100 | 100 |
| Characteristics | An | 0.0003 | 0.0006 | 0.0008 | 0.0005 | 0.0005 | 0.0007 | 0.0003 | 0.0005 |
| of cured | ad | 1.597 | 1.560 | 1.561 | 1.571 | 1.531 | 1.583 | 1.580 | 1.570 |
| product | vd | 12.6 | 20.3 | 22.4 | 22.0 | 26.93 | 17.3 | 17.6 | 22.2 |
| | θg,F | 1.27 | 0.87 | 0.81 | 0.83 | 0.71 | 0.93 | 0.93 | 0.69 |
| | Heat shock resistance | B | A | A | A | A | B | A | C |

An amount of each component in the table is mass %.

Based on the results shown in Table 1, it could be understood that Examples 1 to 15 have higher θg, F than Comparative Example 1.

In Examples 1, 2, 4 to 12, 14, and 15, all of θg, F were 0.75 or more, and preferable results were obtained.

Example 3 (liquid crystal) was compared with Example 4, and Example 4 has higher θg, F. In the component A, a ratio of the side chain portion to the core portion of the compound was small, and the reason for this is considered to be that $Sp_1$ and $Sp_2$ have no ring structure.

In General Formula 1, compounds in which $L_1$ and $L_2$ are —O— are more preferable because of higher θg, F (comparison between Example 4 and Example 5, and Example 10 and Example 11).

Even in Example 13 in which an amount of component A added was reduced to 20% by mass with respect to Example 11, a result in which high heat shock resistance was maintained was obtained.

In Example 14 in which an amount of component A added was increased to 99% by mass with respect to Example 11, the heat shock resistance was higher than that in Comparative Example 1, and in Example 15 in which an amount of component A added was increased to 96% by mass, a result in which heat shock resistance became further higher was obtained.

Examples 16 to 20 and Comparative Example 2

<Preparation 2 of Curable Resin Composition>

A monomer 8 (a (meth)acrylate monomer) and two kinds of photoinitiator (IRGACURE 819 and IRGACURE 184) were mixed as a component (A) and a component (B) so as to make the composition described in Table 2, the mixture was stirred to make it uniform, and thereby a curable composition was prepared.

Monomer 8

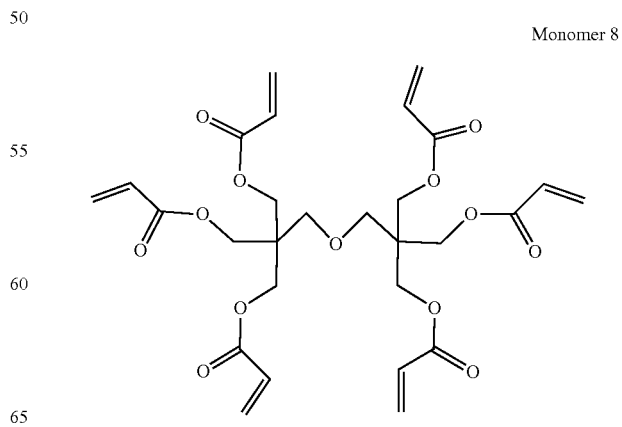

<Production of Cured Product Sample for Rub Resistance Test and Light Resistance Test>

The prepared curable resin composition was poured into a circular transparent glass mold having a diameter of 20 μm so that a thickness of the cured product became 50 mm, and using a UV irradiation apparatus (EXECURE 3000, manufactured by HOYA), irradiation with an ultraviolet ray of 15 mW/cm$^2$ was performed for 100 seconds in an atmosphere having an oxygen concentration of 1% or less, and thereby a cured product was obtained.

<Rub Resistance Test>

Using a rub resistance tester, by allowing Bencott (registered trademark; wiper for clean room), which is manufactured by Asahi Kasei Corporation, to reciprocate the surface of the cured product 2000 times with a load of 200 g at room temperature (25° C.), the surface of the cured product was rubbed. The rub resistance was evaluated by measuring a UV-visible transmittance at the center (diameter 5 mm) of the cured product before and after the rub resistance test, and obtaining a width of decrease in the transmittance at a wavelength of 589 nm (transmission before the rub resistance test—transmittance after the rub resistance test). In a case where the rub resistance was favorable, the surface of the cured product was not easily scratched, and a width of decrease in transmittance became small.

<Light Resistance Test>

The prepared cured product was irradiated with 200 J/cm$^2$ of ultraviolet rays using Execute 3000. Before and after UV irradiation, a UV-visible transmittance was measured at the center of the cured product (diameter: 5 mm), and a width of decrease in the transmittance at a wavelength of 430 nm (transmittance before UV irradiation—transmittance after UV irradiation) was obtained.

General Formula 2-2

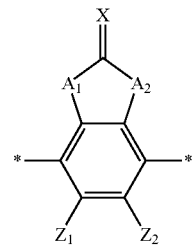

in formula $Z_1$ and $Z_2$ each independently represent a hydrogen atom, a methyl group, or an ethyl group $A_1$ and $A_2$ each independently represent —S—, X represents C to which two cyano groups are bonded, C to which a cyano group and an alkoxy carbonyl group are bonded, or a ring represented by the following formula;

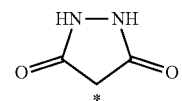

wherein the ring represented by the above formula may be substituted by one or two alkyl groups having 1 to 6 carbon atoms and * represents a bonding position, $L_1$ and $L_2$ each independently represent —O—, —OC(=O)—, —C(=O)—, —OC(=O)O—, —OC(=O)NH—, or —NHC(=O)O—,

TABLE 2

|  |  | Example 16 | Example 17 | Example 18 | Example 19 | Example 20 | Comparative Example 2 |
|---|---|---|---|---|---|---|---|
| Component (A) | IV-1 | 64.4 |  |  |  |  |  |
|  | III-3 |  | 64.4 |  |  |  |  |
|  | IV-14 |  |  | 45 |  |  |  |
|  | IV-15 |  |  |  | 45 |  |  |
|  | III-31 |  |  |  |  | 40 |  |
|  | Comparative compound Z-1 |  |  |  |  |  | 64.4 |
| Component (B) | Monomer 8 | 33.6 | 33.6 | 53 | 53 | 58 | 33.6 |
| Photoinitiator | Irgacure 819 | 1 | 1 | 1 | 1 | 1 | 1 |
|  | Irgacure 184 | 1 | 1 | 1 | 1 | 1 | 1 |
| Total |  | 100 | 100 | 100 | 100 | 100 | 100 |
| Characteristics of cured product | Δn | 0.0007 | 0.0004 | 0.0005 | 0.0003 | 0.0004 | 0.0006 |
|  | nd | 1.553 | 1.533 | 1.541 | 1.533 | 1.528 | 1.553 |
|  | vd | 23.4 | 25.2 | 27.5 | 26.8 | 26.5 | 24.3 |
|  | θg,F | 0.78 | 0.74 | 1.10 | 1.21 | 1.31 | 0.68 |
|  | Rub resistance | 3.2% | 3.3% | 0.2% | 0.3% | <0.1% | 15.4% |
|  | Light resistance | 5.5% | 6.5% | 3.4% | 2.2% | 0.7% | 18.3% |

An amount of each component in the table is mass%.

What is claimed is:

1. A cured product obtained by curing a curable composition including a compound represented by General Formula 1, wherein a birefringence Δn at a wavelength of 587 nm is 0.00≤Δn≤0.01, $$Pol_1\text{-}Sp_1\text{-}L_1\text{-}Ar\text{-}L_2\text{-}Sp_2\text{-}Pol_2 \quad \text{(General Formula 1)}$$

in formula, Ar is an aromatic ring group represented by General Formula 2-2, and $Sp_1$ and $Sp_2$ each independently represent a linking group selected from the group consisting of a linear alkylene group which has 2 to 30 carbon atoms and may be substituted with a methyl group or a linear alkylene group which has 1 to 30 carbon atoms and may be substituted with a methyl group and in which one —CH$_2$— or two or more non-adjacent —CH$_2$—'s are substituted by —O—, —S—, —OC(=O)—, —C(=O)O—, —OC(=O)O—, —NHC(=O)—, —C(=O)NH—, —OC(=O)NH—, or —NHC(=O)O, and Pol₁ and Pol₂ each independently represent a (meth)acryloyloxy group.

2. The cured product according to claim 1,
wherein $L_1$ and $L_2$ are all —O—, —OC(=O)—, —OC(=O)O—, or O—C(=O)NH—.

3. The cured product according to claim 2,
wherein $L_1$ and $L_2$ are all —O—.

4. A lens comprising the cured product according to claim 1.

5. A compound represented by General Formula 1, $$Pol_1\text{-}Sp_1\text{-}L_1\text{-}Ar\text{-}L_2\text{-}Sp_2\text{-}Pol_2 \quad \text{(General Formula 1)}$$

in formula, Ar is an aromatic ring group represented by General Formula 2-2, and

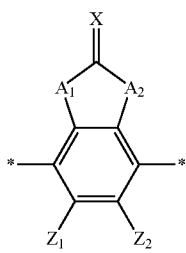

General Formula 2-2 in formula, $Z_1$ and $Z_2$ each independently represent a hydrogen atom, a methyl group, or an ethyl group $A_1$ and $A_2$ each independently represent —S—, X represents C to which two cyano groups are bonded, C to which a cyano group and an alkoxy carbonyl group are bonded, or a ring represented by the following formula;

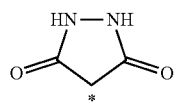

wherein the ring represented by the above formula may be substituted by one or two alkyl groups having 1 to 6 carbon atoms and * represents a bonding position, $L_1$ and $L_2$ each independently represent —O—, —OC(=O)—, —C(=O)O—, —OC(=O)O—, —OC(=O)NH—, or —NHC(=O)O—, $Sp_1$ and $Sp_2$ each represent a linking group selected from the group consisting of a linear alkylene group which has 2 to 30 carbon atoms and may be substituted with a methyl group or a linear alkylene group which has 1 to 30 carbon atoms and may be substituted with a methyl group and in which one —CH₂— or two or more non-adjacent —CH₂—'s are substituted by —O—, —S—, —OC(=O)—, —C(=O)O—, —OC(=O)O—, —NHC(=O)—, —C(=O)NH—, —OC(=O)NH—, or —NHC(=O)O, and Pol₁ and Pol₂ each independently represent a (meth)acryloyloxy group.

6. The compound according to claim 5,
wherein $L_1$ and $L_2$ are all —O—, —OC(=O)—, —OC(=O)O—, or O—C(=O)NH—.

7. The compound according to claim 6,
wherein $L_1$ and $L_2$ are all —O—.

8. The compound according to claim 5,
which is represented by any one of the following formulae:

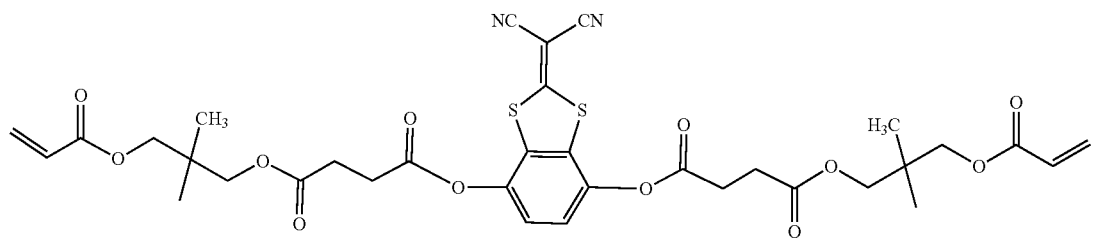

(I-4)

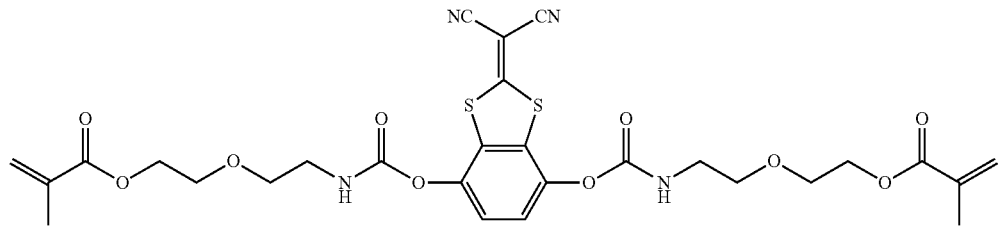

(I-7)

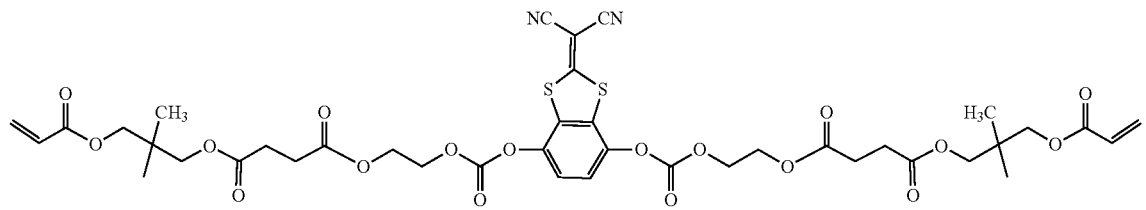

(I-14)

-continued
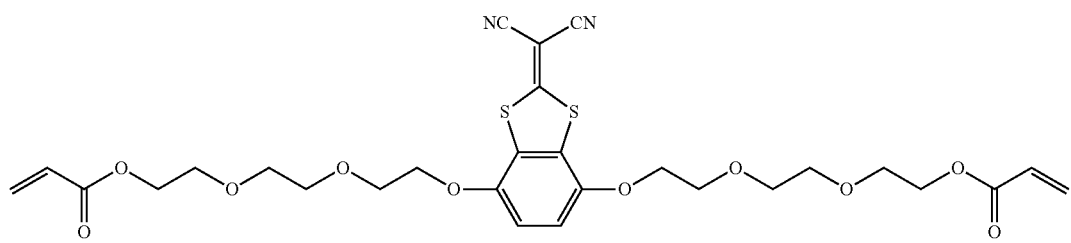
(I-19)
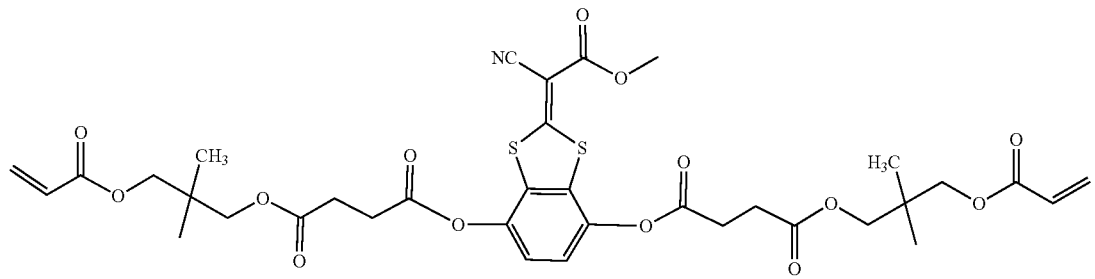
(III-3)
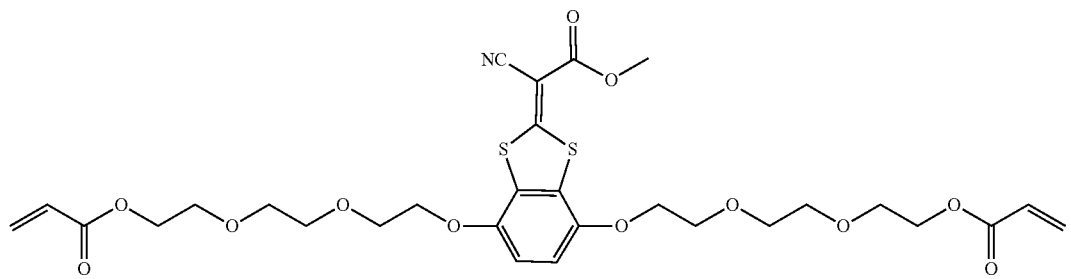
(III-27)
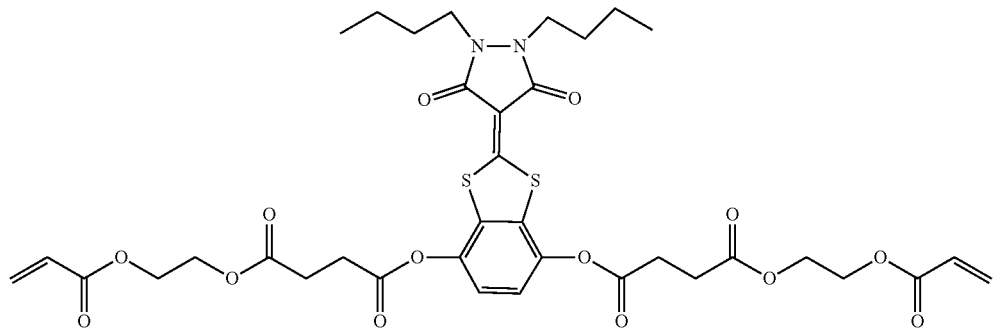
(III-31)
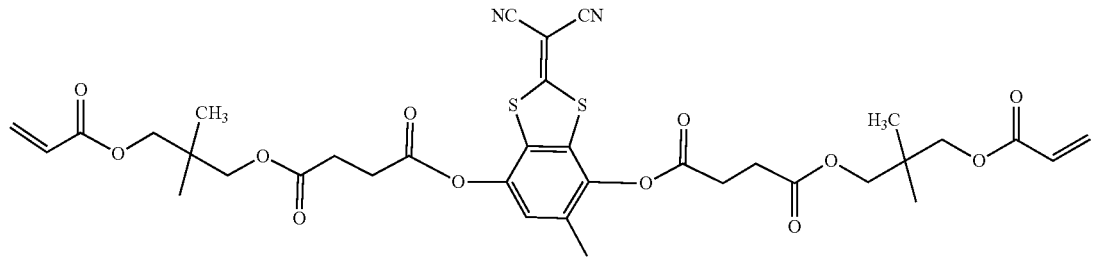
(IV-1)

-continued (IV-13)
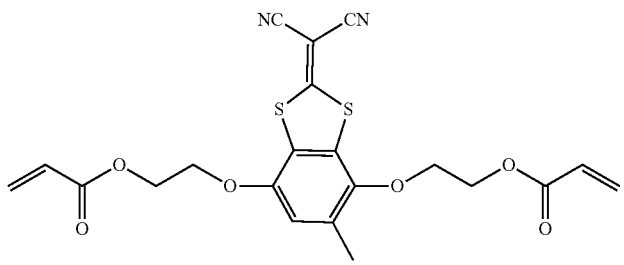

(IV-14)
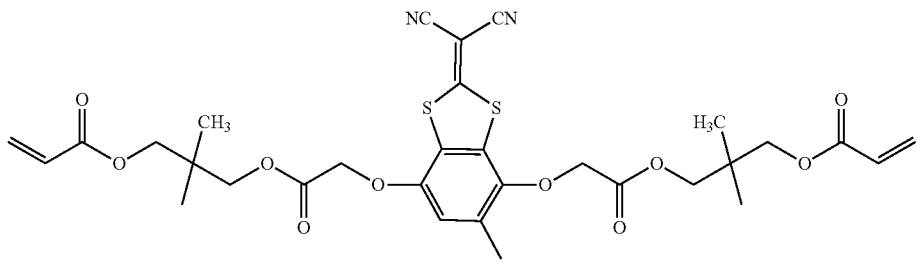

(IV-15)
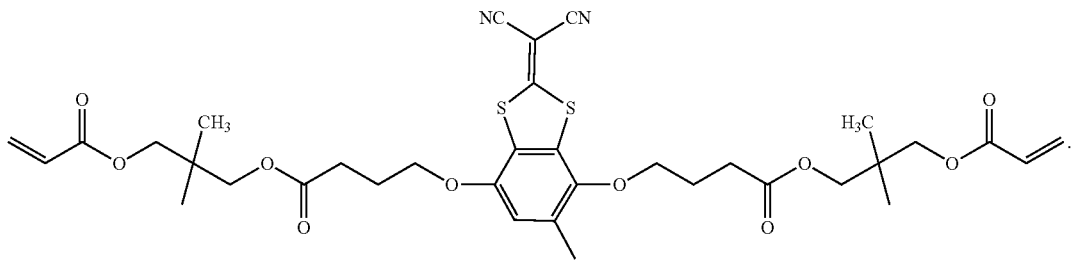

9. A curable composition comprising:
the compound according to claim 5; and
a polyfunctional (meth)acrylate monomer having three or more (meth)acryloyl groups in a molecule.

10. A curable composition comprising:
the compound according to claim 6; and
a polyfunctional (meth)acrylate monomer having three or more (meth)acryloyl groups in a molecule.

11. A curable composition comprising:
the compound according to claim 8; and
a polyfunctional (meth)acrylate monomer having three or more (meth)acryloyl groups in a molecule.

12. The cured product according to claim 1,
wherein X represents any one of the following formulae;

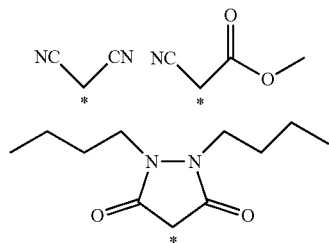

wherein * represents a bonding position of the C, and
Sp$_1$ and Sp$_2$ each represent a linking group selected from the following formulae;

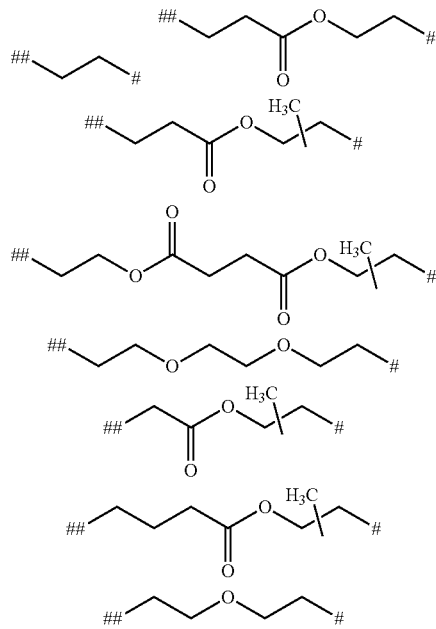

wherein ## represents a position bonding to L$_1$ or L$_2$ and # represents a position bonding to Pol$_1$ or Pol$_2$.

13. The cured product according to claim 1,
wherein the compound represented by General Formula 1 is represented by any one of the following formulae

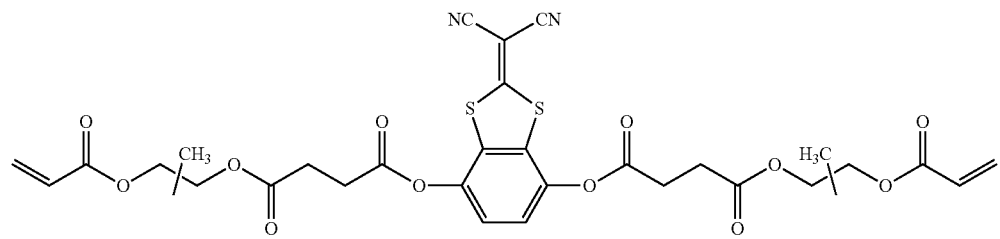
(I-4)
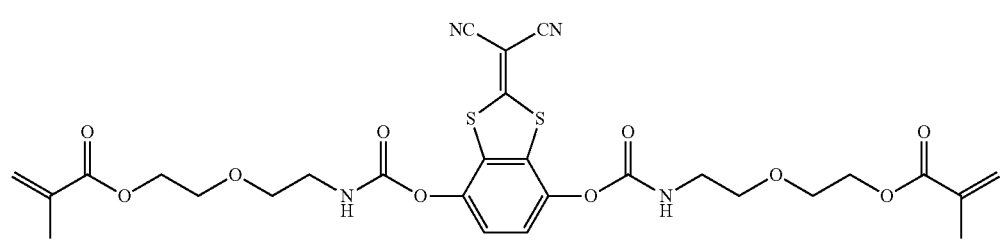
(I-7)
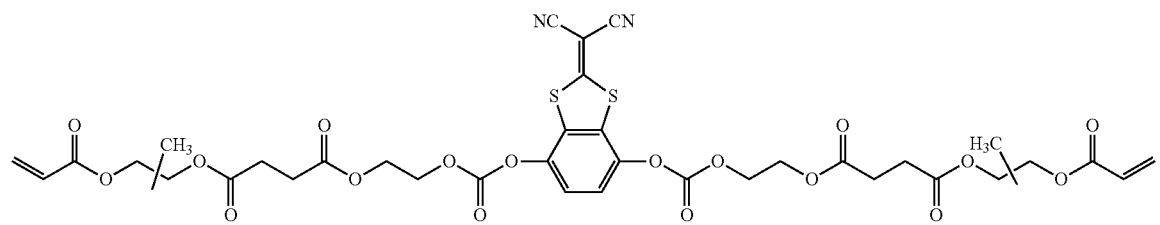
(I-14)
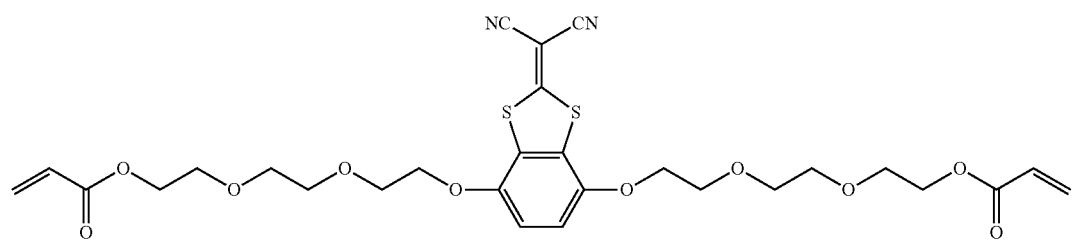
(I-19)
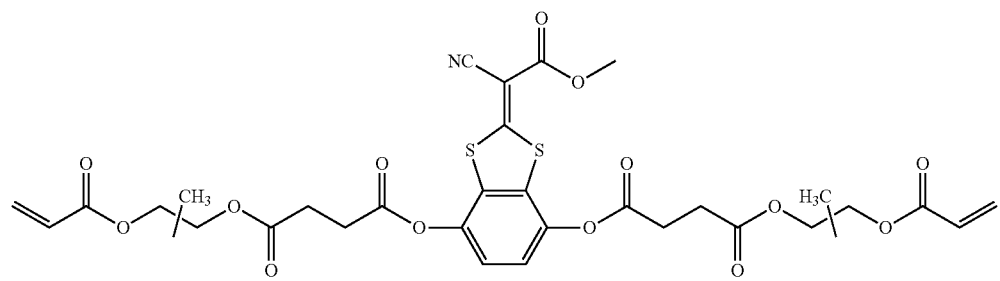
(III-3)
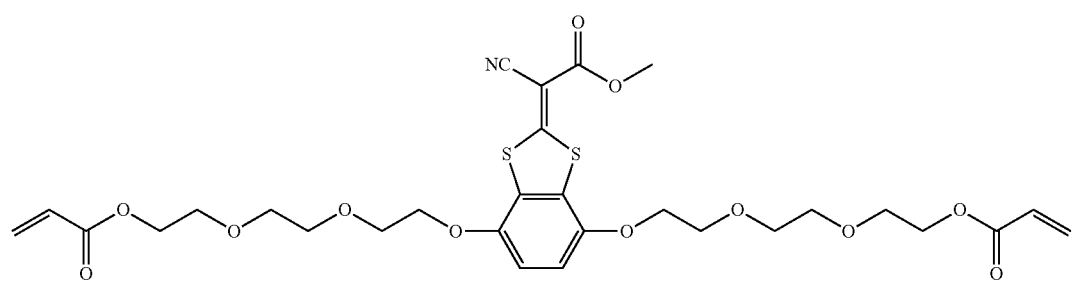
(III-27)

-continued
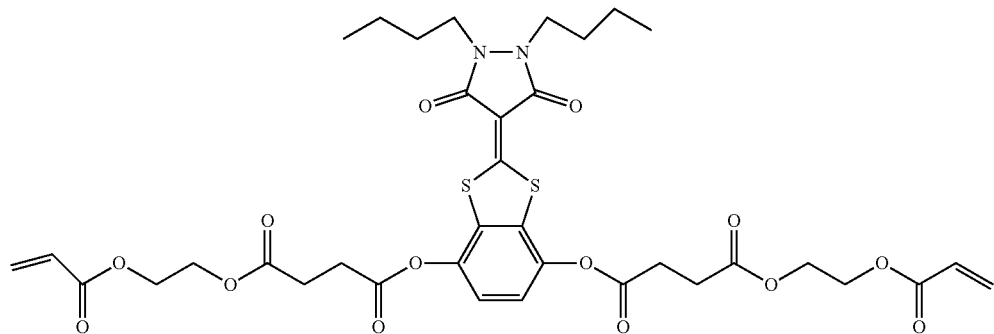
(III-31)
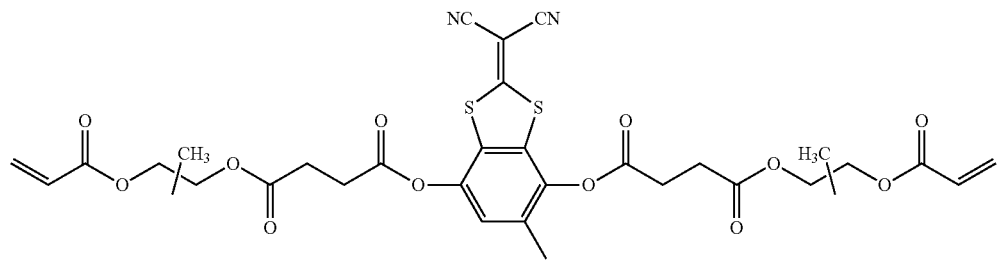
(IV-1)
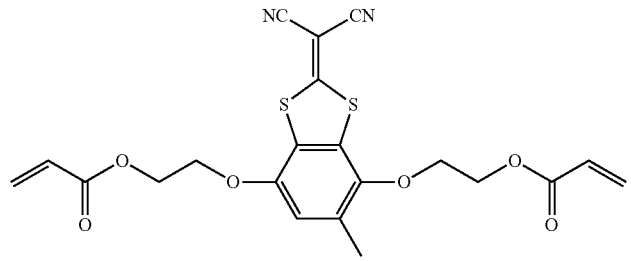
(IV-13)
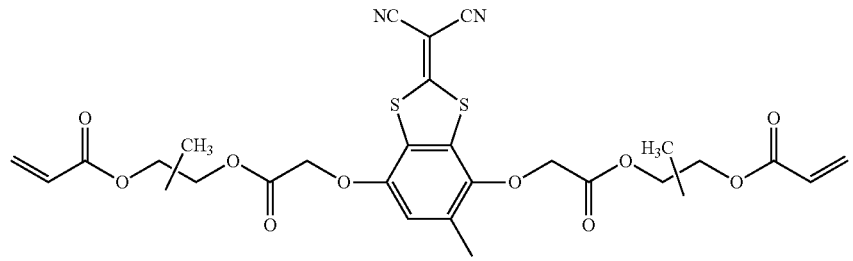
(IV-14)
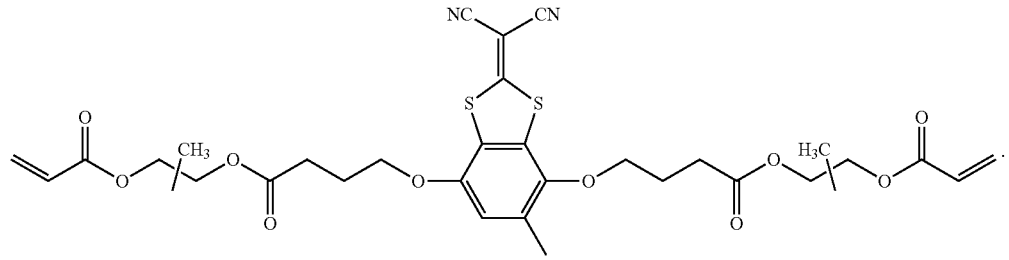
(IV-15)

14. The cured product according to claim 1,
wherein the compound represented by General Formula 1
is represented by any one of the following formulae
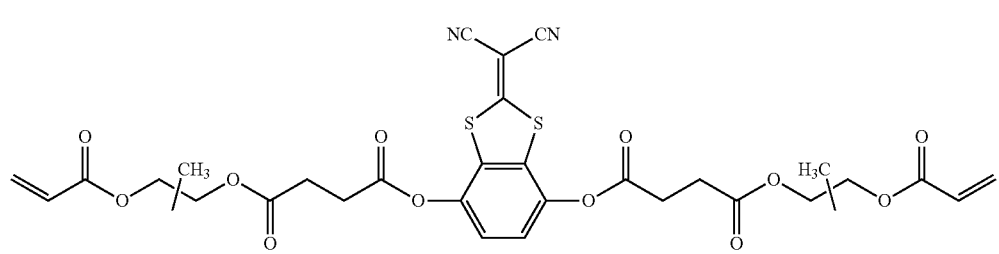
(I-4)
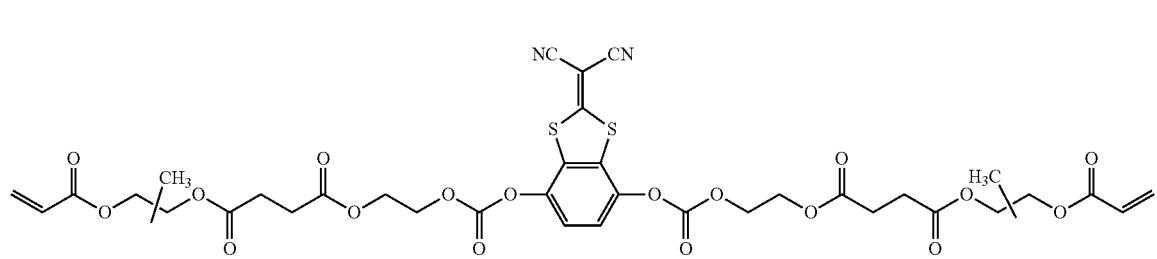
(I-14)
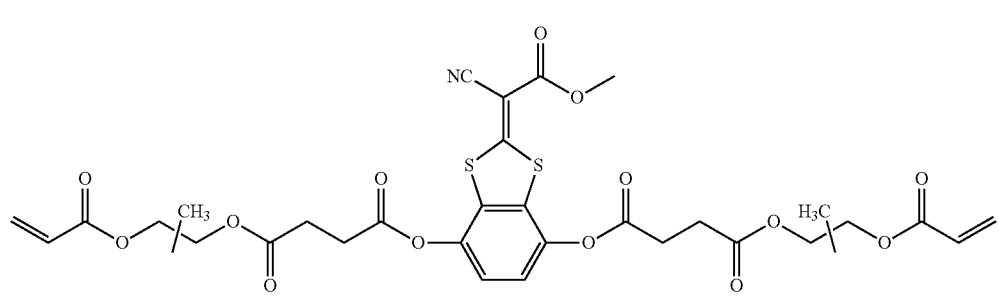
(III-3)
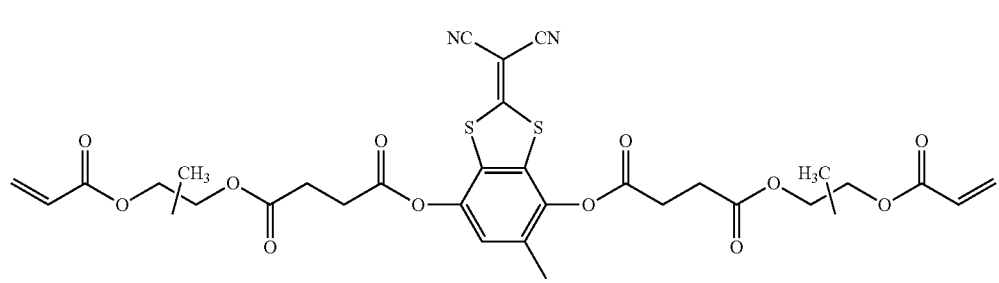
(IV-1)
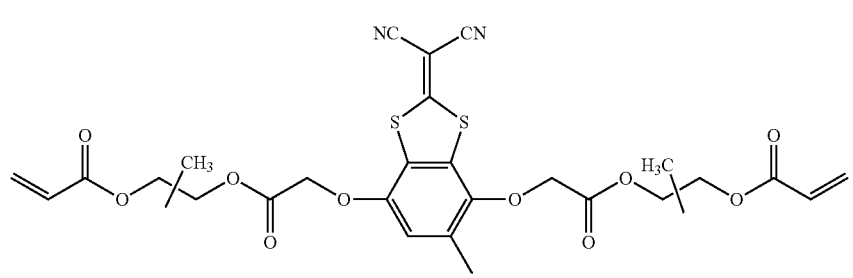
(IV-14)

(IV-15)

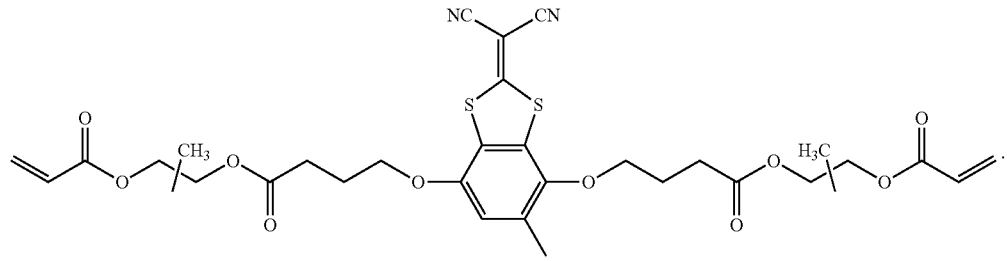

15. The compound according to claim 5, wherein X represents any one of the following formulae;

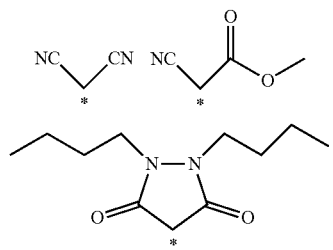

in the formulae * represents a bonding position, and

Sp$_1$ and Sp$_2$ each represent a linking group selected from the following formulae;

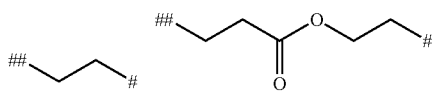

wherein ## represents a position bonding to L$_1$ or L$_2$ and # represents a position bonding to Pol$_1$ or Pol$_2$.

16. The compound according to claim 5, which is represented by any one of the following formulae (I-4)

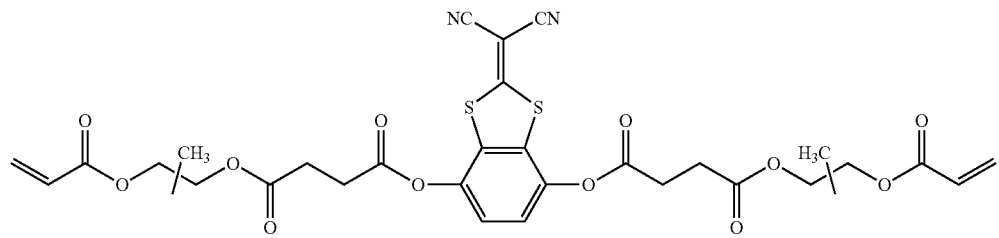

(I-14)

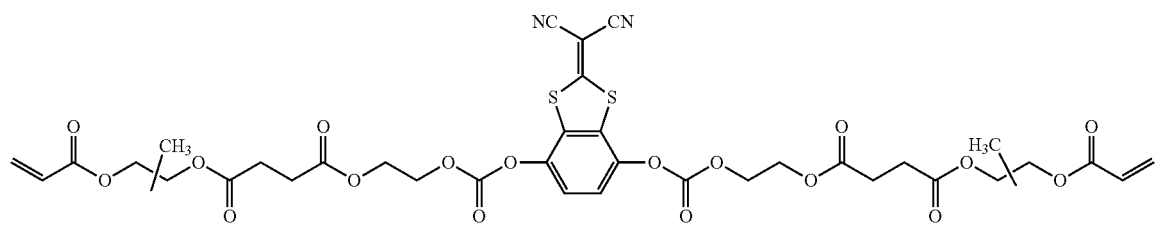

-continued
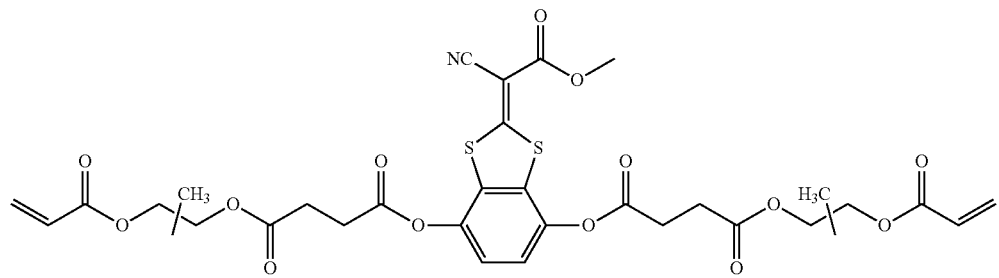
(III-3)
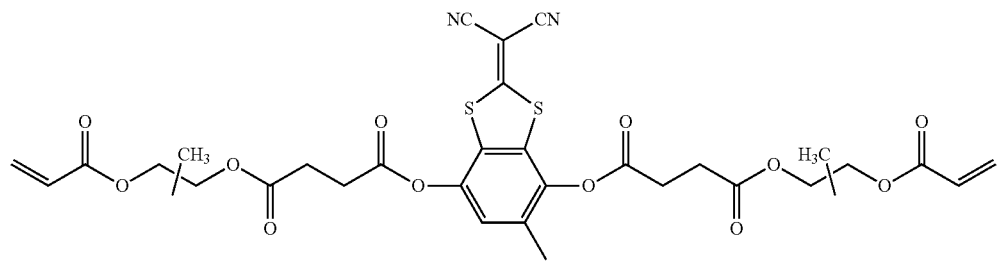
(IV-1)
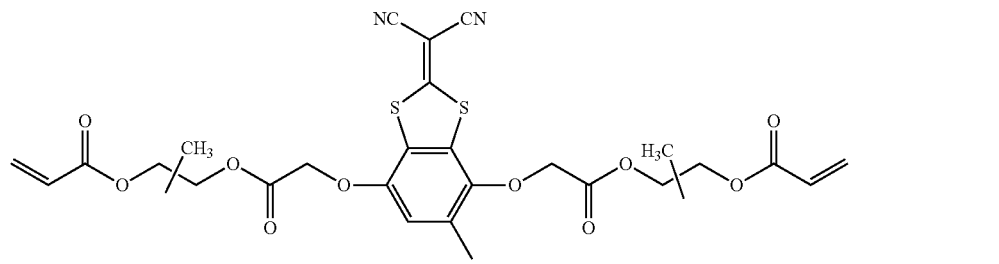
(IV-14)
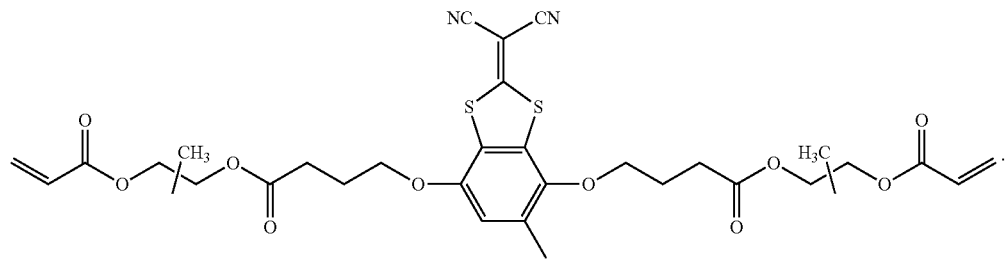
(IV-15)
* * * * *